(12) United States Patent
Quadros et al.

(10) Patent No.: US 8,524,454 B2
(45) Date of Patent: Sep. 3, 2013

(54) TRANSCOBALAMIN RECEPTOR POLYPEPTIDES, NUCLEIC ACIDS, AND MODULATORS THEREOF, AND RELATED METHODS OF USE IN MODULATING CELL GROWTH AND TREATING CANCER AND COBALAMIN DEFICIENCY

(75) Inventors: Edward V. Quadros, Brooklyn, NY (US); Jeffrey M. Sequeira, Brooklyn, NY (US)

(73) Assignee: The Research Foundation of State University of New York, Albany, NY (US)

( * ) Notice: Subject to any disclaimer, the term of this patent is extended or adjusted under 35 U.S.C. 154(b) by 845 days.

(21) Appl. No.: 12/296,254

(22) PCT Filed: Apr. 5, 2007

(86) PCT No.: PCT/US2007/008674
§ 371 (c)(1),
(2), (4) Date: Aug. 24, 2009

(87) PCT Pub. No.: WO2007/117657
PCT Pub. Date: Oct. 18, 2007

(65) Prior Publication Data
US 2010/0061974 A1  Mar. 11, 2010

Related U.S. Application Data

(60) Provisional application No. 60/790,330, filed on Apr. 7, 2006.

(51) Int. Cl.
*G01N 33/53* (2006.01)
*G01N 33/567* (2006.01)

(52) U.S. Cl.
USPC ............. 435/7.1; 435/7.2; 435/7.21; 436/505

(58) Field of Classification Search
None
See application file for complete search history.

(56) References Cited

U.S. PATENT DOCUMENTS

| | | | |
|---|---|---|---|
| 4,429,008 A | 1/1984 | Martin | |
| 4,489,710 A | 12/1984 | Spitler | |
| 4,507,234 A | 3/1985 | Kato | |
| 4,569,789 A | 2/1986 | Blattler | |
| 4,625,014 A | 11/1986 | Senter | |
| 4,671,958 A | 6/1987 | Rodwell | |
| 4,673,562 A | 6/1987 | Davison | |
| 4,699,784 A | 10/1987 | Shih | |
| 4,735,792 A | 4/1988 | Srivastava | |
| 4,873,088 A | 10/1989 | Mayhew | |
| 5,229,275 A | 7/1993 | Goroff | |
| 5,545,807 A | 8/1996 | Surani | |
| 5,567,610 A | 10/1996 | Borrebaeck | |
| 5,589,369 A | 12/1996 | Seidman | |
| 5,591,317 A | 1/1997 | Pitts, Jr. | |
| 5,591,669 A | 1/1997 | Krimpenfort | |
| 5,688,504 A * | 11/1997 | Morgan, Jr. ................. | 424/141.1 |
| 5,739,287 A | 4/1998 | Wilbur | |
| 5,739,313 A | 4/1998 | Collins | |
| 5,747,470 A | 5/1998 | Becherer | |
| 5,770,429 A | 6/1998 | Lonberg | |
| 5,783,683 A | 7/1998 | Morrison | |
| 5,833,985 A | 11/1998 | Ball | |
| 5,837,243 A | 11/1998 | Deo | |
| 5,840,712 A | 11/1998 | Morgan, Jr. | |
| 5,840,880 A | 11/1998 | Morgan, Jr. | |
| 5,869,465 A | 2/1999 | Morgan, Jr. | |
| 5,922,845 A | 7/1999 | Deo | |
| 6,004,533 A | 12/1999 | Collins | |
| 6,071,517 A | 6/2000 | Fanger | |
| 6,083,926 A | 7/2000 | Morgan, Jr. | |
| 6,096,290 A | 8/2000 | Collins | |
| 6,096,311 A | 8/2000 | Fanger | |
| 6,111,166 A | 8/2000 | Van de Winkel | |
| 6,211,355 B1 | 4/2001 | Collins | |
| 6,270,765 B1 | 8/2001 | Deo | |
| 6,303,755 B1 | 10/2001 | Deo | |
| 6,365,116 B1 | 4/2002 | Barham | |
| 6,410,690 B1 | 6/2002 | Deo | |
| 6,613,305 B1 | 9/2003 | Collins | |
| 6,635,468 B2 * | 10/2003 | Ashkenazi et al. ......... | 435/252.3 |
| 6,682,928 B2 | 1/2004 | Keler | |
| 6,696,248 B1 | 2/2004 | Pluckthun et al. | |

(Continued)

FOREIGN PATENT DOCUMENTS

WO  WO 93/23557  11/1993
WO  WO 96/08515  3/1996

(Continued)

OTHER PUBLICATIONS

Ulleland, et al, (2002) Direct Assay for Cobalamin Bound to Transcobalamin (Holo-Transcobalamin) in Serum Clinical Chemistry 48:3, 526-532.*

Amagasaki T, et al., "Expression of transcobalamin II receptors by human leukemia K562 and HL-60 cells," Blood, 76, pp. 1380-1386; 1990.

Quadros, et al., "Characterization of the human placental membrane receptor for transcobalamin II-cobalamin," Arch Biochem Biophys, 308, pp. 192-199: 1994.

Bolognesi A, et al., "CD38 as a target ofiB4 mAb carrying saporin-S6: design of an immunotoxin for ex vivo depletion of hematological CD38+ neoplasia," J. Biol. Regul. Homeost Agents,19, pp. 145-152: 2005.

(Continued)

*Primary Examiner* — Daniel C Gamett

(57) ABSTRACT

The present invention provides the amino acid and polynucleotide sequences of the transcobalamin receptor, as well as modulators of the transcobalamin receptor. Accordingly, the present invention provides compositions and methods for the treatment and prevention of diseases and disorders associated with cobalamin deficiency, including compositions and methods that promote cobalamin uptake. In addition, the present invention provides compositions and methods for the detection, treatment, and prevention of diseases associated with deregulated cell growth, including, e.g., cancer and autoimmune disorders, including compositions and methods that inhibit cobalamin uptake.

23 Claims, 19 Drawing Sheets

(56) References Cited

U.S. PATENT DOCUMENTS

| | | | |
|---|---|---|---|
| 6,706,484 B1 | 3/2004 | Knappix et al. | |
| 6,753,138 B1 | 6/2004 | Schneider | |
| 6,806,363 B1 | 10/2004 | Collins | |
| 6,828,422 B1 | 12/2004 | Achim | |
| 6,838,073 B1 | 1/2005 | Collins | |
| 6,984,720 B1 | 1/2006 | Korman | |
| 7,049,135 B2 | 5/2006 | Rudert | |
| 7,141,233 B2 | 11/2006 | Collins | |
| 7,179,445 B2 | 2/2007 | Collins | |
| 7,416,728 B2 | 8/2008 | Morgan, Jr. | |
| 2003/0180312 A1 | 9/2003 | Ashkenazi | |
| 2004/0157291 A1 | 8/2004 | Frisch | |
| 2005/0169910 A1 | 8/2005 | Morgan | |
| 2006/0003334 A1 | 1/2006 | Achim | |
| 2006/0121563 A1 | 6/2006 | Prassler | |
| 2010/0239592 A1* | 9/2010 | Carmel et al. | 424/158.1 |

FOREIGN PATENT DOCUMENTS

| | | |
|---|---|---|
| WO | WO 97/14711 | 4/1997 |
| WO | WO 99/32619 | 7/1999 |
| WO | WO 00/37638 | 6/2000 |
| WO | WO 01/29058 | 4/2001 |
| WO | WO 01/68836 | 9/2001 |
| WO | WO 01/75164 | 10/2001 |
| WO | WO 01/92513 | 12/2001 |
| WO | WO 01/96584 | 12/2001 |
| WO | WO 02/44321 | 6/2002 |
| WO | WO 2004/048414 | 6/2004 |
| WO | WO 2007/117657 | 10/2007 |

OTHER PUBLICATIONS

Bose, et al., "Purification, membrane expression, and interactions of transcobalamin II receptor," Methods Enzymol, 281, pp. 281-289: 1997.
Caplen, N. et al., "Specific inhibition of gene expression by small double-stranded RNAs in invertebrate and vertebrate systems," Proc. Natl. Acad. Sci., 98, pp. 9746-9747: 2001.
Collins. et al., "Distribution of radiolabeled adenosylcobalamin in patients diagnosed with various malignancies," Mayo Clin. Proc. 75, pp. 568-580: 2000.
Cooper, et al., "Sequential mechanisms in the enhanced absorption of vitamin B12 by intrinsic factor in the rat." J Clin Invest., 39, pp. 199-214: 1960.
Daniels TR, et al., "Conjugation of an anti transferrin receptor IgG3-avidin fusion protein with biotinylated saporin results in significant enhancement of its cytotoxicity against malignant hematopoietic cells." Mol. Cancer Ther., 6, pp. 2995-3008: 2007.
Digirolamo PM, et al., "Transport of vitamin B12 into mouse leukemia cells," Arch. Biochem Biophys., 168, pp. 386-393: 1975.
Elshabir, S.M. et al., "Functional anatomy of siRNAs for mediating efficient RNAi in Drosophila melanogaster embryo lysate," EMBO J., 20:23, pp. 6877-6888: 2001.
Elshabir, et al., "Duplexes of 21-nucleotide RNAs mediate RNA interference in cultured mammalian cells," Nature, 411, pp. 494-498: 2001.
European Patent Publication No. 519,596, published Dec. 23, 1992.
Frankel AE, et al., "Prospects for immunotoxin therapy in cancer." Annu. Rev. Med. 37, pp. 125-142: 1986.
Friedman, et al. "A saturable high affinity binding site for transcobalamin II-vitamin B12 complexes in human placental membrane preparations," J. Clin. Invest. 59, pp. 51-58: 1977.
G. Russell-Jones, et al., "Vitamin-mediated targeting as a potential mechanism to increase drug uptake by tumors," J. Inorg. Biochem. 98, pp. 1625-1633: 2004.
Hall, et al., "Cyclic activity of the receptors of cobalamin bound to transcobalamin II." J Cell Physiol., 133, pp. 187-191: 1987.
Hall."The uptake of vitamin B12 by human lymphocytes and the relationships to the cell cycle." J. Lab. Clin. Med., 103, pp. 70-81: 1984.
Ippoliti R, et al., "A chimeric saporin-transferrin conjugate compared to ricin toxin: role of the carrier in intracellular transport and toxicity." Faseb J., 9, pp. 1220-1225: 1995.

Begly, et al., "Cobalamin metabolism in cultured human chorionic villus cells," J. Cell Physiol., 156, 43: 1993.
McGuire, "Anticancer antifolates: current status and future directions," Curr. Pharm. Des. 9, pp. 2593-2613: 2003.
J.R Bertino, "Cancer research: from folate antagonism to molecular targets," Best Pract. Res. Clin. Haematol., 22, pp. 577-582: 2009.
Jiang, Wenxia, et al., "Characterization of the promoter region of TCbIR/CD320 gene, the receptor for cellular uptake of transcobalamin-bound cobalamin," Gene, 466(1-2), pp. 49-55: 2010.
Li, L. et al., "Novel follicular dendritic cell molecule, 8D6, collaborates with CD44 in supporting lymphomagenesis by a Burkitt lymphoma cell line, L3055," Blood 104:3, pp. 815-821: 2004.
Li, L. et al., "Identification of a human follicular dendritic cell molecule that stimulates germinal center B cell growth," J. Exp. Med., 191, pp. 1077-1083: 2000.
Lia, Shao-Chiang, et al., "Down-regulation of transcobalamin receptor TCbIR/CD320 by siRNA inhibits cobalamin uptake and proliferation of cells in culture," Experimental Cell Research 317 1603-1607: 2011.
Lindemans J, et al., "Uptake of transcobalamin II-bound cobalamin by HL-60 cells: effects of differentiation induction." Exp. Cell Res., 184, pp. 449-460: 1989.
McLean GR, et al., "Antibodies to transcobalamin II block in vitro proliferation ofleukemic cells." Blood, 89, pp. 235-242: 1997.
Oldham RK., "Monoclonal antibodies in cancer therapy." J. Clin. Oncol., 1, pp. 582-590: 1983.
Paranchych W, et al., "Factors influencing the uptake of cyanocobalamin (vitamin B12) by Ehrlich ascites carcinoma cells." Biochim. Biophys. Acta., 60, pp. 393-403: 1962.
Polito L, et al., "The conjugate Rituximab/saporin-S6 completely inhibits clonogenic growth of CD20-expressing cells and produces a synergistic toxic effect with Fludarabine." Leukemia,18, pp. 1215-1222: 2004.
Qian ZM, et al., "Targeted drug delivery via the transferrin receptor—mediated endocytosis pathway," Pharmacol. Rev., 54, pp. 561-587: 2002.
Quadros, et al., "The protein and the gene encoding the receptor for the cellular uptake of transcobalamin-bound cobalamin," Blood, 113:1, pp. 186-192: 2009.
Quadros, et al., "The binding properties of the human receptor for the cellular uptake of vitamin BI2," Biochem. Biophys. Res. Commun., 327, pp. 1006-1010: 2005.
Quadros, et al., "Characterization of monoclonal antibodies to epitopes of human transcobalamin II," Biochem. Biophys. Res. Commun., 222, pp. 149-154: 1996.
Quadros, et al., "Advances in the understanding of cobalamin assimilation and metabolism," Br. J. Haematol .,148:, pp. 195-204: 2010.
Quadros, et al., "Functional human transcobalamin II isoproteins are secreted by insect cells using the baculovirus expression system," Blood, 81:5, pp. 1239-1245: 1993.
Quadros, et al., "Targeted delivery of saporin toxin by monoclonal antibody to the transcobalamin receptor, TCbIR/CD320," Mol. Cancer Ther., 11, pp. 3033-3040: 2010.
Battaglia-Hsu, et al., "Vitamin B12 deficiency reduces proliferation and promotes differentiation of neuroblastoma cells and up-regulates PP2A, proNGF, and TACE," Proc. Natl. Acad. Sci., 106, pp. 21930-21935: 2009.
Seligman, et al "Characterization of the receptor for transcobalamin II isolated from human placenta," J. Biol. Chem., 253:6, pp. 1766-1772: 1978.
Takahashi K, et al., "Receptor binding and internalization of immobilized transcobalamin II by mouse leukaemia cells," Nature, 288 pp. 713-715: 1980.
Ulleland, et al., "Direct assay for cobalamin bound to transcobalamin (Holotranscobalamin) in serum," Clinical Chemistry, 48:3, pp. 526-532: 2002.
Walker PR, et al., "Induction of apoptosis in neoplastic cells by depletion of vitamin B12," Cell Death Differ., 4, pp. 233-241: 1997.
Wickramasinghe SN., "Morphology, biology and biochemistry of cobalamin- and folate-deficient bone marrow cells," Baillieres Clin. Haematol, 8, pp. 441-459: 1995.

Zhang, X. et al., "The distinct roles of T cell-derived cytokines and a novel follicular dendritic cell-signaling molecule 8D6 in germinal center-B cell differentiation," J. Immunol., 167, pp. 49-56: 2001.
GenBank Accession No. BC000668, published Jul. 15, 2006.
GenBank Accession No. BC007083, published Jul. 15, 2006.
GenBank Accession No. CAG33455, published Oct. 16, 2008.
GenBank Accession No. AAH00668, published 07-15-006.
GenBank Accession No. CR457174, published Oct. 16, 2008.
GenBank Accession No. NM_016579, published Oct. 22, 2011.
GenBank Accession No. AAH07083, Published Jul. 15, 2006.
GenBank Accession No. NT_077812, published Jul. 29, 2011.
GenBank Accession No. NT 086894, published Aug. 20, 2004.
GenBank Accession No. NP 057663, published Oct. 22, 2011.
GenBank Gene ID: 51293, updated May 11, 2012.

* cited by examiner

FIG. 10

SEQUENCE ID NO. 4

```
                -3129   -2734                                    -1234          -455
                ShaBI   BsaBI                                    SplI           NheI                +1
                 |       |                                        |              |              ATG  3'
         5'  ────┼───────┼────────────────────────────────────────┼──────────────┼───────────────┤
             NADH                                                                                TCR
         dehydrogenase
```

-1022 CdxA    -1013 CdxA    -1010 Lyf-1      -1001 p300    -993 CdxA
-954 GATA-1                              -922 AML-1a                                         -896 CdxA
TAATTTTTGTATTTTTGGTAGAGACGGGAGTTTTACTATGTGTTGGCCAGGCTGGTGTTAGAACTCCTGACCT
CGTGATCCGCCCTGCCTCGGCCTCCCAAAGTGCTGGGGTTAACAGGCGTGAGCCAGCGCGCCGGCCAACTT
  -891 SRY          -884 AML-1a                                       -841 delta E
TTCTAACAAATGGGGTCTCACTGTCACCCACGCTGGAGTGCAGCCCCAAGTGATTCTCCCACCCTCAGCCT
                                                                                        -764 Spl
                                                                                     -762 MZF1
CCTGAGTAGCTGGGACTACAAATTAGAGCCCCAGCTAATTTTCTTTTTTCTTGAGGCGGCGG
         -820 Ik-2                     -737 GATA-1                               -693 STATx
GGACTTGCTGTGTTGCCCAGGCTGATCTCGAACTCCTGGGCTCAAGCGATCTGCCCGCCTCTGCTTCCCA
         -674 USF                            TaqI
                  -672 USF                                                            -619 S8
AAATGCTGGGATCACACGCGTGACCCACCGCGCCCGGCCCTTTATTATTAAATTTAATTAATTAATTGATT
         -601 RREB-1                                  -567 CdxA             -624 CDP CR
TCCTTTCCTTTTTCCCCCCCAAGCAAACCCGACTCCGAGAATGGACGTTTCATTTATTCATTTACTCACCA
-547 HNF-3b      -526 AP-1                                                           -418 XFD-3
AATGTTTACTAAGAGCCTACTATGAGTCAAGCACTATGTGTCAGATCCCTGAGAATAAAGCAGTGAGCAAC
                                                                                  -410 S8
                        -445 MZF-1                                               -345 Spl
AGAAGATCCCTGCCCTCCAGTAGCTAGCATTCTATGGGGACTCGGACAACAAACCAGAATAAGTAAATAA
                       NheI                                                          -281 c-Fs
                                                                             -283 c-Fs-
AATAAATTACCTGTCGGCGCCACAAAAGCAGTGGGATGAGGGAGGCGAAATGCCGAGTGCCTGAGGGGCGTG
                                                                                       -275 CdxA
GCTGCCATATTAAAGAAGATCACGAGGCAGTAACATTTGCAGCAGTCCTCATTTGGAACGGGAAATAATG
                                   -234 HSF2                                         -133 CdxA
CAAATGAACACCAACAAATTCCTTCCCATCCCCAGAAGTTTCTAACTTCAAGCGGGCTCCATACCTTTCA
         -185 MZF1      -176 MZF1                                               -142 CdxA
ACTGATCTGGTCACTGGGAAAGTGGGGACGGGCCCTCTAATTCTCTTTTCCCTGCTATTCTGACATTTAC
                                              ApaI              -12 MZF1            +1
GGTACGCGTAGCCGCGGGGGCCCCAGAACTCAGGGGGCTTGGGCCCCGCCCCAACCCCGCGCGTGCCGGTG
  -57 GATAI    SacII
CGCAGGGATAAGAGAGCGGTCTGGACAGCGCCGTCGGCCGCCGTGTGGGGACAGCGATGAGCGGCGGTT

SEQUENCE ID NO. 5

EAAASPLSTPTSAQAAGPSSGSCPPTKFQCRTSGLCVPLTWRCDRDLDCSDGSDEEECRIEPCTQK
GQCPPPGLPCPCTGVSDCSGGTDKKLRNCSRLACLAGELRCTLSDDCIPLTWRCDHPDCPDSS
DELGCGTNEILPEGDATTMGPPVTLESVPSVGNATSSSAGDQSGSPTAY

| Enzyme | Amino acid sequence (MW) |
|---|---|
| Arg-C | 1-31 (3007), 60-94 (3572), 121-163 (4418), 164-198 (3340) |
| Asp-N | 54-83 (3172), 1-43 (4324), 146-189 (4290) |
| Chymotrypsin 1 | 1-28 (2619), 42-119 (8393), 120-198 (7896) |
| Clostrapain | 1-31 (3007), 60-94 (3572), 164-198 (3340), 121-163 (4418) |
| Glu-C1 | 176-198 (2128), 106-133 (3151), 62-105 (4448), 2-55 (5504) |
| Glu-C2 | 158-175 (1875), 62-84 (2283), 2-44 (4310) |
| Lys-C | 67-91 (2374), 1-27 (2472), 28-66 (4497), 93-198 (10902) |
| Trypsin | 67-91 (2374), 1-27 (2472), 164-198 (3340), 121-163 (4418) |
| CNBr | 151-168 (1827), 169-198 (2821), 1-150 (15610) |

FIG. 13

TCblR.88 siRNA (SEQ ID NO:16)
GCGAU GAGGA GGAGU GCAGG AUUGA
UCAAU CCUGC ACUCC UCCUC AUCGC

TCblR.89 siRNA (SEQ ID NO:17)
GAACU GACAA GAAAC UGCGC AACUG
CAGUU GCGCA GUUUC UUGUC AGUUC

TCblR.90 siRNA (SEQ ID NO:18)
CGAGC UCGGC UGUGG AACCA AUGAG
CUCAU UGGUU CCACA GCCGA GCUCG

TRANSCOBALAMIN RECEPTOR POLYPEPTIDES, NUCLEIC ACIDS, AND MODULATORS THEREOF, AND RELATED METHODS OF USE IN MODULATING CELL GROWTH AND TREATING CANCER AND COBALAMIN DEFICIENCY

STATEMENT OF GOVERNMENT INTEREST

This invention was made in part with funds provided by the United States Government. Accordingly, the United States Government may have certain rights to this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is KYTO$_{13}$020$_{13}$01US$_{13}$SEQUENCE$_{13}$LISTING.txt. The text file is 14 KB, was created on Mar. 14, 2012, and is being submitted electronically via EFS-Web.

BACKGROUND OF THE INVENTION

1. Field of the Invention

The field of the present invention is transcobalamin receptor polypeptides and polynucleotides and the use of modulators thereof in the prevention, diagnosis, and treatment of cobalamin deficiency, tumors, and timmunological and inflammatory diseases and disorders.

2. Description of the Related Art

Vitamin B12 (cobalamin, Cbl) is a structurally complex water soluble molecule consisting of a planar corrin ring containing a central cobalt atom, a lower axial nucleotide (dimethylbenzimidazole) and an upper axial ligand which, in mammalian cells, is either a methyl, 5' deoxyadenosyl or hydroxo group. Methyl-Cbl functions in the transfer of the methyl group from $N^5$-methyltetrahydrofolate(methyl-FH$_4$) to homocysteine in the de novo synthesis of methionine catalyzed by the enzyme methionine synthase (MS). 5' deoxyadenosyl (ado-Cbl) is the cofactor for the rearrangement of methylmalonyl-CoA to succinyl-CoA, catalyzed by the enzyme methylmalonyl-CoA mutase (MMU) (14). The coenzyme function of hydroxo-Cbl is not known but it is an intermediary form in the interconversion of Cbl and is the substrate for the Cbl reductases in the neosynthesis of Cbl coenzymes.

The large size of Cbl (mol wt of CN-Cbl=1355), the complex three dimensional structure, and its hydrophilic properties prevent passive diffusion of this vitamin through cell membranes. A complex process has evolved in mammals requiring two carrier proteins and two membrane receptors for the assimilation of Cbl from the intestinal tract to its final destination in the tissue cells. Cbl released from food binds preferentially to a salivary R-protein favored by the acid pH in the stomach, and subsequently transfers to intrinsic factor (IF) at neutral pH in the jejunum as R-protein is digested by pancreatic trypsin. The IF-Cbl complex is carried to the distal ileum where it binds to specific receptors on the microvillous membrane. Recent reports have identified the IF receptor as cubilin, a 460 kDa membrane-associated protein that was purified from kidney and has been identified in the yolk sac and in the ileum. This protein binds IF-Cbl in the presence of $Ca^{++}$ and interacts with amnionless a transmembrane protein involved in the endocytosis of cubilin bound IF-Cbl. The absorbed Cbl is released into the circulation bound to transcobalamin (TC), a Cbl binding plasma protein secreted by the vascular endothelium. Megalin, a multi-ligand binding protein expressed in the epithelial cells is involved in the reabsorption of TC in the kidney. The cDNA encoding cubilin has been cloned and the deduced amino acid sequence indicates that cubilin also belongs to the class of multi-ligand binding proteins.

The absorption of Cbl from the ileum is essential for maintaining Cbl homeostasis. Any perturbation of this process will ultimately lead to intracellular Cbl deficiency. Because of the fundamental role of Cbl in essential metabolic reactions, one of which is coupled to folate metabolism and, as a consequence, to nucleic acid synthesis, Cbl deficiency will lead to abnormal cell division and differentiation as observed in megaloblatic anemia resulting from both Cbl and folate deficiency. The neurological complications of Cbl deficiency are known to cause irreversible damage to the central as well as the peripheral nervous system (25).

Excluding dietary deficiency and secondary causes of malabsorption, such as tropical sprue and parasitic infestation, the primary causes of Cbl deficiency are, lack of IF as observed in patients with pernicious anemia, impaired release of Cbl from food, congenital IF deficiency and congenital TC deficiency. Cbl malabsorption and proteinuria characterize another disorder known as Imersiund-Grasbeck syndrome in which absorption of IF-Cbl in the distal ileum is affected by a defect in internalizing the receptor bound IF-Cbl.

The essential process of tissue distribution and cellular uptake of Cbl is mediated by TC, a plasma protein, and a membrane receptor (TCblR) for TC-Cbl that binds and internalizes TC-Cbl by endocytosis. TC is also required for the translocation of Cbl absorbed in the distal ileum and this function is impaired in congenital TC deficiency. The normal concentration of this protein in plasma is 0.4-1.2 pM, of which, approximately 10-30% is saturated with Cbl under conditions of normal Cbl homeostasis. Elevated levels of TC have been reported in certain autoimmune and myeloproliferative disorders. TC has been purified from human plasma and the cDNA encoding this protein has been isolated from endothelial cDNA libraries.

Reports that identified TC and TC mRNA in various tissues did not identify the specific cell in these tissues as the source of the protein. In addition, studies showing TC synthesis by liver cells, macrophages, fibroblasts, lymphocytes and ileal mucosa in culture do not provide information about the source of TC in vivo. Though all these cells may synthesize TC in culture, the finding that human umbilical vein endothelial cells (HUVEC) synthesize significantly more of this protein than other cells, and that the umbilical vein perfused ex vivo synthesizes TC, provides evidence that the vascular endothelium is the likely source of plasma TC. The extensive endothelial surface provides the capacity to maintain the circulating level of TC that has a relatively short half life of 60-120 min.

The Transcobalamin Receptor (TCblR)

The physiological process of Cbl uptake in cells requires a specific receptor on the cell surface that binds holo-TC with high affinity. Cbl binding proteins in serum have been identified and the role of TC in the cellular uptake of Cbl has been well characterized. Information on the cellular uptake of Cbl was derived initially from direct binding of Cbl to a membrane receptor in prokaryotes and from a more complex process in mammalian cells whereby a membrane receptor specifically binds TC-Cbl and internalizes the complex. The process is biphasic with an initial $Ca^{++}$ dependent and temperature-independent binding of TC-Cbl to the receptor, followed by a slower second temperature-dependent step that translocates the vitamin into the cell and requires metabolic energy. The TC mediated uptake of Cbl has been identified in all mammalian cells studied and appears to be the only system for delivering Cbl into cells except for the liver, where uptake of Cbl bound to haptocorrin, another Cbl binding protein in the blood, occurs via the asialoglycoprotein receptor.

Studies in human skin fibroblasts established receptor-mediated endocytosis of TC-Cbl and the subsequent lysosomal degradation of TC to release the Cbl. Later studies showed that the receptors are expressed predominantly on membrane microvilli and the internalization of TC-Cbl occurs via clathrin-coated pits. Between 2000-6000 TC-Cbl receptors per cell are expressed during the proliferative phase of the cell and are down regulated to less than 300 receptors in non-dividing and fully differentiated cells. The increased requirement for intracellular Cbl during the early phase of cellular replication induces higher receptor expression in actively dividing cells that can account for a 10-30 fold increase in receptors in these cells. This expression of the TC receptor provides a unique target to selectively block Cbl uptake in cells that require the vitamin the most, i.e., actively dividing cells and to deliver antimetabolite analogs and Cbl-drug conjugates preferentially to rapidly proliferating cells.

Information on the structure of the TCblR protein is scant and results from different laboratories have not been consistent. The first attempt to solubilize TCblR was reported by Friedman et al. (*J. Clin. Invest.* 59:51-8, 1977), using placental membranes as the source of TCblR. They were able to show specific $Ca^{++}$ dependent binding of TC-Cbl to placental membranes and to a Triton-soluble fraction of the membranes. Seligman and Allen in 1978 (*J. Biol. Chem.* 253:1766-72, 1978) reported the purification of the soluble receptor using conventional protein purification techniques coupled with affinity purification on a Sepharose-Cbl-rabbit TC column. They identified a major 460 kDa and a minor 40 kDa receptor by gel filtration chromatography and a 50 kDa protein by sucrose density gradient centrifugation. A major protein staining region corresponding to TC-Cbl binding activity in the gel was identified by non-denaturing PAGE but SDS-PAGE of the final product which can provide a better indication of purity and size was not reported. In their study, functional receptor activity was monitored using a mini DEAE ion exchange column to separate receptor bound TC-Cbl from free TC-Cbl. This method under the best conditions, only provides partial separation of the two fractions and an over estimate of TCblR activity (PI, personal observations) and therefore, the 2.9 n moles of TCblR activity recovered from 6 placentas is likely to be an over estimate. Based on the specific activity of the protein reported, and protein content, at best the final product would be 60% pure and therefore, amino acid and carbohydrate analyses reported cannot be accurate. Bose and Seetharam (*Methods Enzymol.* 281:281-9, 1997) used the procedure of Seligman and Allen with minor modifications to purified TCblR and, based on SDS-PAGE under reducing and non-reducing conditions, concluded that the purified TCblR migrates as a 72 kDa or 62 kDa protein respectively. They did not provide any data on the yield of functional activity, purity or specific activity of the final product. Their studies indicated that TCblR may exist as a non-covalent dimer in the lipid bilayer of the plasma membrane. They have not identified the primary structure and the gene encoding this protein. It is important to note that their results differed from earlier reports.

Studies to characterize TCblR from human placenta (*Arch. Biochem. Biophys.* 308:192-9, 1994) showed that the receptor is a 58 kDa protein with a core polypeptide of 41 kDa. Carbohydrate accounts for the remainder of the protein mass and is comprised of sialic acid (47%), and N-linked (24%) and O-linked (29%) sugars. These results were derived from enzymatic digestion of TCblR crosslinked to TC and changes in the molecular weight of the complex on SDS-PAGE. Taking into account all published data, complete characterization of the structure of TCblR had remained unresolved and the gene encoding this important receptor protein, unidentified.

Cbl in the Central Nervous System (CNS)

The neuropathological changes in the peripheral and central nervous system and the consequent functional abnormalities in Cbl deficiency provide compelling evidence in support of a role for this vitamin in maintaining a normal nervous system. However, clear evidence of Cbl deficiency in AD and other dementias is lacking. Among the biochemical and morphological changes observed in these disorders, hypomethylation of cellular components and apoptotic cell death have been observed in the brain. Such pathological changes can be caused by both Cbl and/or folate deficiency. The metabolic pathways involving these two vitamins have not been adequately characterized in brain tissue. The concentration of Cbl in the adult brain is ~40-130 pg/mg tissue, a level similar to that in the spleen and kidney. The concentration of Cbl in most tissues including the brain is lower at birth and increases with age. In the fetal brain and liver, the Cbl requiring enzyme MS is highest during early embryogenesis and decreases as the fetus develops. The level of MeCbl in this tissue parallels the activity of the enzyme. Very little is known about TC and TCblR in the brain, and nothing is known about the expression of these essential proteins in aging and various brain disorders. The binding of TC-Cbl to brain tissue has been measured and appears to be higher in membranes prepared from the brain cortex than from the spinal cord. In addition, uptake of TC-Cbl has been reported in glial cells in culture.

TC is the major Cbl binding protein in cerebrospinal fluid (CSF) and the reported synthesis of this protein by brain cells would support the notion that the TC required for Cbl uptake may be synthesized in situ in the brain tissue. A role for Cbl and folate deficiency in various dementias could not be established by measuring total Cbl and folate levels in serum and CSF because they have provided ambiguous results. However, studies designed to evaluate methylation in the brain have identified altered methylation ratio of S-adenosylmethionine to S-adenosylhomocysteine (SAM/SAH) in the CSF. Hypomethylation in brain from Cbl deficient animals and in brain tissue obtained at autopsy from individuals with AD and dementia has been reported. These studies indicate that defects in the transmethylation pathways involving Cbl and folate may contribute to the pathogenesis of AD and dementias. In the absence of dietary deficiency, decreased cellular uptake may cause intracellular deficiency.

The TC-TCblR Pathway in Cancer Therapy

The recent advances in monoclonal antibody technology such as engineering antibody to eliminate most of the immunogenic mouse protein component, or producing human antibody in a transgenic mouse, have significantly reduced some of the adverse effects of antibody therapy and have advanced the use of monoclonals to target specific antigens in cancer and autoimmune diseases. Preventing neovascularization of tumors with anti angiogenesis therapy, or by blocking the cellular uptake or intracellular metabolism of specific nutrients, are experimental approaches to suppress neoplastic growth. Because of the essential role of Cbl in recycling folate and thereby providing folate for DNA synthesis and maintaining intracellular SAM levels for methylation reactions, depleting intracellular Cbl would inhibit cellular replication. In humans, Cbl deficiency due to malabsorption or poor dietary intake takes several years to present clinically because of the large liver stores of Cbl. Infants born with congenital TC deficiency develop normally in the uterus because of the maternal supply of TC-Cbl. However they develop Cbl deficiency rapidly, i.e., after several months following birth because they lack TC. It has been difficult to produce an animal model of Cbl deficiency by Cbl depletion because of hepatic stores and contribution to the Cbl pool by the gut microflora. Some success was reported with the African fruit bats maintained in captivity for long periods on a Cbl deficient diet. It has been even more difficult to produce Cbl deficiency in vitro in cultured cells because of the TC-Cbl contribution from serum or serum factor supplements required for in vitro cultures. However, a carefully controlled study has shown that all cells have an absolute requirement for Cbl, and fail to replicate when intracellular Cbl decreases below a critical concentration. Evidence in support of the effects of Cbl deficiency on cell replication is also available from studies in which nitrous oxide ($N_2O$) was administered for prolonged periods either to patients with acute leukemia to control their leukemia, or to patients following major surgery to alleviate their pain and these patients developed megaloblastic anemia akin to that seen in Cbl deficiency. $N_2O$ affects the reduced state of the cobalt in the Cbl molecule and this in turn affects the synthesis of methyl-Cbl the cofactor for the enzyme MS.

The strategy to inhibit cellular uptake of Cbl can utilize epitope specific monoclonal antibodies to the Cbl transporter, TC in blood and to the plasma membrane receptor, TCblR that facilitates the cellular uptake of TC-Cbl. mAbs to human TC have been generated (see Morgan et al., PCT Patent Publication No. WO 96/08515, published Mar. 21, 1996). Characterization of these murine mAbs has provided three distinct types of mAb, i.e., mAb that prevents the uptake of TC-Cbl by TCblR (receptor blocking), mAb that prevents the binding of Cbl to apo TC (Cbl blocking) and mAb that does not compromise the receptor binding and Cbl binding functions of TC (binding mAb). The receptor blocking and the Cbl blocking anti TC mAbs, either alone or in combination, could be used to prevent cellular uptake of Cbl. A similar effect could be produced with a mAb to TCblR that blocks the binding of TC-Cbl. These mAbs could serve as a biological modulator to arrest cellular proliferation by selectively depleting an essential nutrient. Studies with anti-TC mAbs show that these mAbs block Cbl uptake and inhibit cellular replication in vitro. The TC-Cbl binding mAb when coupled to drugs, toxins or radionuclides, could deliver these compounds to tumor cells via the TC-TCblR pathway. TCblR expression is increased during the proliferative phase of the cell cycle and in cancers, a large proportion of cells are actively dividing and therefore, this pathway could be exploited to deliver mAb-drug or Cbl-drug conjugates to replicating cells. Radioactive molecules or fluorescent compounds coupled to Cbl have been used to locate tumor mass by imaging techniques because more of these compounds accumulate in tumor cells compared to the surrounding tissue.

Clearly, there is a need in the art for additional methods of treating and preventing cobalamin deficiency, as well as cancer and other diseases related to cell proliferation, immune responses, and inflammation. The present invention meets this long-felt need by providing TCblR polypeptides and polynucleotides, which are useful in identifying modulators of CBL uptake and TCblR activity. In addition, the present invention provides novel TCblR modulators, including siRNA and antibodies specific for TCblR, and methods of making the same, which are used in therapeutic compositions to modulate Cbl uptake and treat cancer and other diseases associated with cell proliferation, immune response, and inflammation.

BRIEF SUMMARY OF THE INVENTION

The present invention provides novel composition and methods useful in regulating cellular uptake of cobalamin and cell growth, including modulators of transcobalamin receptor expression and/or activity. Accordingly, the compositions and methods of the present invention are also useful to treat and/or prevent diseases and disorders associated with transcobalamin uptake, and to identify tumor cells and target therapeutic agents to tumor cells.

In one embodiment, the present invention provides a method of inhibiting cobalamin uptake by a cell, comprising contacting a cell with an inhibitor of a transcobalamin receptor. In one embodiment, the transcobalamin receptor has an amino acid sequence set forth in SEQ ID NO:1. In one embodiment, the inhibitor inhibits expression of the transcobalamin receptor, and in particular embodiments, the inhibitor is an antisense RNA, a ribozyme, or an RNAi molecule. In a second embodiment, the inhibitor inhibits an activity of the transcobalamin receptor, and in particular embodiments, the inhibitor is a polypeptide, a peptide, a small organic compound, or an antibody. In various embodiments, the antibody is a monoclonal antibody or a humanized antibody. In one embodiment, the inhibitor interferes with the binding of trancobalamin to the transcobalamin receptor.

In a further embodiment, the present invention provides a method of delivering a therapeutic agent to a tumor cell, comprising contacting a tumor cell with a therapeutic agent coupled to an antibody that specifically binds a transcobalamin receptor. In one embodiment, the transcobalamin receptor has an amino acid sequence set forth in SEQ ID NO:1. In particular embodiments, the antibody is a monoclonal antibody or a humanized antibody.

A related embodiment of the present invention includes a method of inducing apoptosis in a cell, comprising contacting a cell with an antibody to a transcobalamin receptor. In one embodiment, the transcobalamin receptor has an amino acid sequence set forth in SEQ ID NO:1, wherein said antibody inhibits uptake of cobalamin by the cell. In particular embodiments, the antibody is a monoclonal antibody or a humanized antibody.

In yet another related embodiment, the present invention provides a method of enhancing cobalamin uptake by a cell, comprising introducing into a cell a polynucleotide comprising a sequence encoding a transcobalamin receptor. In one embodiment, the transcobalamin receptor has an amino acid sequence set forth in SEQ ID NO:1 or a fragment thereof. In one embodiment, the polynucleotide further comprises a promoter sequence operatively linked to the sequence encoding the transcobalamin receptor. In a particular embodiment, the polynucleotide is an expression vector. In another particular embodiment, the polynucleotide is a targeting vector or a homologous recombination construct.

In another related embodiment, the invention includes a method of identifying a modulator of cobalamin uptake into a cell, comprising: (a) contacting a transcobalamin receptor, or a fragment thereof, with transcobalamin, or a fragment thereof, in the presence of a candidate modulator; (b) determining an amount of the transcobalamin bound to the transcobalamin receptor; and (c) comparing the amount of bound transcobalamin to an amount bound in the absence of the candidate modulator, wherein a decreased or increased amount of bound transcobalamin indicates that the candidate modulator is a modulator of cobalamin uptake into a cell. In one embodiment, the transcobalamin receptor has an amino acid sequence set forth in SEQ ID NO:1. In particular embodiments, the transcobalamin receptor or fragment thereof is recombinantly produced. In particular embodiments, the modulator is an antibody or a small organic compound.

In a related embodiment, the present invention includes a method of identifying a modulator of cobalamin uptake into a cell, comprising: (a) contacting a cell comprising an exogenous polynucleotide comprising a sequence encoding a transcobalamin receptor with transcobalamin in the presence of a candidate modulator; (b) determining an amount of the transcobalamin taken up by the cell; and (c) comparing the amount of transcobalamin taken up by the cell to an amount taken up in the absence of the candidate modulator, wherein a decreased or increased amount of transcobalamin taken up by the cell indicates that the candidate modulator is a modulator of cobalamin uptake into a cell. In one embodiment, the transcobalamin receptor has an amino acid sequence set forth in SEQ ID NO:1. In particular embodiment, the modulator is an antibody or a small organic compound.

In one embodiment, the present invention includes a method of identifying a modulator of cobalamin uptake into a cell, comprising: contacting an isolated recombinantly-produced transcobalamin receptor polypeptide or a fragment thereof with transcobalamin, or a fragment thereof, in the presence of a candidate modulator; determining an amount of the transcobalamin bound to the transcobalamin receptor; and comparing the amount of bound transcobalamin to an amount bound in the absence of the antibody, wherein a decreased or increased amount of bound transcobalamin in the presence of the candidate modulator as compared to in the absence of the candidate modulator indicates that the candidate modulator is a modulator of cobalamin uptake into a cell.

In a related embodiment, the present invention provides a method of identifying a modulator of cobalamin uptake into a cell, comprising: contacting a cell comprising an exogenous polynucleotide that encodes a transcobalamin receptor polypeptide or a fragment thereof with transcobalamin in the presence of a candidate modulator; determining an amount of the transcobalamin taken up by the cell; and comparing the amount of transcobalamin taken up by the cell to an amount taken up in the absence of the candidate modulator, wherein a decreased or increased amount of transcobalamin taken up by the cell in the presence of the candidate modulator as compared to in the absence of the candidate modulator indicates that the candidate modulator is a modulator of cobalamin uptake into a cell.

In particular embodiments of the methods of the present invention, the candidate modulator is an antibody, an aptamer, an siRNA, or a fragment of a transcobalamin receptor.

In a further related embodiments, the present invention provides a method of identifying a human antibody that inhibits cobalamin uptake into a cell, comprising: contacting an isolated recombinantly-produced transcobalamin receptor polypeptide or a fragment thereof with transcobalamin, or a fragment thereof, in the presence of a human antibody specific for a transcobalamin receptor; determining an amount of the transcobalamin bound to the transcobalamin receptor; and comparing the amount of bound transcobalamin to an amount bound in the absence of the antibody, wherein a decreased amount of bound transcobalamin in the presence of the antibody indicates that the antibody inhibits cobalamin uptake into a cell.

In another embodiments, the present invention includes a method of identifying a human antibody that inhibits cobalamin uptake into a cell, comprising: contacting a cell expressing an exogenous transcobalamin receptor polypeptide or fragment thereof with transcobalamin in the presence of a human antibody that specifically binds the transcobalamin receptor polypeptide; determining an amount of the transcobalamin taken up by the cell; and comparing the amount of transcobalamin taken up by the cell to an amount taken up in the absence of the antibody, wherein a decreased amount of transcobalamin taken up by the cell indicates that the antibody is an inhibitor of cobalamin uptake into a cell.

The present invention also include, in a related embodiment, a method of producing a human antibody that inhibits cobalamin uptake into a cell, comprising producing a human antibody specific for a transcobalamin receptor by immunizing a transgenic non-human animal that expresses human antibody polypeptides with a purified recombinantly-produced transcobalamin receptor polypeptide or an immunogenic portion thereof, wherein said recombinantly-produced transcobalamin polypeptide is purified from a cell comprising an exogenous polynucleotide encoding a transcobalamin receptor polypeptide or a fragment thereof, operatively linked to a promoter sequence, such that the cell expresses the recombinantly-produced transcobalamin receptor polypeptide.

Various embodiments of the methods of the present invention may further include demonstrating that an antibody inhibits cobalamin uptake into a cell by: contacting an isolated recombinantly expressed transcobalamin receptor polypeptide, or a fragment thereof, with transcobalamin, or a fragment thereof, in the presence of the antibody; determining an amount of the transcobalamin bound to the transcobalamin receptor polypeptide; and comparing the amount of bound transcobalamin to an amount bound in the absence of the antibody, wherein a decreased amount of bound transcobalamin indicates that the antibody inhibits cobalamin uptake into a cell.

Other embodiments of the methods of the present invention may further include demonstrating that an antibody inhibits cobalamin uptake into a cell by: contacting a cell expressing an exogenous transcobalamin receptor polypeptide with transcobalamin in the presence of a candidate modulator; determining an amount of the transcobalamin taken up by the cell; and comparing the amount transcobalamin taken up by the cell to an amount taken up in the absence of the antibody, wherein a decreased amount of transcobalamin taken up by the cell indicates that the antibody is an inhibitor of cobalamin uptake into a cell.

In particular embodiments of methods of the present invention, the transcobalamin receptor polypeptide or fragment thereof comprises an amino acid sequence set forth in SEQ ID NO:1 or a fragment thereof. In a further related embodiment, the present invention includes a method of visualizing a tumor in a patient, comprising introducing an agent that specifically binds to TCblR to a patient, wherein said agent is coupled to a detectable label, and determining the location in the patient of the detectable label after a time sufficient to permit the detectable label to specifically bind to tumor cells, thereby visualizing a tumor in the patient. In particular embodiments, the detectable label is a radioactive, fluorescent, or chemiluminescent label.

In additional embodiments, the present invention provides a method of inhibiting cobalamin uptake by a cell, comprising contacting a cell with an effective amount of a double-stranded oligonucleotide 8 to 30 nucleotides in length that is targeted to a polynucleotide encoding a transcobalamin receptor, wherein said oligonucleotide inhibits expression of a transcobalamin receptor. In certain embodiments, the oligonucleotide comprises a portion of a sequence set forth in any one of SEQ ID NOs:2 or 3.

In particular embodiments, the oligonucleotide comprises a sequence set forth in any one of SEQ ID NOs:6-18.

In a related embodiment, the present invention includes a double-stranded ribonucleic acid (dsRNA) for inhibiting the expression of a transcobalamin receptor gene in a cell, wherein said dsRNA comprises at least two sequences that are complementary to each other and wherein a sense strand comprises a first sequence and an antisense strand comprises a second sequence comprising a region of complementarity that is substantially complementary to at least a part of a mRNA encoding a transcobalamin receptor, and wherein said region of complementarity is less than 30 nucleotides in length and wherein said dsRNA, upon contact with a cell expressing said transcobalamin receptor, inhibits expression of said transcobalamin receptor by at least 20%. In other related embodiments, the dsRNA inhibits expression of said transcobalamin receptor by at least 25%, at least 30%, at least 40%, at least 50%, at least 60%, at least 70%, at least 80%, or at least 90%. In one embodiment, the sense strand comprises a portion of a sequence set forth in any one of SEQ ID NOs:2 or 3.

In a further embodiment, the present invention includes a method of treating or preventing a tumor, a neurological disease, an immune-related disease, inflammation, or a neurological disease in a patient, comprising administering to said patient a dsRNA of the present invention.

In another related embodiment, the present invention includes a method of enhancing cobalamin uptake by a cell, comprising introducing into a cell a polynucleotide comprising a sequence encoding a transcobalamin receptor or a fragment thereof. In one embodiment, said polynucleotide further comprises a promoter sequence operatively linked to the sequence encoding the transcobalamin receptor or fragment thereof. In particular embodiments, the sequence encoding a transcobalamin receptor or fragment thereof comprises the sequence set forth in any one of SEQ ID NOs:2 and 3, or a fragment thereof.

In a further related embodiment, the present invention includes a method of inhibiting cobalamin uptake by a cell, comprising contacting a cell with an effective amount of a recombinantly produced polypeptide comprising an extracellular domain of a transcobalamin receptor, wherein said recombinantly produced polypeptide binds transcobalamin. In one embodiment, said transcobalamin receptor has a sequence set forth in SEQ ID NO:1.

In a related embodiment, the present invention includes a method of treating or preventing a tumor, a neurological disease, an immune-related disease, inflammation, or a neurological disease in a patient, comprising administering to said patient an effective amount of a recombinantly produced polypeptide comprising an extracellular domain of a transcobalamin receptor, wherein said recombinantly produced polypeptide binds transcobalamin.

BRIEF DESCRIPTION OF THE SEVERAL VIEWS OF THE DRAWING(S)

FIGS. 1A-1C are photographs of silver stained 8% SOS-PAGE gels, depicting each stage of the three-stage purification procedure. FIG. 1A shows three separate preparations of TCblR (lanes 1-3) resulting from the first affinity purification, with the far left lane showing molecular weight markers. FIG. 1B shows the results after reapplying the eluted TCblR to the anti-TC affinity matrix or to the TC-Cbl-Emphase matrix during the second phase of purification. Lane 1 shows proteins that adhered to the affinity matrix, and lane 2 shows proteins that did not adhere to the affinity matrix. FIG. 1C shows the proteins recovered after application to a ConA agarose matrix during the third stage of affinity purification. Proteins corresponding to transcobalamin (TC) and transcobalamin receptor (TCblR) are indicated by arrows.

FIG. 2 shows an autoradiograph of iodinated proteins dissociated from the anti-TC affinity matrix by photo-dissociation. Lane 1 shows the results of photo-dissociation in the presence of 1 mM OTT, and lane 2 shows the results in the absence of DTT. Proteins corresponding to transcobalamin (TC) and transcobalamin receptor (TCblR) are indicated by arrows.

FIG. 3 shows the amino acid sequence of the full length transcobalamin receptor (TCblR; SEQ ID NO:1). Regions corresponding to putative functional domains, N-glycosylatino sites, phosphorylation, and myristoylation sites are indicated. Regions corresponding to the four peptides identified upon sequencing purified TCblR are underlined.

Figure 7:
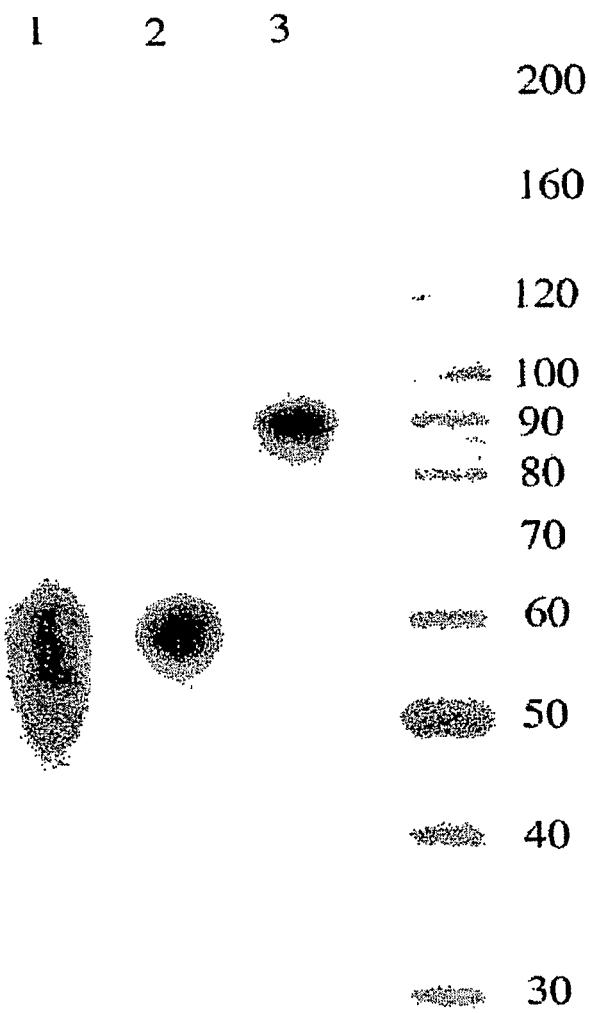

FIG. 7 is a photograph of a western blot of TCblR separated on a reducing 8% SOS-PAGE gel using polyclonal antiserum generated against the extracellular domain of TCblR followed by peroxidase conjugated secondary antibody. Lane 1 shows TCblR from the first affinity purification; Lane 2 shows the cleaved recombinant extracellular domain; and Lane 3 shows the fusion protein with the human Fc region. Molecular weights are shown on the right.

Figure 8:
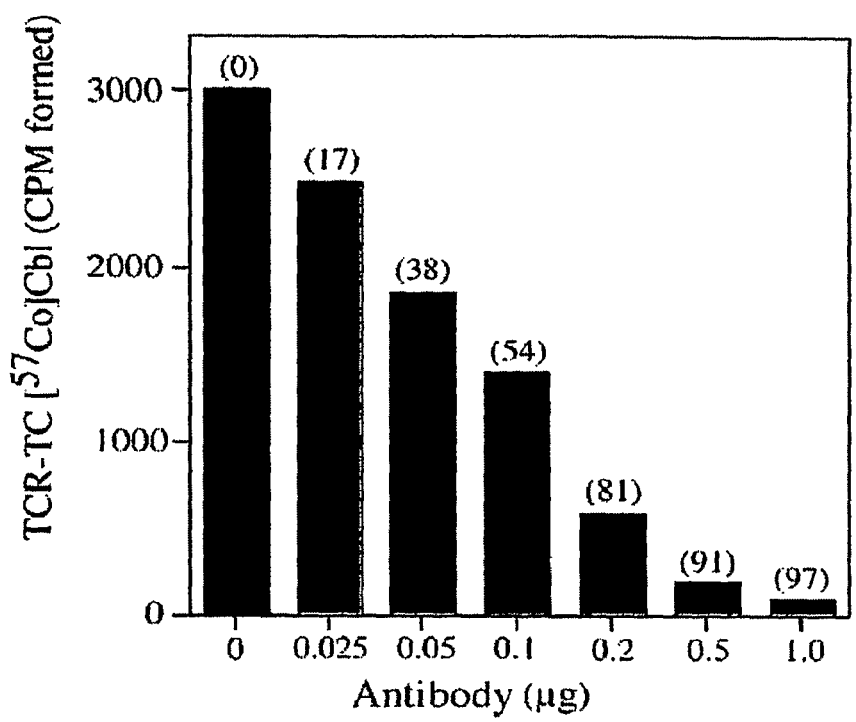

FIG. 8 is a graph showing the binding of TC-Cbl to purified TCblR in the presence of increasing amounts of anti-TCblR polyclonal antiserum. The vertical bars represent the amount of TCblR-TC-Cbl complex formed as determined by the ConA binding assay. The amount of antibody is indicated below each bar, and the percent blocking is shown above each bar.

Figure 9:
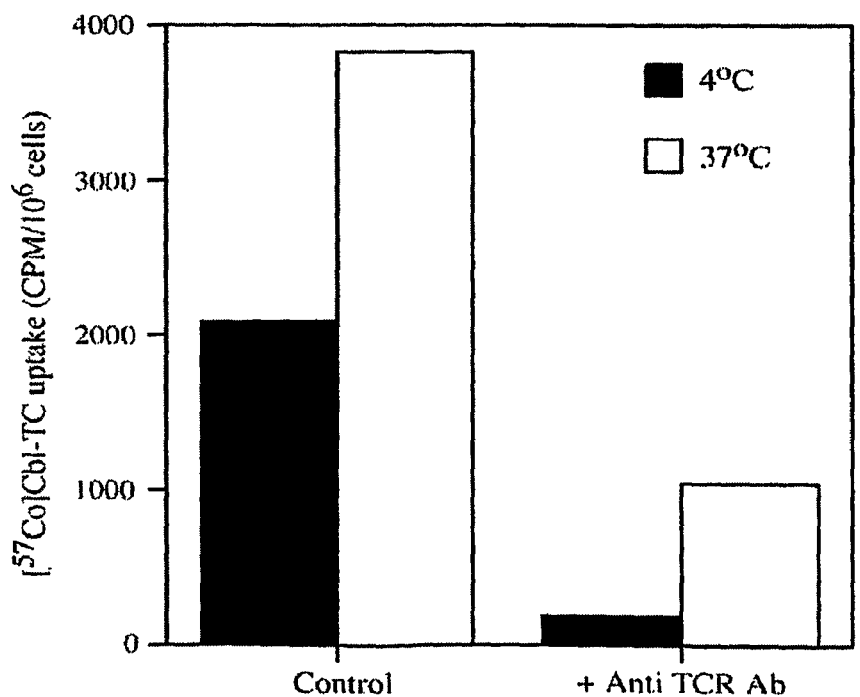

FIG. 9 is a graph showing the binding of TC-Cbl to K562 cells in the absence (control) or presence of anti-TCblR polyclonal antiserum (anti TCblR ab). The black boxes depict the results following incubation with the antibody for 1 hr at 4° C., and the white boxes depict the results following incubation with the antibody for 1 hr at 37° C.

FIG. 10 shows the sequence of the 5' promoter region of the TCblR gene (SEQ ID NO:4) with putative transcription factor binding sites and unique restriction enzyme sited indicated.

FIGS. 11A and 11B are graphs showing the uptake of radiolabeled Cbl-TC by K562 (FIG. 11A) and HL-60 (FIG. 11B) cells in culture over a 150 hour time course at 37° C. Uptake of [$^{57}$Co]Cbl-TC was determined at 37° C. for one hour. The cell density over time and the amount of associated CBL-TC over time are both indicated.

Figure 12:
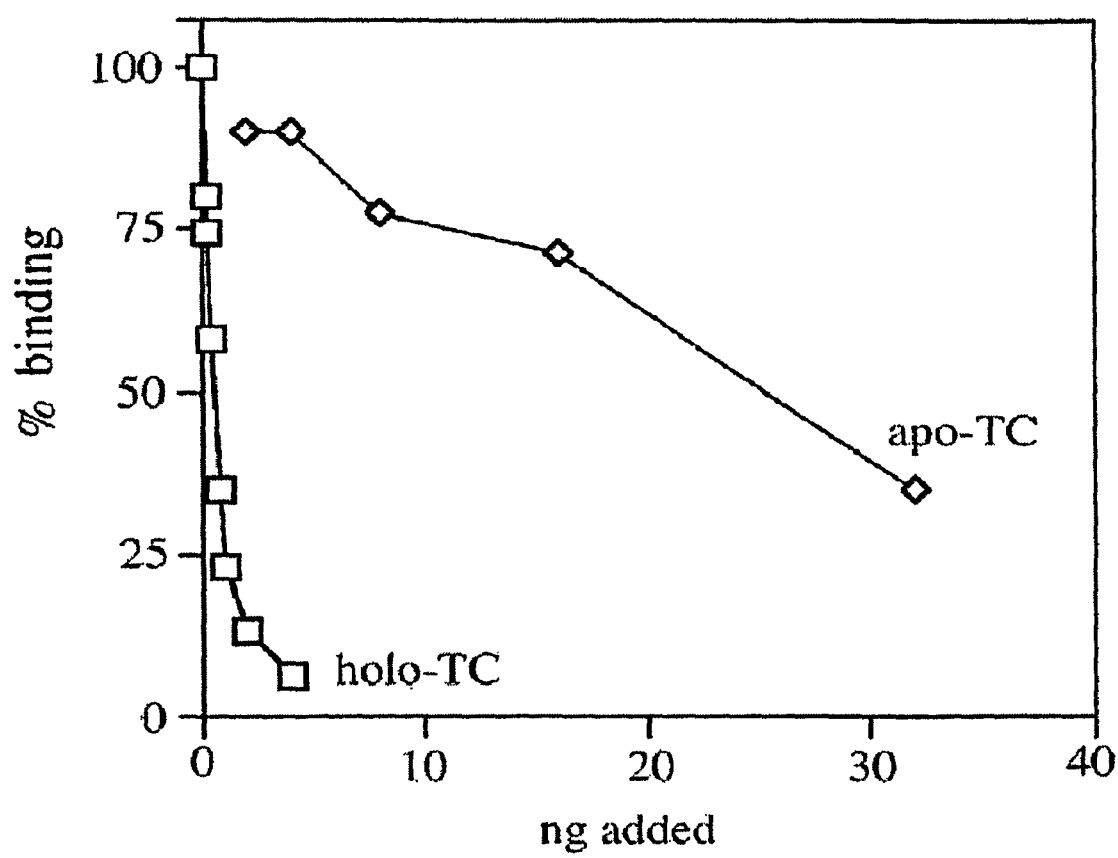

FIG. 12 is a graph depicting the binding of radiolabeled Cbl-TC to purified TCblR in the presence of unlabeled apo-TC or holo-TC. The amount of holo-TC or apo-TC present is shown on the x-axis, and the % binding is shown on the y-axis.

FIG. 13 is a table showing the amino acid sequence of the extracellular domain of TCblR (SEQ ID NO:5) and peptide fragments generated using endopeptidases and CNBr.

Figure 14:
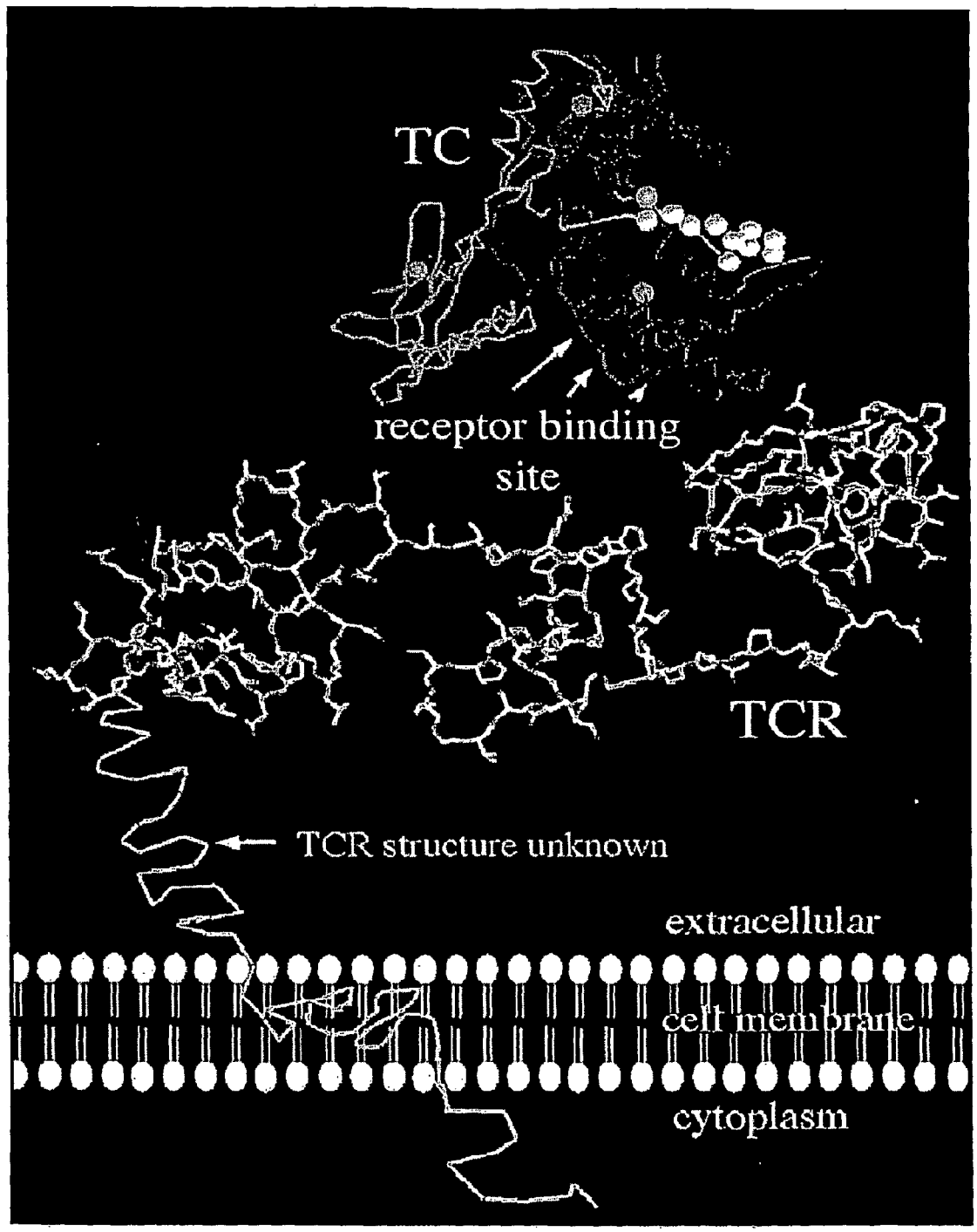

FIG. 14 is a structural representation of human TC and the deduced structure of the extracellular domain of TCblR with the region of TC believed to be involved in binding to TCblR indicated.

Figure 15A:
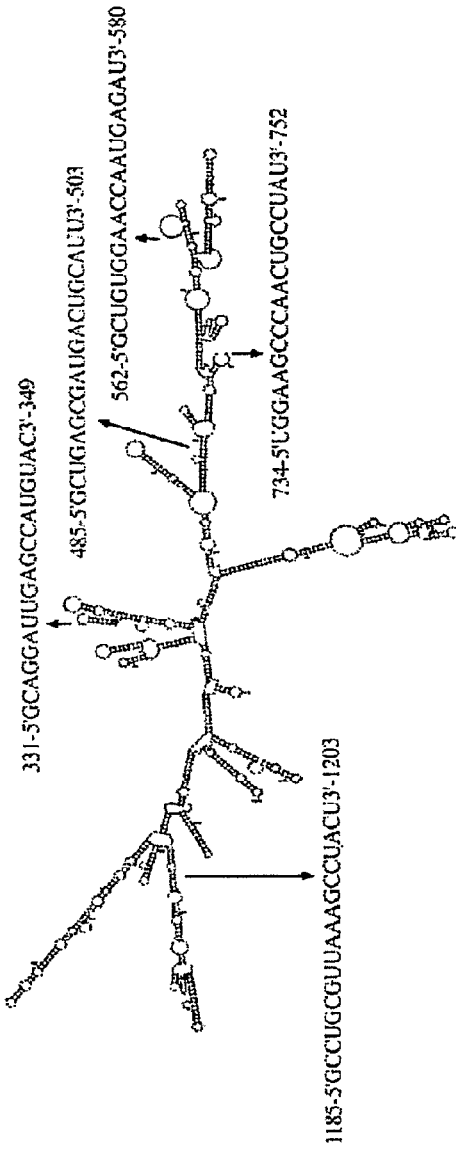
Figure 15B:
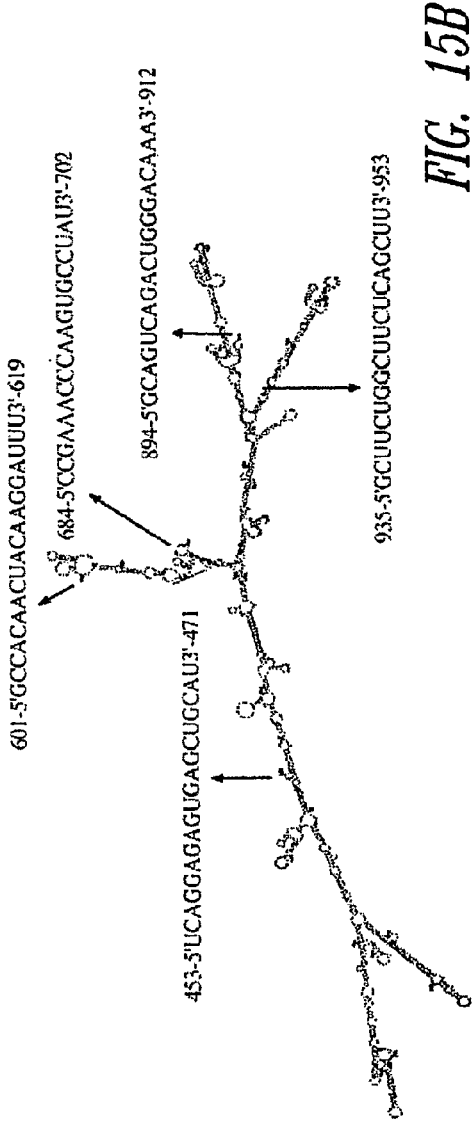

FIGS. 15A and 15B show the deduced stem-loop structures of the human (FIG. 15A) and mouse (FIG. 15B) TCblR mRNA, as well as the sequences of oligonucleotides directed to siRNA target regions identified within these mRNAs (SEQ ID NOs:6-15).

Figure 16:
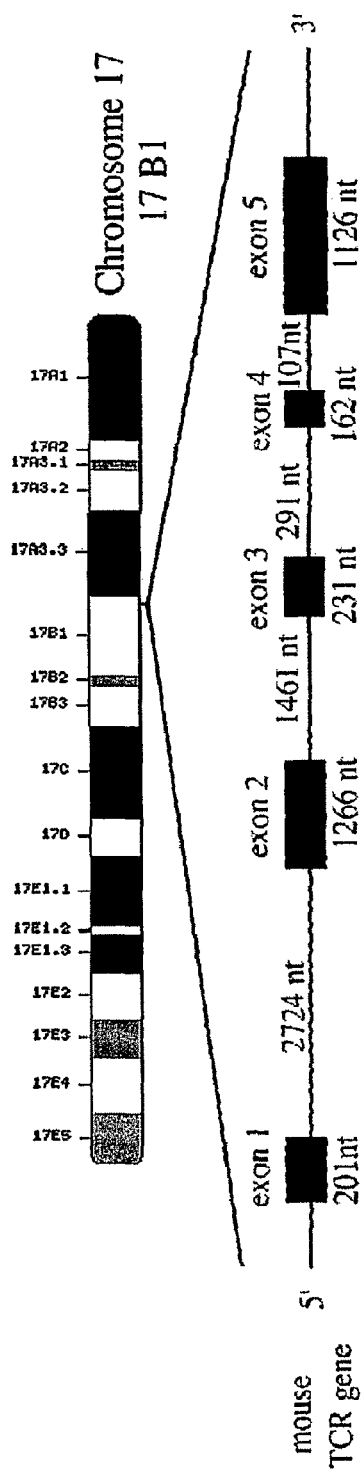

FIG. 16 is a schematic diagram of mouse chromosome 17, which indicates the chromosomal location and gene structure of mouse TCblR.

Figure 17:
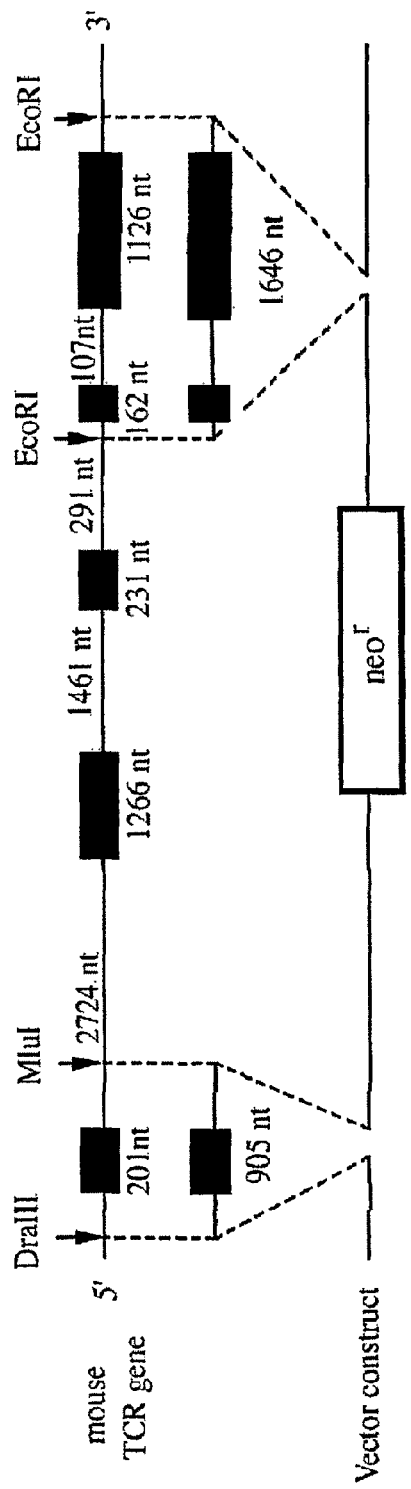

FIG. 17 is a schematic diagram depicting targeted disruption of the mouse TCblR gene. The mouse TCblR gene is indicated on the top, and the targeting vector construct is shown below.

Figure 18:
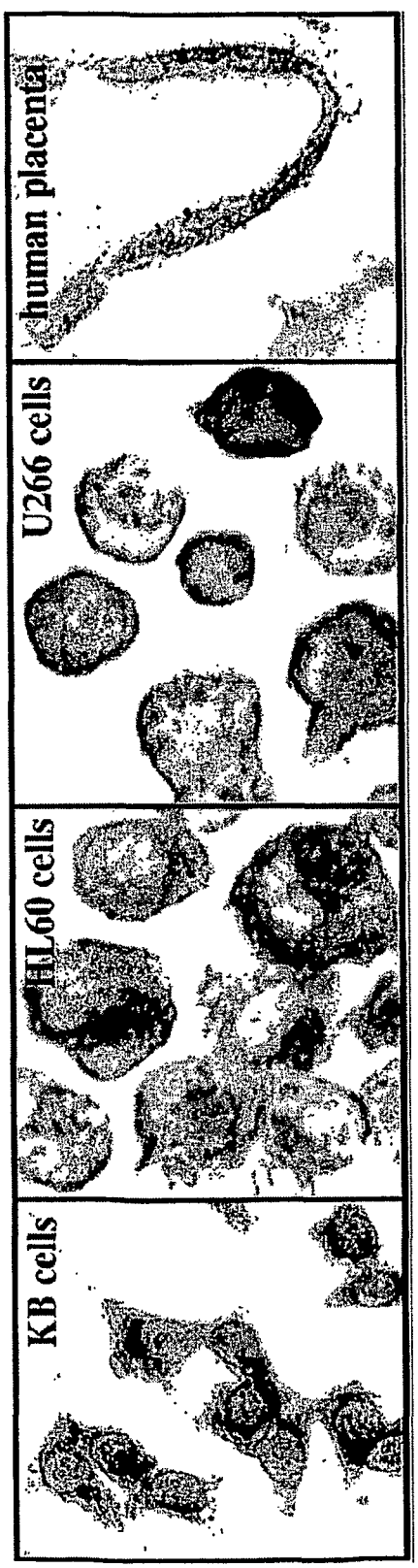

FIG. 18 shows a photomicrograph of immunohistochemical localization of TCblR in various cancer cell lines and human placenta using polyclonal serum directed to the extracellular domain of TCblR.

Figures 19, 20:
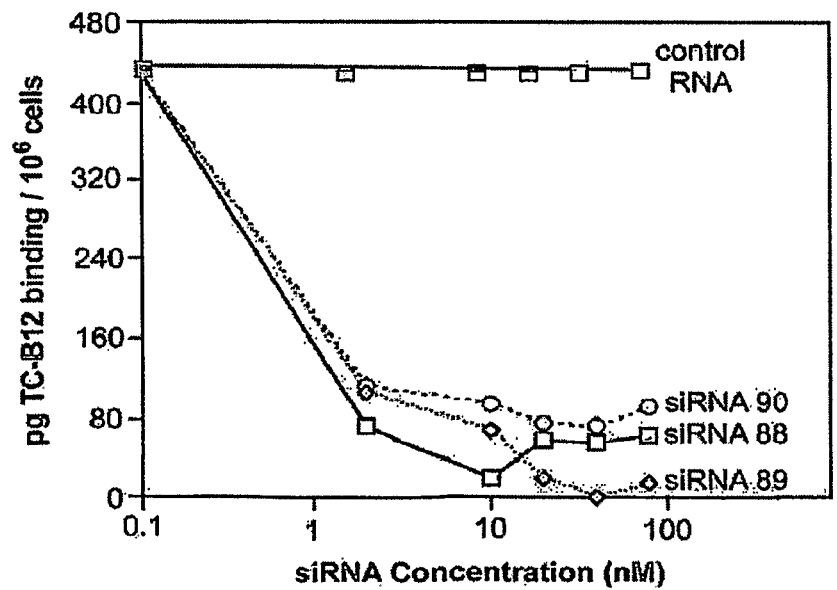

FIG. 19 provides the TCblR polynucleotide sequences present within three different siRNAs (TCblR.88 (SEQ ID NO:16), TCblR.89 (SEQ ID NO:17), and TCblR.90 (SEQ ID NO:18)) targeting TCblR.

FIG. 20 is a graph depicting the reduction in transcobalamin binding to HEK298 cells in the presence of control RNA or the indicated siRNAs targeting the TCblR polynucleotide sequence.

Figure 21:

FIG. 21 shows the expression and purification of recombinant TCblR extracellular domain. The left panel shows a Coomassie stained SDS-PAGE gel of purified recombinant TCblR extracellular domain and molecular) weight markers. The right panel shows western blot staining of purified recombinant TCblR extracellular domain using a polyclonal antiserum directed against the TCblR extracellular domain.

Figure 22:
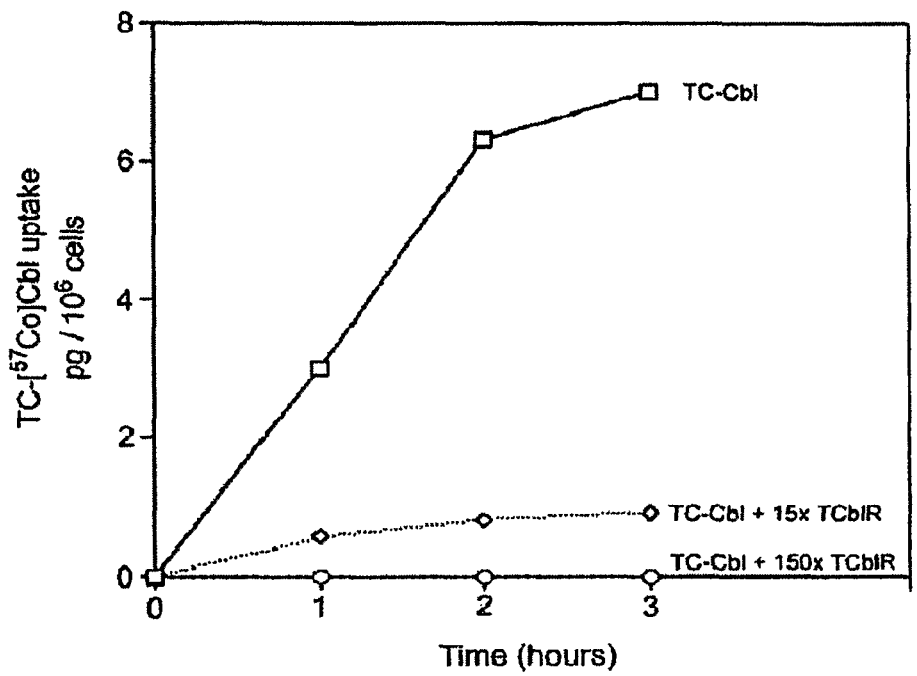

FIG. 22 is a graph demonstrating the reduction in transcobalamin uptake by K562 cells in the presence of a 15-fold or 150-fold excess of recombinant TCblR extracellular domain.

DETAILED DESCRIPTION OF THE INVENTION

The present invention is based upon the cloning and molecular characterization of the transcobalamin receptor (TCblR), including the elucidation of the cDNA and polypeptide sequences of TCblR, as well as the identification of functional domains involved in the biological activity of TCblR and cis sequences within the TCblR gene that regulate the expression of TCblR. The invention is further based upon the identification of TCblR's critical role in cobalamin (Cbl) uptake and the identification of regions of TCblR involved in binding and uptake of transcobalamin (TC) and Cbl. In addition, aspects of the present invention are based upon the characterization of the expression of TCblR, which indicates that TCblR is overexpressed in proliferating and dividing cells, including tumor cells.

Based upon the identification and characterization of the sequences and biological properties of TCblR, the present invention provides novel compositions and methods for regulating Cbl uptake and cell growth, including methods of treating diseases and disorders associated with poor Cbl uptake, as well as diseases and disorders associated with hyperproliferation or deregulated cell growth, such as tumors. In additional aspects, the present invention provides screening methods to identify modulators of TCblR activity and methods of using molecules that bind TCblR to identify and deliver therapeutic agents to tumor cells.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

As used in this specification and the appended claims, the singular forms "a," "an" and "the" include plural references unless the content clearly dictates otherwise.

A. Transcobalamin Receptor Polypeptides and Nucleic Acids

Many embodiments of compositions and methods of the present invention comprise or utilize a TCblR polypeptide or polynucleotide or variant fragment thereof, including recombinantly produced TCblR polypeptide and polynucletoides. The TCblR polypeptide sequence identified according to the present invention was previously identified as the 8D6 antigen, or CD320 antigen, although it was not known before that these antigens corresponded to TCblR. The 8D6 antigen was originally identified as a follicular dendritic cell molecule that stimulates geminal center B cell growth (Li, L. et al., *J. Exp. Med.* 191:1077-1083 (2000) and Zhang, X. et al., *J. Immunol.* 167:49-56 (2001)). The amino acid sequence of human TCblR protein is set forth in SEQ ID NO:1, and the sequence of the human TCblR cDNA corresponding to the mRNA is set forth in SEQ ID NO:2, with the coding region of the cDNA provided in SEQ ID NO:3.

Various transcobalamin receptor polypeptide and polynucleotide sequences are available in NCBI public sequence databases under the following accession numbers: NM_016579, *Homo sapiens* CD320 antigen (CD320), mRNA, gi|51702225|ref|NM_016579.2|[51702225] (SEQ ID NO:2); CR457174, *Homo sapiens* full open reading frame cDNA clone RZPDo834A0912D for gene 8D6A, 8D6 antigen; complete cds, incl. Stopcodon, gi|48146464|emb|CR457174.1|[48146464] (SEQ ID NO:3); BC000668, *Homo sapiens* CD320 antigen, mRNA (cDNA clone MGC:828, IMAGE:3347569), complete cds, gi|34784777|gb|BC000668.2|[34784777] (SEQ ID NO:19); BC007083, *Homo sapiens* CD320 antigen, mRNA (cDNA clone MGC:14623, IMAGE:4076237), complete cds, 3937942|gb|BC007083.1|[13937942] (SEQ ID NO:20); NT_086894, *Homo sapiens* chromosome 19 genomic contig, alternate assembly, gi|51475033|ref|NT086894.1|Hs19_86558[51475033]; NT_077812, *Homo sapiens* chromosome 19 genomic contig, gi|37574721|ref|NT_077812.2|Hs19_77861 [37574721]; NP_057663, 8D6 antigen [*Homo sapiens*], gi|7706111|ref|NP_057663.1|[7706111] (SEQ ID NO:1); CAG33455, 8D6A [*Homo sapiens*], gi|48146465|emb|CAG33455.1|[48146465]; AAH07083, 8D6 antigen [*Homo sapiens*], gi|13937943|gb|AAH07083.1| [13937943]; AAH00668, 8D6 antigen [*Homo sapiens*], gi|12653765|gb|AAH00668.1|[12653765]; Hs.333427, 8D6A: CD320 antigen, *Homo sapiens,* 297 sequence(s); CD320, Official Symbol: CD320 and Name: CD320 antigen

[*Homo sapiens*]Other Aliases: HGNC:16692, 8D6, 8D6A Other Designations: 8D6 antigenChromosome: 19; Location: 19p13.3-p13.2GeneID: 51293.

The present invention contemplates the use of any polynucletoides sequence that encodes a TCblR or fragment thereof, as well as non-coding sequences. Thus, in various embodiments of the present invention, either coding or non-coding sequences are utilized, and either sense or antisense sequences are utilized.

1. Polypeptides

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations, amidations, and the like, as well as other modifications known in the art, both naturally occurring and non-naturally occurring. A polypeptide may be an entire protein, or a portion thereof. Particular polypeptides of interest in the context of this invention are amino acid subsequences comprising functional domains of TCblR, including fragments capable of binding TC and/or Cbl, as well as dominant negative mutants, as described infra. As used herein, TC refers to both holo-TC and apo-TC, unless otherwise indicated. Methods of determining whether a TCblR polypeptide binds to TC are known in the art and described herein.

The present invention also includes the use of polypeptide fragments comprising at least 5, 10, 15, 20, 25, 50, 75 or 100 contiguous amino acids, or more, including all intermediate lengths, of a TCblR polypeptide.

Figure 3:
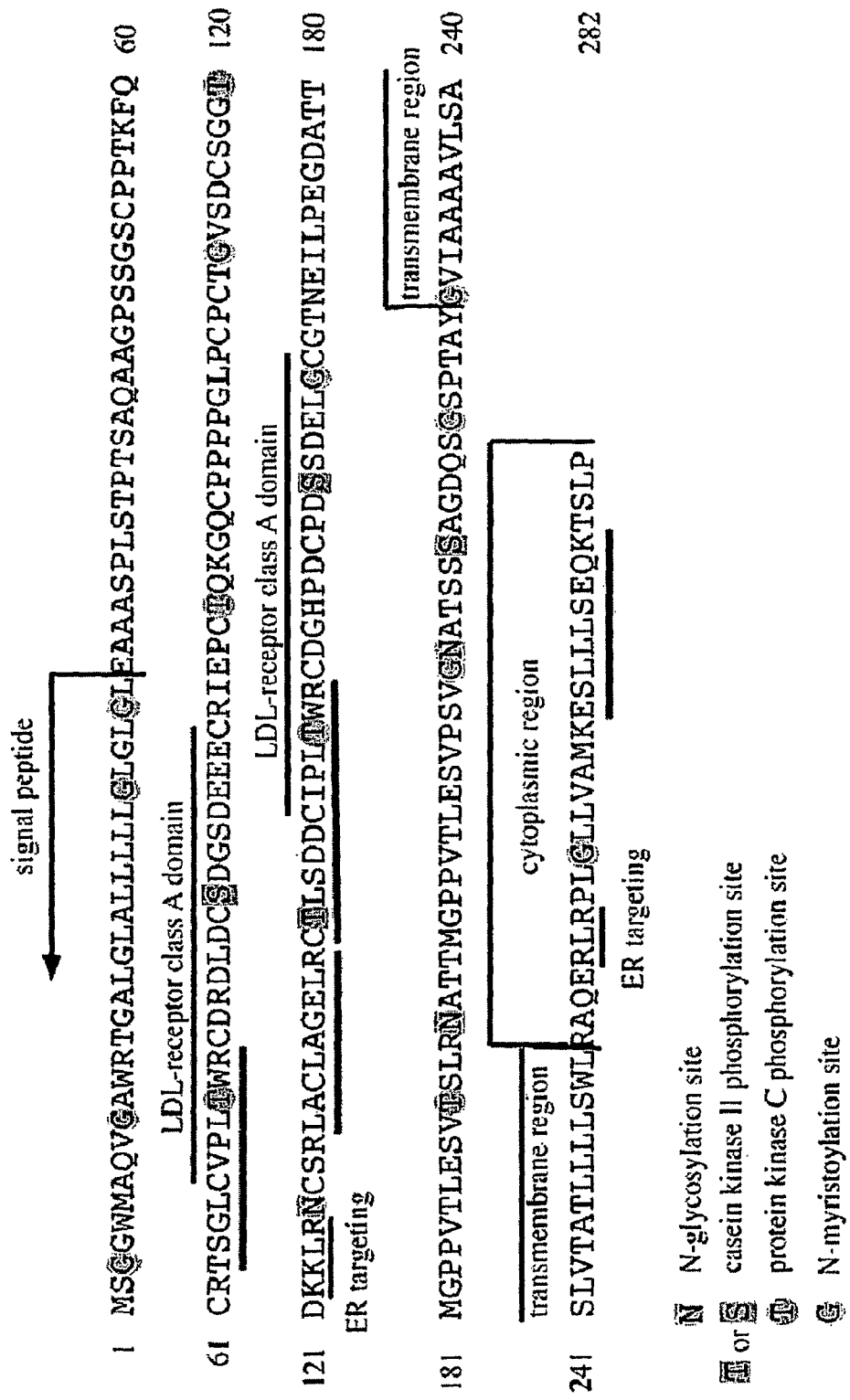

In certain embodiments, the present invention includes polypeptide fragments comprising, consisting essentially of, or consisting of, the extracellular region of a TCblR polypeptide, as shown in FIG. 3. The extracellular domain of TCblR consists of a signal peptide of 31 AA (AA 1-31 of SEQ ID NO:1) and a 198 AA extracellular region (AA 32-229 of SEQ ID NO:1).

This extracellular fragment has been expressed as a recombinant protein in HEK 293 cells. This fragment (AA 1-229 of SEQ ID NO:1) contains the specific high affinity TC-Cbl binding activity and has a 28 fold higher affinity for TC saturated with Cbl (holo-TC) than for the apo protein. This difference is physiologically relevant in that in viva only holo—TC would preferentially bind to the receptor to deliver Cbl into cells. Thus, in particular embodiments, the invention includes a fragment comprising, consisting essentially of, or consisting of AA 1-229 or AA 32-229 of SEQ ID NO:1, and particular embodiments of methods of the present invention use such fragments.

Recombinantly-produced or synthetic extracellular fragments of TCblR, or functional fragments thereof that bind to TC, are, thus useful in blocking binding of holo-TC to cell surface TCblR.

Immunogenic portions of TCblR are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions are identified that have a level of immunogenic activity greater than that of the corresponding full-length polypeptide, e.g., having greater than about 100% or 150% or more immunogenic activity.

In another aspect, the present invention includes the use of variants of TCblR. For example, the invention contemplates the use of TCblR variants, including variants possessing one or more of TCblR's functions, such as being capable of binding TC. A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention. Polypeptide variants will typically exhibit at least about 70%, 75%, 80%, 85%, 90%, 91%, 92%, 93%, 94%, 95%, 96%, 97%, 98%, or 99% or more identity (determined as described below), along its length, to a TCblR polypeptide.

In one preferred embodiment, the TCblR fragments and variants are immunologically reactive with an antibody and/or T-cell that reacts with a full-length TCblR polypeptide. In another preferred embodiment, the TCblR fragments and variants exhibit a level of immunogenic activity of at least about 50%, preferably at least about 70%, and most preferably at least about 90% or more of that exhibited by a full-length TCblR polypeptide.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted by a variety of methods, including, e.g., the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLASTN 2.0.5, FASTA, and TFASTA in the Wisconsin Genetics Software Package, Genetics Computer Group (GCG), 575 Science Dr., Madison, Wis.), or by inspection.

Another example of algorithms that are suitable for determining percent sequence identity and sequence similarity is the BLASTN 2.0.5 algorithm, which are described in Altschul et al. (1977) Nucl. Acids Res. 25:3389-3402 and Altschul et al. (1990) J. Mol. Biol. 215:403-410, respectively. BLASTN 2.0.5 can be used, for example, with the parameters described herein, to determine percent sequence identity for the polynucleotides and polypeptides of the invention. Software for performing BLASTN 2.0.5 analyses is publicly available through the National Center for Biotechnology Information.

As used herein, TCblR includes TCblR polypeptide and polynucleotide sequences from any species, as well as homologs thereof.

Polypeptides of the invention are prepared using any of a variety of well known synthetic and/or recombinant techniques. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

TcblR polypeptides of the present invention may also be recombinantly-produced polypeptides. Methods of recombinantly expressing and isolating or purifying such polypeptides are known in the art. For example, they may be expressed in cells comprising an exogenous TcblR polynucleotide sequence, which may be present in the cell transiently or stably. Such exogenous polynucleotide sequences are typically operatively linked to a promoter, and may be present, e.g., in an expression construct, such as those described infra, or they may be present in the cellular genome. As used herein, "exogenous" polynucleotides and, polypeptide sequences are sequences that have been introduced into a cell, e.g., as a recombinant expression vector comprising the exogenous polynucleotide sequence or an exogenous polypeptide expressed from such an expression vector. The term exogenous does not exclude the possibility that the cell comprising an exogenous sequence also comprises or produces native polynucleotide or polypeptide sequences having the same sequence as the exogenous polynucleotide or polypeptide.

In general, polypeptides of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure, and most preferably at least about 99% pure.

2. Polynucleotides

The present invention also provides TCblR polynucleotide compositions. TCblR polynucletoides include all polynucleotides that encode a TCblR, as well as fragments, variants, and complements thereof. TCblR polynucleotides include genes that encode TCblR, as well as mRNA and cDNA sequences thereof. TCblR polynucleotides further include single- and double-stranded polynucleotides corresponding to a sense or antisense TCblR polynucleotide sequence. Typically, TCblR polynucleotides are isolated. "Isolated," as used herein, means that a polynucleotide is substantially away from other coding sequences, and that the polynucleotide does not contain large portions of unrelated sequence, such as large chromosomal fragments or other functional genes or polypeptide coding regions. Of course, this refers to the polynucleotide as originally isolated, and does not exclude sequences later added to the TCblR polynucleotide by the hand of man.

The polynucleotide compositions of this invention include genomic sequences, extra-genomic and plasmid-encoded sequences, cDNA sequences, RNA sequences, and smaller engineered gene segments. Such segments may be naturally isolated, or modified synthetically by the hand of man. Polynucleotides of the invention may be single-stranded (coding or antisense) or double-stranded, and may be DNA (genomic, cDNA or synthetic) or RNA molecules. In certain embodiments, they are double-stranded RNA or DNA molecules, while in other embodiments, they are single-stranded RNA or antisense molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant, fragment, or derivative, preferably and immunogenic variant, fragment, or derivative, of such a sequence.

cDNA sequences of human TCblR that correspond to a full length TCblR mRNA and the coding region thereof are provided in SEQ ID NOs:2 and 3, respectively. Therefore, according to another aspect of the present invention, polynucleotide compositions are provided that comprise some or all of a polynucleotide sequence set forth in SEQ ID NO:2 or SEQ ID NO:3, complements of a polynucleotide sequence set forth in SEQ ID NO:2 or SEQ ID NO:3, corresponding RNA sequences, and degenerate variants of a polynucleotide sequence set forth in SEQ ID NO:2 or SEQ ID NO:3. The sequences provided in SEQ ID NOs:2 and 3 are DNA sequences. However, it is understood that certain embodiments of the present invention utilize or target the corresponding RNA sequences. Accordingly, methods and compositions of the present invention may comprise an RNA sequence corresponding to any sequence presented here, including the sequences set forth in SEQ ID NOs:2 and 3. In particular embodiments, such RNA sequences are identical to the DNA sequence, except that thymidines are replaced with uridines.

In other related embodiments, the present invention provides polynucleotide variants having substantial identity to a TCblR polynucleotide sequence, e.g., the sequences set forth in SEQ ID NO:2 or SEQ ID NO:3, including sequence having at least 70% sequence identity, preferably at least 75%, 80%, 85%, 90%, 95%, 96%, 97%, 98%, or 99% or higher sequence identity compared to a polynucleotide sequence of this invention using the methods described herein, (e.g., BLAST analysis using standard parameters, as described below).

The promoter sequence of TCblR gene is provided in FIG. 10 and SEQ ID NO:4. In various embodiments, polynucleotides of the present invention comprise at least a fragment of a polynucleotide having the sequence set forth in FIG. 10 or SEQ ID NO:4, or a complement thereof.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. a, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman ((1981) *Add. APL. Math* 2:482), by the identity alignment algorithm of Needleman and Wunsch ((1970) *J. Mol. Biol.* 48:443), by the search for similarity methods of Pearson and Lipman ((1988) *Proc. Natl. Acad. Sci. USA* 85: 2444), by computerized implementations of these algorithms, e.g., GAP, BESTFIT, BLAST, FASTA, and TFASTA in the Wisconsin Genetics Software Package, Genetics Computer Group (GCG); 575 Science Dr., Madison, Wis.), or by inspection.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

3. Expression Constructs

As described infra, in certain embodiments, TCblR activity or expression is altered through the use of recombinantly engineered constructs that express TCblR, functional fragments or variants thereof, or a modulator (e.g., an agonist or inhibitor) of TCblR. In certain embodiments, expression constructs are transiently present in a cell, while in other embodiments, they are stably integrated into a cellular genome. Furthermore, it is understood that due to the inherent degeneracy of the genetic code, other DNA sequences that encode substantially the same or a functionally equivalent amino acid sequence or variant thereof may be produced and these sequences may be used to express a given polypeptide.

Methods well known to those skilled in the art may be used to construct expression vectors containing sequences encoding a polynucleotide or polypeptide of interest, e.g., TCblR or a fragment, mutant or variant thereof, and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y. In one embodiment, expression constructs of the invention comprise polynucleotide sequences encoding all or a region of a TCblR polypeptide, or comprising all or a region of a TCblR cDNA sequence.

Regulatory sequences present in an expression vector include those non-translated regions of the vector, e.g., enhancers, promoters, 5' and 3' untranslated regions, which interact with host cellular proteins to carry out transcription and translation. Such elements may vary in their strength and specificity. Depending on the vector system and cell utilized, any number of suitable transcription and translation elements, including constitutive and inducible promoters, may be used.

In mammalian cells, promoters from mammalian genes or from mammalian viruses are generally preferred, and a number of viral-based expression systems are generally available. In addition, transcription enhancers, such as the Rous sarcoma virus (RSV) enhancer, may be used to increase expression in mammalian host cells. Specific initiation signals may also be used to achieve more efficient translation of sequences encoding a polypeptide of interest. Such signals include the ATG initiation codon and adjacent sequences. Exogenous translational elements and initiation codons may be of various origins, both natural and synthetic. The efficiency of expression may be enhanced by the inclusion of enhancers that are appropriate for the particular cell used, such as those described in the literature (Scharf, D. et al. (1994) Results Probl. Cell Differ. 20:125-162).

In certain embodiments, the invention provides for the conditional expression of TCblR or fragment or variant thereof, or an inhibitor of TCblR activity. A variety of conditional expression systems are known and available in the art for use in both cells and animals, and the invention contemplates the use of any such conditional expression system to regulate the expression or activity of TCblR. In certain embodiments of the invention, the use of prokaryotic repressor or activator proteins is advantageous due to their specificity for a corresponding prokaryotic sequence not normally found in a eukaryotic cell. One example Of this type of inducible system is the tetracycline-regulated inducible promoter system, of which various useful version have been described (See, e.g. Shockett and Schatz, Proc. Natl. Acad. Sci. USA 93:5173-76 (1996) for a review). In one embodiment of the invention, for example, expression of a molecule can be placed under control of the REV-TET system. Components of this system and methods of using the system to control the expression of a gene are well-documented in the literature, and vectors expressing the tetracycline-controlled transactivator (tTA) or the reverse tTA (rtTA) are commercially available (e.g. pTet-Off, pTet-On and ptTA-2/3/4 vectors, Clontech, Palo Alto, Calif.). Such systems are described, for example, in U.S. Pat. Nos. 5,650,298, 6,271,348, 5,922, 927, and related patents, which are incorporated by reference in their entirety.

In particular embodiments, TCblR modulators or TCblR polypeptides, or fragments or variants thereof, are provided to a cell using a viral or bacteriophage vector. A wide variety of viral expression systems are known and available in the art, all of which may be used according to the invention. Therefore, in certain embodiments, polynucleotide inhibitors of TCblR or polynucleotides encoding inhibitors of TCblR or TCblR, or a fragment or variant thereof, are introduced into suitable mammalian host cells or patients using any of a number of known viral-based systems. In one illustrative embodiment, retroviruses provide a convenient and effective platform for gene delivery systems. A selected nucleotide sequence can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Cur. Opin. Genet. Develop.* 3:102-109. In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267-274; Bett at al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich at al. (1993) *Human Gene Therapy* 4:461-476).

Additional viral vectors useful for delivering the polynucleotides encoding polypeptides of the present invention by gene transfer include those derived from the pox family of viruses, such as vaccinia virus and avian poxvirus. In certain embodiments, the methods of the invention utilize lentiviruses. Like other retroviruses, lentiviruses are enveloped viruses that carry a core of RNA encoding their genetic information. Lentiviruses are unique in that lentiviruses are the only retroviruses able to integrate into the chromosome of non-dividing cells. Recombinant self-inactivating lentiviral vectors expressing angiostatin and endostatin have previously been shown to have antiangiogenic activities (Shichinohe T., *Cancer Gene Ther.* 2001 November; 8(11):879-89), and similar methods are used according to the invention to deliver TCblR inhibitors or TCblR polynucleotide, polypeptides, or functional fragments or variants thereof.

Additional illustrative information on these and other known viral-based delivery systems can be found, for example, in Fisher-Hoch at al., *Proc. Natl. Acad. Sci. USA* 86:317-321, 1989; Flexner at al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

B. Transcobalamin Receptor Modulators

In certain embodiments, methods of the invention directed to modulating the activity of TCblR are practiced using a modulator that inhibits or enhances TCblR expression or activity. For example, in certain embodiments, such a modulator specifically increase, reduces, or inhibits TCblR's ability to bind TC or mediate cellular uptake of TC. In other embodiments, a modulator increases or reduces expression of TCblR. In particular embodiments; modulators are polynucleotides, polypeptides, peptides, peptide nucleic acids, antibodies and fragments thereof, viruses, small molecules, inorganic compounds and organic compounds. Modulators include agonists and antagonists of TCblR.

Modulators that increase TCblR activity include TCblR polypeptides and polynucleotides, including those described supra, as well as other molecules that enhance TCblR expression or activity. Modulators that decrease TCblR activity include any molecule that reduces TCblR expression or activity. In certain embodiments, inhibitors interfere with TCblR activity by any of a variety of means including, e.g., inhibiting TCblR binding to TC or inhibiting downstream signaling events leading to Cbl uptake and/or cell growth.

1. Peptides and Polypeptides

In certain embodiments, methods of the invention are practiced using peptide or polypeptide modulators of TCblR.

In one embodiment, TCblR expression is increased using an expression construct that expresses full length TCblR, or a functional variant or fragment thereof.

In another embodiment, the activity of TCblR is altered by over expression of a dominant negative inhibitor of TCblR. Dominant negative inhibitors of TCblR are typically mutant forms of TCblR, which reduce or block the activity of wild type TCblR, e.g., by competing for binding to TC but failing to fully activate the TCblR signaling or uptake pathway. Typically, dominant negative inhibitors of TCblR have a reduced ability to promote cell growth as compared to wild type TCblR. Examples of various TCblR dominant negative inhibitors include a mutant TCblR having reduced ability to bind TC and a mutant TCblR that binds TC but fails to internalize TC and/or Cbl. For example, one dominant negative is a TCblR having one or more amino acid substitutions in the intracellular domain, such that the mutant TCblR binds TC but exhibits reduced uptake of TC and/or Cbl.

Polypeptide inhibitors also include other variants and fragments of TCblR having reduced biological activity as compared to wild type TCblR. One example of a mutant TCblR inhibitor is a TCblR in which the region that binds TC has been mutated so that it has reduced TC binding ability. One example of an inhibitor is a soluble fragment of TCblR that includes the TCblR extracellular domain and is capable of binding to TC but does not promote TC and/or Cbl uptake. Thus, in one embodiment, an inhibitor of TCblR comprises the extracellular fragment of TCblR depicted in FIG. 13 or a functional fragment thereof. In specific embodiments, it comprises, consists of, or consists essentially of AA 1-229 or AA 32-229 of SEQ ID NO:1. In one particular embodiment, a modulator of TCblR comprises or consists of the first 229 or 247 amino acids of the TCblR protein. In related embodiment, it comprises or consists of AA 32-229 or 32-247 of TCblR. While in certain embodiments, polypeptide modulators comprising or consisting of a fragment of the extracellular domain of TCblR do not include the signal peptide (AA 1-31), in certain embodiments, the signal peptide is included, e.g., to direct the protein to the plasma membrane for secretion into the medium.

The extracellular domain of TCblR consists of a signal peptide of 31 AA (AA 1-31) and a 198 AA extracellular region (AA 32-229). This extracellular region contains the specific high affinity TC-Cbl binding activity and has a 28 fold higher affinity for TC saturated with Cbl (holo-TC) than for the apo protein. This difference is physiologically relevant in that in-vivo only holo—TC preferentially binds to the receptor to deliver Cbl into cells. Accordingly, soluble extracellular domain, e.g., with or without the signal peptide may be used to block holo-TC binding to cell surface-bound TCblR and block cellular uptake of Cbl. This property of the receptor provides an additional method to block cellular uptake of Cbl as a strategy in cancer therapy. This could be accomplished by saturating the circulating TC in the patient's blood with the recombinant receptor fragment. This would prevent the holo TC from binding to the receptor on the cell surface and block cellular uptake of Cbl.

In addition, other domains of TCblR described in the Examples provided herein may also be used according to the methods of the invention.

2. Polynucleotides

Various polynucleotides are contemplated for use as modulators of TCblR expression and/or activity. In one embodiment, a polynucleotide encoding TCblR or a functional variant or fragment thereof is used to increase TCblR expression. These polynucleotides include expression vectors and replacement or insertion vectors designed for integration into the genome of a cell, and suitable for gene therapy. In certain embodiments, polynucleotide inhibitors of TCblR are antisense RNA, ribozymes, aptamers, or RNA interference reagents designed to specifically target TCblR, according to methods known and available in the art. Other polynucleotide inhibitors include, e.g., targeting vectors designed for integration into the genome and suitable for deleting all or a portion of a TCblR allele or mutating a TCblR allele, e.g., through insertional mutagenesis.

a. Antisense

In one embodiment, a TCblR inhibitor is an antisense RNA directed to TCblR polynucleotides, or other components of the TCblR signaling cascade. Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739, 119 and 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., *Science,* 1988 Jun. 10; 240(4858):1544-6; Vasanthakumar and Ahmed, Cancer Commun. 1989; 1(4):225-32; Penis et al., *Brain Res Mol Brain Res.,* 1998 Jun. 15; 57(2):310-20; U.S. Pat. Nos. 5,801,154; 5,789,573; 5,718,709 and 5,610, 288). Furthermore, antisense constructs have also been described that inhibit and can be used to treat a variety of abnormal cellular proliferations, e.g. cancer (U.S. Pat. Nos. 5,747,470; 5,591,317 and 5,783,683).

Therefore, in certain embodiments, the present invention relates to methods of providing oligonucleotide sequences that comprise all, or a portion of, any sequence that is capable of specifically binding to a TCblR target polynucleotide sequence, or a complement thereof. In another embodiment, the oligonucleotide sequence comprises all, or a portion of, any sequence that is capable of specifically binding to a TCblR polynucleotide sequence, or a complement thereof. In one embodiment, the antisense oligonucleotides comprise DNA or derivatives thereof. In another embodiment, the oligonucleotides comprise RNA or derivatives thereof. The antisense oligonucleotides may be modified DNAs comprising a phosphorothioated modified backbone. Also, the oligonucleotide sequences may comprise peptide nucleic acids or derivatives thereof. In each case, preferred compositions comprise a sequence region that is complementary, and more preferably, completely complementary to one or more portions of a TCblR target gene or polynucleotide sequence. In particular embodiments, an antisense polynucleotide of the present invention comprises a fragment of a sequence set forth in SEQ ID NOs:2 or 3, or a complement thereof. In another embodiment, an antisense polynucleotide of the present invention comprises a fragment of the sequence set forth in FIG. 10, or a complement thereof.

Methods of producing antisense molecules are known in the art and can be readily adapted to produce an antisense molecule that targets TCblR. Selection of antisense compositions specific for a given sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., *Nucleic Acids Res.* 1997, 25(17):3389-402).

b. Ribozymes

According to another embodiment of methods of the invention, ribozyme molecules are used to inhibit expression of a TCblR target gene or polynucleotide sequence. Ribozymes are RNA-protein complexes having specific catalytic domains that possess endonuclease activity (Kim and Cech, *Proc Natl Acad Sci USA.,* 1987 December; 84(24):8788-92; Forster and Symons, *Cell,* 1987 Apr. 24;49(2):211-20). For example, a large number of ribozymes accelerate phosphoester transfer reactions with a high degree of specificity, often cleaving only one of several phosphoesters in an oligonucleotide substrate (Cech et al., Cell, 1981 December; 27(3 Pt 2):487-96; Michel and Westhof, *J Mol. Biol.* 1990 Dec. 5; 216(3):585-610; Reinhold-Hurek and Shub, *Nature,* 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or *Neurospora* VS RNA motif, for example. Specific examples of hammerhead motifs are described by Rossi et al. *Nucleic Acids Res.,* 1992 Sep. 11; 20(17):4559-65. Examples of hairpin motifs are described by Hampel et al. (Eur. Pat. Appl. Publ. No. EP 0360257), Hampel and Tritz, *Biochemistry,* 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, *Biochemistry,* 1992 Dec. 1; 31(47):11843-52; an example of the RNaseP motif is described by Guerrier-Takada et al., *Cell,* 1983 December; 35(3 Pt 2):849-57; *Neurospora* VS RNA ribozyme motif is described by Collins (Saville and Collins, *Cell,* 1990 May 18; 61(4):685-96; Saville and Collins, *Proc Natl Acad Sci USA,*

1991 Oct. 1; 88(19):8826-30; Collins and Olive, *Biochemistry*, 1993 Mar. 23; 32(11):2795-9); and an example of the Group I intron is described in (U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to TCblR are known in the art. Ribozymes may be designed as described in Int. Pat. Appl. Publ. No. WO 93/23569 and Int. Pat. Appl. Publ. No. WO 94/02595, each specifically incorporated herein by reference and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

c. RNAi Molecules

RNA interference methods using RNAi molecules also may be used to disrupt the expression of a gene or polynucleotide of interest, including a TCblR gene or another gene associated with the TCblR signaling cascade.

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S, and Christian, A. T., (2003) Molecular Biotechnology 24:111-119). Accordingly, the invention includes the use of RNAi reagents comprising any of these different types of double-stranded molecules. In addition, it is understood that RNAi reagents may be used and introduced to cells in a variety of forms. Accordingly, as used herein, RNAi reagents encompasses any and all reagents capable of inducing an RNAi response in cells, including, but not limited to, double-stranded polynucleotides comprising two separate strands, i.e. a sense strand and an antisense strand, polynucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

In one particular embodiment, a dsRNA molecule that targets and induces degradation of a TCblR polynucleotide is introduced to a cell. While the exact mechanism is not essential to the invention, it is believed the association of the dsRNA to the target gene is defined by the homology between the dsRNA and the actual and/or predicted mRNA transcript. It is believed that this association will affect the ability of the dsRNA to disrupt the target gene. DsRNA methods and reagents are described in PCT applications WO 99/32619, WO 01/68836, WO 01/29058, WO 02/44321, WO 01/92513, WO 01/96584, and WO 01/75164, which are hereby incorporated by reference in their entirety.

In one embodiment of the invention, RNA interference (RNAi) may be used to specifically inhibit target expression of TCblR. Double-stranded RNA-mediated suppression of gene and nucleic acid expression may be accomplished according to the invention by introducing dsRNA, siRNA or shRNA into cells or organisms. dsRNAs less than 30 nucleotides in length do not appear to induce nonspecific gene suppression, as described supra for long dsRNA molecules. Indeed, the direct introduction of siRNAs to a cell can trigger RNAi in mammalian cells (Elshabir, S. M., et al., *Nature* 411:494-498 (2001)). Furthermore, suppression in mammalian cells occurred at the RNA level and was specific for the targeted genes, with a strong correlation between RNA and protein suppression (Caplen, N. et al., *Proc. Natl. Acad. Sci. USA* 98:9746-9747 (2001)). In addition, it was shown that a wide variety of cell lines, including HeLa S3, COS7, 293, NIH/3T3, A549, HT-29, CHO-KI and MCF-7 cells, are susceptible to some level of siRNA silencing (Brown, D. et al. *TechNotes* 9(1):1-7, available at http://www.ambion.com/techlib/tn/91/912.html (Sep. 1, 2002)).

RNAi reagents targeting TCblR can be readily prepared according to procedures known in the art. Structural characteristics of effective siRNA molecules have been identified. Elshabir, S. M. et al. (2001) *Nature* 411:494-498 and Elshabir, S. M. et al. (2001), *EMBO* 20:6877-6888. Accordingly, one of skill in the art would understand that a wide variety of different siRNA molecules may be used to target a specific gene or transcript. In various embodiments, RNAi sequences are less than or equal to 50 nucleotoides in length, less than or equal to 40 nucleotides in length, less than or equal to 30 nucleotides in length, or less than or equal to 20 nucleotides in length. In certain embodiments, siRNA molecules according to the invention are 16-30 or 18-25 nucleotides in length, including each integer in between. In one embodiment, an siRNA is 21 nucleotides in length. In certain embodiments, siRNAs have 0-7 nucleotide 3' overhangs or 0-4 nucleotide 5' overhangs. In one embodiment, an siRNA molecule has a two nucleotide 3' overhang. In one embodiment, an siRNA is 21 nucleotides in length with two nucleotide 3' overhangs (i.e. they contain a 19 nucleotide complementary region between the sense and antisense strands). In certain embodiments, the overhangs are UU or dTdT 3' overhangs. Generally, siRNA molecules are completely complementary to one strand of a target DNA molecule, since even single base pair mismatches have been shown to reduce silencing. Accordingly, in particular embodiments, an siRNA molecule is complementary to a region of a sequence set forth in SEQ ID NOs:2 or 3, or the sequence shown in FIG. 10.

In certain embodiments, siRNAs may have a modified backbone composition, such as, for example, 2'-deoxy- or 2'-O-methyl modifications. However, in certain embodiments, the entire strand of the siRNA is not made with either 2' deoxy or 2'-O-modified bases.

In particular embodiments, siRNA molecules are single- or double-stranded oligonucleotides. As used herein, the term "oligonucleotide" refers to a polynucleotide formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)- or (Sp)-phosphorothioate, alkylphosphonate, or phosphotriester linkages).

The oligonucleotides of the invention can include naturally occurring nucleosides, modified nucleosides, or mixtures thereof, so long as they consist of, consist essentially of or comprise a portion of a TCblR polynucleotide sequence or complement thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

As used herein, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides. The term "oligonucleotide" includes hybrid and chimeric oligonucleotides.

A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

siRNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because these are typically the result of a post-transcriptional modification) are within the term unmodified RNA, as used herein.

Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules that are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

For increased nuclease resistance and/or binding affinity to a target mRNA, an oligonucleotide agent can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e., deoxyribose sugars, which are of particular relevance to the overhang portions of partially ds RNA); halo (e.g., fluoro); amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diary) amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH.sub.3, 2'-O-allyl, 2'-C-allyl, and 2'-fluoro. To maximize nuclease resistance, the 2' modifications can be used in combination with one or more phosphate linker modifications (e.g., phosphorothioate).

The inclusion of furanose sugars in the oligonucleotide backbone can also decrease endonucleolytic cleavage. An oligonucleotide agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

In other embodiments, oligonucleotide agents are 5' phosphorylated or include a phosphoryl analog at the 5' prime terminus. 5'-phosphate modifications of the antisense strand include those that are compatible with RISC mediated gene silencing. Suitable modifications include: 5'-monophosphate ((HO)$_2$(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

In one embodiment, siRNA target sites are selected by scanning the target mRNA transcript sequence for the occurrence of AA dinucleotide sequences. Each AA dinucleotide sequence in combination with the 3' adjacent approximately 19 nucleotides are potential siRNA target sites. In one embodiment, siRNA target sites are preferentially not located within the 5' and 3' untranslated regions (UTRs) or regions near the start codon (within approximately 75 bases), since proteins that bind regulatory regions may interfere with the binding of the siRNP endonuclease complex (Elshabir, S. et al. *Nature* 411:494-498 (2001); Elshabir, S. et al. *EMBO J.* 20:6877-6888 (2001)). In addition, potential target sites may be compared to an appropriate genome database, such as BLASTN 2:0.5, available on the NCBI server at www.ncbi.nlm, and potential target sequences with significant homology to other coding sequences eliminated.

Short hairpin RNAs may also be used to inhibit or knockdown gene or nucleic acid expression according to the invention. Short Hairpin RNA (shRNA) is a form of hairpin RNA capable of sequence-specifically reducing expression of a target gene. Short hairpin RNAs may offer an advantage over siRNAs in suppressing gene expression, as they are generally more stable and less susceptible to degradation in the cellular environment. It has been established that such short hairpin RNA-mediated gene silencing (also termed SHAGging) works in a variety of normal and cancer cell lines, and in mammalian cells, including mouse and human cells. Paddison, P. et al., *Genes Dev.* 16(8):948-58 (2002). Furthermore, transgenic cell lines bearing chromosomal genes that code for engineered shRNAs have been generated. These cells are able to constitutively synthesize shRNAs, thereby facilitating long-lasting or constitutive gene silencing that may be passed on to progeny cells. Paddison, P. et al., *Proc. Natl. Acad. Sci. USA* 99(3):1443-1448 (2002).

ShRNAs contain a stem loop structure. In certain embodiments, they may contain variable stem lengths, typically from 19 to 29 nucleotides in length, or any number in between. In certain embodiments, hairpins contain 19 to 21 nucleotide stems, while in other embodiments, hairpins contain 27 to 29 nucleotide stems. In certain embodiments, loop size is between 4 to 23 nucleotides in length, although the loop size may be larger than 23 nucleotides without significantly affecting silencing activity. ShRNA molecules may contain mismatches, for example G-U mismatches between the two strands of the shRNA stem without decreasing potency. In fact, in certain embodiments, shRNAs are designed to include one or several G-U pairings in the hairpin stem to stabilize hairpins during propagation in bacteria, for example. However, complementarity between the portion of the stem that binds to the target mRNA (antisense strand) and the mRNA is typically required, and even a single base pair mismatch is this region may abolish silencing. 5' and 3' overhangs are not required, since they do not appear to be critical for shRNA function, although they may be present (Paddison et al. (2002) *Genes & Dev.* 16(8):948-58).

Examples of specific siRNA target sequences in the human and mouse TCblR mRNA are shown in FIGS. 15 and 19. Accordingly, in certain embodiments, siRNAs comprising all or a region of these target sequences or complements or homologs or orthologs thereof are contemplated according to the present invention.

d. Knockout Constructs

In certain embodiments, the activity of TCblR is altered by mutating a gene encoding the TCblR molecule or a gene encoding another component of the TCblR biological pathway. A variety of methods of mutating an endogenous gene are known and available in the art, including, e.g., insertional mutagenesis and knockout methods. Accordingly, the invention includes methods of knocking out one or more alleles of a TCblR gene. It is understood that knockout vectors according to the invention include any vector capable of disrupting expression or activity of a TCblR gene, including, in certain embodiments, both gene trap and targeting vectors.

In preferred methods, targeting vectors are used to selectively disrupt a TCblR gene. Knockout vectors of the invention include those that alter gene expression, for example, by disrupting a regulatory element of a TCblR gene, including, e.g., inserting a regulatory element that reduces gene expression or deleting or otherwise reducing the activity of an endogenous element that positively affects transcription of the target gene. In other embodiments, knockout vectors of the invention disrupt, e.g., delete or mutate, the 5' region, 3' region or coding region of a TCblR gene. In some embodiments, knockout vectors delete a region or the entirety of the coding region of a TCblR gene. In certain embodiments, knockout vectors delete a region of a TCblR gene, while in other embodiments, they insert exogenous sequences into a TCblR gene. In addition, in certain embodiments, including those using replacement vectors, knockout vectors both remove a region of a gene and introduce an exogenous sequence.

Targeting vectors of the invention include all vectors capable of undergoing homologous recombination with an endogenous TCblR gene, including replacement vectors. Targeting vectors include all those used in methods of positive selection, negative selection, positive-negative selection, and positive switch selection. Targeting vectors employing positive, negative, and positive-negative selection are well known in the art and representative examples are described in Joyner, A. L., *Gene Targeting: A Practical Approach,* 2nd Ed. (2000) and references cited therein.

e. Aptamers and Avimers™

In particular embodiments, the present invention contemplates the use of aptamers as modulators of TCblR. Aptamers are polynucleotide or peptide molecules that bind a specific target molecule, e.g., TCblR. Aptamers commonly bind to targets with similar affinity as antibodies. However, aptamers offer advantages over antibodies, since they can be engineered completely in a test tube, are readily produced by chemical synthesis, possess desirable storage properties, and elicit little or no immunogenicity in therapeutic applications. Aptamers may be combined with ribozymes to self-cleave in the presence of their target molecule.

A therapeutic aptamer termed AS1411 is currently undergoing Icinical trials for the treatment of renal and non-small cell lung cancers. This aptamer is a G-rich polynucletoide comprising a single-stranded DNA chain of 26 bases with unmodified phosphodiester linkages. AS1411 self anneals to form a quadruplex structure that is resistant to degradation by serum enzymes. AS1411 binds to nucleolin, which is expressed on tumor cell surfaces, leading to its internalization and a strong anti-proliferative cellular response. Dosage studies found that doses up to 40 mg/kg/day for up to 7 days were well tolerated, and a response rate of 17% and clinical benefit of 75% in patients with advanced metastatic renal cell carcinoma was observed in early testing.

DNA or RNA aptamers typically consist of short strands of oligonucleotides. In certain embodiments, polynucleotide aptamers of the present invention are nucleic acid species that have been evolutionary engineered through in vitro selection or equivalently, systematic evolution of ligands by exponential enrichment (SELEX) to bind to TCblR.

Peptide aptamers typically consist of a short variable peptide domain. Peptide aptamers of the present invention typically bind to TCblR or interfere with the binding of TC or Cbl to TCblR. In particular embodiments, they comprise or consist of a variable peptide loop attached at both ends to a protein scaffold. This double structural constraint greatly increases the binding affinity of the peptide aptamer to levels comparable to an antibody's (nanomolar range). The variable loop length is typically 10 to 20 amino acids, and the scaffold may be any protein which have good solubility and compacity properties, such as the bacterial protein Thioredoxin-A is the most used scaffold protein, the variable loop being inserted within the reducing active site, which is a -Cys-Gly-Pro-Cys- (SEQ ID NO:21) loop in the wild protein, the two Cysteine lateral chains being able to form a disulfide bridge. Peptide aptamer selection can be made using different systems, but the most used is currently the yeast two-hybrid system.

In certain embodiments, the activity of aptamers of the present invention is regulated by ligand binding to the aptamer, i.e., Ligand Regulated Peptide Aptamers (LiRPAs). For example, by displaying 7 amino acid peptides from a novel scaffold protein based on the trimeric FKBP-rapamycin-FRB structure, interaction between the randomized peptide and target molecule can be controlled by the small molecule Rapamycin or non-immunosuppressive analogs.

Aptamers are usually created by selecting them from a large random sequence pool, e.g., using SELEX, in vitro selection, or yeast two-hybrid screening, as described above. Various method of identifying and producing aptamers specific for a target of interest, such as TCblR, are described in the following references: Ellington A D, Szostak J W, *Nature*, 1990 Aug. 30; 346(6287):818-22; Bock L C, Griffin L C, Latham J A, Vermaas E H, Toole J J, *Nature*, 1992 Feb. 6, 355(6360):564-6; Hoppe-Seyler F, Butz K, *J Mol Med.* 2000; 78(8):426-30; Carothers J M, Oestreich S C, Davis J H, Szostak J W, *J Am Chem. Soc.* 2004 Apr. 28; 126(16):5130-7; Cohen B A, Colas P, Brent R, *PNAS* 1998 Nov. 24; 95(24): 14272-7; Binkowski B F, Miller R A, Belshaw P J, *Chem & Biol.* 2005 Jul., 12 (7):847-55; Sullenger B A, Gilboa E, *Nature* 2002, 418:252-258; and Ng E W, Shima D T, Callas P, Cunningham E T, Jr., Guyer D R, Adamis A P, *Nat Rev Drug Discov* 2006, 5:123-132. Aptamers may also be identified using phage display techniques, including those described infra for the identification of antibodies and fragments thereof.

In other embodiments, the present invention contemplates the use of Avimers™ as modulators of TCblR or cobalamin uptake. Avimers™ are single-protein chains, typically smaller than 25 kD in size, which are composed of multiple binding domains. Each binding domain is designed to bind to a particular target site. In certain embodiments, these binding domains bind to the same protein target, or they can bind to multiple or different protein targets. The modular binding domains may be generated from the exon shuffling of extracellular receptor domains. Thus in particular embodiments, an Avimer™ of the present invention comprises one or more binding domains that binds to transcobalamin or TCblR.

In particular embodiments, an Avimer™ of the present invention comprises an immunoglobulin binding domain, e.g., IgG, in addition to the binding domain that bind transcobalamin or TCblR. Attachment of the immunoglobulin binding domain is understood to result in enhanced serum stability of the Avimer™.

In other embodiments, the present invention contemplates the use of receptorbodies as modulators of TCblR or transcobalamin uptake. In particular embodiments, the present invention is directed to a receptorbody comprising the extracellular domain of TCblR fused to an immunoglobulin constant region. In particular embodiments, the extracellular domain is a fragment of TCblR capable of binding transcobalamin. Thus, in particular embodiments, receptorbodies, aptamers, and Avimers™ may be administered to a patient, wherein they bind and sequester transcobalamin, preventing its binding to cell surface TCblR and uptake by cells.

3. Antibodies

Antibodies, or antigen-binding fragments thereof, that specifically bind TCblR are also activators or inhibitors of TCblR according to the methods described herein. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions. Antibodies are considered to specifically bind to a target polypeptide when the binding affinity is at least $1 \times 10^{-7}$ M or, preferably, at least $1 \times 10^{-8}$ M. In one embodiment, a modulator is an antibody that specifically binds the extracellular domain of TCblR.

Antibodies used in the methods of the invention include, but are not limited to, monoclonal antibodies, chimeric antibodies, humanized antibodies, fully human antibodies, Primatized® antibodies, single chain antibodies, Fab fragments, and scFv fragments.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies via conventional techniques known in the art, or via transfection of antibody genes into suitable bacterial or mammalian cell hosts, in order to allow for the production of recombinant antibodies. Monoclonal antibodies specific for an antigenic polypeptide of interest may be prepared, for example, using the technique of Kohler and Milstein, Eur. J. Immunol. 6:511-519, 1976, and improvements thereto. Methods of making chimeric and humanized antibodies are well known in the art, (See, e.g., U.S. Pat. No. 4,816,567, International Application No. WO84/03712, respectively).

In certain embodiment, methods of preparing monoclonal antibodies involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab)$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1,'CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The invention further includes veneered framework (FR) antibodies. As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

Fab or F(ab')$_2$ fragments may be wholly animal or human derived, or they may be in chimeric form, such that the constant domains are derived from the constant regions of human immunoglobulins and the variable regions are derived from the parent murine MAb. Alternatively, the Fv, Fab, or F(ab')$_2$ may be humanized, so that only the complementarity determining regions (CDR) are derived from an animal MAb, and the constant domains and the framework regions of the variable regions are of human origin. These chimeric and humanized fragments are less immunogenic than their wholly animal counterparts, and thus more suitable for in vivo use, especially over prolonged periods.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349: 293-299; Lobuglio et al. (1989) *Proc. Nat. Acad. Sci. USA* 86:4220-4224; Shaw et al. (1987) *J Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589, 369 and 5,545,807.

In one embodiment, humanized or fully human antibodies of the present invention are prepared according to the methods described in U.S. Pat. Nos. 5,770,429, 5,833,985, 5,837,243, 5,922,845, 6,071,517, 6,096,311, 6,111,166, 6,270,765, 6,303,755, 6,365,116, 6,410,690, 6,682,928, and 6,984,720, all assigned to Medarex, Inc.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties.

Thus, the phage mimics some of the properties of the B cell.

Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.*

222:581-597 (1991), or Griffith et al., *EMBO J.* 12:725-734 (1993). See, also, U.S. Pat. Nos. 5,565,332 and 5,573,905.

Phage display may be used to generate synthetic antibodies or human antibodies (and aptamers) according to various methods. For example, in certain embodiments, phage display is utilized to produce a library of fully human antibodies or fragments thereof, which may be screened for their ability to bind a target polypeptide, such as TCblR. The screening of such libraries is commercially available, e.g., by Morphosys (Munich, Germany). Libraries of human antibodies and methods of use thereof are described, e.g., in U.S. Pat. Nos. 7,049,135, 6,828,422, 6,753,138, 6,706, and 484, 6,696,248, and U.S. Patent Application Publication Nos. 2006/0121563, 2006/0003334, and 2004/0157291, all assigned to Morphosys.

Additional methods of generating and screening human antibody and aptamer libraries using phage display are described, e.g., in Steukers, M. et al., *J Immunol Methods.* 2006 Mar. 20; 310(1-2):126-35; Huang L. et al., *J. Leukoc. Biol. Vol* 80. 2006 Oct.; Wassaf, D. et al., *Anal Biochem.* 2006 Apr. 15; 351(2):241-53; Shrivastava A, et al., *Protein Eng Des Sel.* 2005 September; 18(9):417-24; Schoonbroodt S. et al., *Nucleic Acids Res.* 2005 May 19; 33(9); Hogan S, et al., *Biotechniques.* 2005 April; 38(4):536, 538; Hoet R M, et al., *Nat. Biotechnol.* 2005 March; 23(3):344-8; Huang L, et al., *J Mol. Recognit.* 2005 Feb. 10; Blaise L, et al., *Gene.* 2004 Nov. 24; 342(2):211-8; Fleming T, et al., *J. Mol. Recognit.* 2004 17:1-9; Jostock, et al., *J Immunol Methods.* 2004 June; 289 (1-2):65-80; Kelley B, et al., *J Chip.* 4 Jun. 2004 2004; 1038 (1-2):121-130; Ladner R C, et al., *Drug Discovery Today*. June 2004; 9(12):525-529; Williams A, Baird L G, *Transfus Apheresis Sci.* December 2003; 29(3):255-258; van den Beucken T, et al., *FEBS Lett*. Jul. 10 2003; 546(2-3):288-294. Jul. 10 2003; 546(2-3):288-294; Sato A., *Biopolymers*. July 2003; 71(3):316; and Nixon A E., *Biopolymers*. July 2003; 71(3):302, 398.

Human antibodies may also be generated by in vitro activated B cells (see U.S. Pat. Nos. 5,567,610 and 5,229,275).

In one embodiment, an antibody serves as an inhibitor of TCblR signaling by binding to TCblR, e.g., the extracellular domain, and thereby inhibiting binding of TC to TCblR.

4. Small Molecules

Modulators (inhibitors or activators) of the present invention further include large or small inorganic or organic molecules. In certain embodiments, modulators are small organic molecules, or derivatives or analogs thereof.

In certain embodiments, a modulator includes a protecting group. The term "protecting group" refers to chemical moieties that block at least some reactive moieties and prevent such groups from participating in chemical reactions until the protective group is removed (or "cleaved"). Examples of blocking/protecting groups are described, e.g., in Greene and Wuts, Protective Groups in Organic Synthesis, 3rd Ed., John Wiley & Sons, New York, N.Y., 1999.

Any of the modulators may possess one or more chiral centers and each center may exist in the R or S configuration. Modulators of the present invention include all diastereomeric, enantiomeric, and epimeric forms as well as mixtures thereof. Stereoisomers may be obtained, if desired, by methods known in the art as, for example, the separation of stereoisomers by chiral chromatographic columns. Modulators further include of N-oxides, crystalline forms (also known as polymorphs), and pharmaceutically acceptable salts, as well as active metabolites of any inhibitor. All tautomers are included within the scope of the modulators presented herein. In addition, the modulators described herein can exist in unsolvated as well as solvated forms with pharmaceutically acceptable solvents such as water, ethanol, and the like. The solvated forms of the modulators presented herein are also included within the present invention.

In a particular embodiment, a small molecule inhibitor binds to TCblR. In one embodiment, a small molecule binds to the extracellular region of TCblR and interferes or reduces TC binding to TCblR.

Modulators of TCblR, including small organic compounds, may be identified according to routine screening procedures available in the art, e.g., using commercially available libraries of such compounds.

5. Methods of Identifying Transcobalamin Receptor Modulators

The invention further provides methods of identifying and producing modulators (inhibitors and inducers, including antagonists and agonists) of TCblR expression and/or activity, including inhibitors and inducers having therapeutic properties. In certain embodiments, inhibitors and inducers modulate one or more of TCblR's functional properties, such as, e.g., TCblR's ability to bind TC, promote uptake of Cbl or enhance cell replication or growth.

In general, modulators of TCblR are identified by screening candidate molecules, including, e.g., all of the different types of molecules described above. Any assay suitable for determining TCblR function or activity may be utilized, including, but not limited to, binding assays and biological functional assays described herein.

Candidate modulators may be screened individually, e.g., when a specific molecule is predicted to function as an inhibitor or inducer/activator. Alternatively, a library of compounds or molecules may be screened. Examples of such libraries, which are readily available commercially, include recombinant expression libraries, libraries of small inorganic compounds, phage display libraries expressing antibodies or fragments thereof (including aptamers), and libraries of small organic compounds.

The invention contemplates at least two different types of inhibitors of TCblR, including (1) molecules that decrease a functional activity of TCblR; and (2) molecules that decrease expression levels of TCblR. An inhibitor of TCblR is identified as a molecule or compound that reduces one or more of TCblR's activities or expression by at least 10%, at least 25%, at least 50%, at least 75% or 100%.

In general, the invention contemplates two different types of inducers, including (1) molecules that increase the functional activity of TCblR; and (2) molecules that increase expression levels of TCblR, including, e.g., a TCblR expression construct. An inducer of TCblR is identified as a molecule or compound that increases one or more of TCblR's activities by at least two-fold, at least five-fold, at least ten-fold or more. In the context of overexpression of TCblR, an inducer is a molecule or compound that increases expression of TCblR at least two-fold, at least five-fold, at least ten-fold or more.

In one embodiment, the TCblR functional activity is binding to TC. In another embodiment, inducers or inhibitors are identified by their ability to bind to TCblR or a functional fragment thereof. Routine binding assays suitable for screening candidate molecules and compounds are well known in the art and include, e.g., GST pulldown assays using recombinantly-produced GST-TCblR fusion polypeptides, affinity chromatography, phage display, immunoprecipitation assays under low stringency conditions suitable for precipitating TCblR complexes using antibodies to TCblR, ELISA assays, and radioimmunoassays.

Modulators of TCblR may also be identified based upon their ability to alter, e.g., increase or decrease, one or more biological activities of TCblR or cobalamin. For example, a modulator may be identified by performing a cell-based assay to compare the amount of cobalamin taken up by a cell that expresses TcblR in the presence or absence of a candidate modulator. In particular embodiments, the presence of an inhibitor of TcblR results in decreased cobalamin uptake, and the presence of an inducer of TcblR results in increased cobalaim uptake. Since cobalamin is associated with cell proliferation, modulators of TCblR may also be identified based upon their ability to modulate cell growth or proliferation. For example, cells expressing TcblR are contacted with cobalamin in the presence or absence of a candidate modulator. The cells are then cultured for a suitable time and cell proliferation is determined, e.g., by counting the number of viable cells before and after culturing them. The presence of an inhibitor of TcblR in the culture media results in decreased proliferation as compared to proliferation in the absence of such an inhibitor. Similarly, the presence of an inducer of TcblR in the culture media results in increased proliferation as compared to proliferation in the absence of such an inducer. In particular embodiments, the cells used comprise an exogenous or recombinantly-expressed TcblR polypeptide.

In particular embodiments of the present invention, screening or modulation of TCblR is performed using recombinantly expressed TCblR or a fragment thereof, or using cells comprising exogenous TCblR or a fragment thereof, which is typically expressed in the cell from a recombinant expression construct. Methods utilizing recombinant TCblR are advantageous in that recombinant protein is typically easier to obtain and purify.

In one embodiment, modulators of TCblR are aptamers, e.g., polynucleotide or polypeptide aptamers. Thus, the present invention contemplates the screening of aptamers to identify an aptamer that modulates cobalamin uptake into a cell, e.g., using any of the techniques described herein. Such aptamers may be used for a variety of diagnostic, prognostic, and therapeutic uses, including those described infra.

In one embodiment, modulators of TcblR are antibodies, e.g., human antibodies. Thus, the present invention contemplates the screening of antibodies, including human antibodies, to identify an antibody that modulates cobalamin uptake into a cell. Such antibodies may be used for a variety of diagnostic, prognostic, and therapeutic uses, including those described infra.

In one embodiment, the present invention includes a method of identifying an antibody that modulates cobalamin uptake into a cell, comprising: producing a human monoclonal antibody specific for TcblR; and testing the antibody for its ability to bind to interfere or promote Tc binding to TcblR, its ability to modulate cobalamin uptake by a cell expressing TcblR, or its ability to alter one or more biological activities of cobalamin or TcblR.

In particular embodiments, the antibody is generated by immunizing a transgenic mouse that expresses human antibody chains with purified or isolated TcblR protein. In particular embodiments, the purified or isolated TcblR protein is recombinantly-produced TcblR protein. Examples of such mice include the HuMAb-Mouse, the Kirin T C Mouse, and the KM-Mouse, produced by Medarex. In HuMAB-Mouse transgenic mice, the mouse genes for creating antibodies have been inactivated and replaced by human antibody genes. Our HuMAb-Mouse transgenic strains contain key gene sequences from unrearranged human antibody genes that code for both the heavy and light chains of human antibodies. Because these genes determine what antibody proteins are made, these transgenic mice make human antibody proteins. The Kirin TC Mouse mice contain complete sets of the variable and constant genes found in the corresponding natural human immunoglobulin loci. These mice are "transchromosomic," meaning that the mouse genes for creating antibodies have been inactivated and have been replaced by the human chromosomes containing all of the human antibody genes, including all heavy chain classes that encode all isotypes (IgG1-4, IgA1-2, IgD, IgM and IgE). The TC Mouse also has the ability to make fully human monoclonal antibodies. The KM-Mouse is a crossbred mouse that combines the characteristics of our HuMAb-Mouse with the Kirin TC Mouse that retains the capability to produce all human antibody isotypes with a strong immune response. Hybridomas are then produced from cells, e.g., spleen cells, obtained from the immunized mice using conventional techniques, and the hybridoma supernatants are screened for antibodies specific for TcblR. The supernatants may, alternatively, or in addition, be tested for their ability to modulate one or more TcblR activities, e.g., the ability to bind Tc or the ability to mediate cobalamin uptake by a cell. Hybridomas that produce antibodies specific for TcblR or modulate TcblR activity are cloned and propogated.

In particular embodiments, screening assays are performed using high throughput techniques. For example, binding assays may be performed using microtitre dishes with multiple wells, such as a 96-well dish. In one embodiment, inhibitors or inducers are identified by placing cells expressing TCblR into the wells of a microtitre dish, adding a different molecule or compound to be tested into individual wells, adding radiolabelled TC to the wells, and determining the amount of bound radiolabelled TC in each well after washing away excess unbound radiolabelled TC.

In certain embodiments, modulators of TCblR are identified using a recombinantly expressed TCblR polypeptide, such as a full length TCblR polypeptide or a fragment thereof, e.g., the extracellular domain. In particular embodiments, the methods of screening for modulators of TCblR are performed in vitro, using purified recombinant TCblR protein. In other embodiments, methods of screening for modulators of TCblR are performed using cells that express TCblR on their surface. The TCblR may be endogenous TCblR, but in certain embodiments, the TCblR is exogenous, and is expressed in the cell via an expression construct introduced to the cell. In particular embodiments, the cell expresses exogenous TCblR having the sequence set forth in SEQ ID NO:1 or a fragment thereof.

In other embodiments, modulators are identified by other means of identifying a TCblR binding partner, such as phage display techniques and yeast two-hybrid screening. Again, these may be performed using cells that express exogenously introduced TCblR or a fragment thereof, e.g., an extracellular domain thereof.

In one embodiment, the present invention includes a method of producing a human antibody that inhibits cobalamin uptake into a cell, comprising producing a human antibody specific for a transcobalamin receptor by immunizing a transgenic non-human animal that expresses human antibody polypeptides with a purified recombinantly-produced transcobalamin receptor polypeptide or an immunogenic portion thereof, wherein said recombinantly-produced transcobalamin polypeptide is purified from a cell comprising an exogenous polynucleotide encoding TCblR or a fragment thereof, operatively linked to a promoter sequence, such that the cell expresses the recombinantly-produced TCblR polypeptide or fragment thereof.

In another embodiment, the present invention includes a method of identifying a TCblR modulator (e.g., an aptamer, a human antibody, or a polypeptide fragment of TCblR) that inhibits cobalamin uptake into a cell, comprising: contacting a purified recombinantly-produced transcobalamin receptor polypeptide, or an immunogenic portion thereof, with transcobalamin, or a fragment thereof, in the presence of a candidate TCblR modulator (e.g., a human antibody specific for a transcobalamin receptor); determining an amount of the transcobalamin bound to the transcobalamin receptor; and comparing the amount of bound transcobalamin to an amount bound in the absence of the candidate TCblR modulator, wherein a decreased amount of bound transcobalamin indicates that the candidate TCblR modulator inhibits cobalamin uptake into a cell.

In another embodiment, the present invention includes a method of identifying a TCblR modulator (e.g., a human antibody) that inhibits cobalamin uptake into a cell, comprising: contacting a cell expressing an exogenous transcobalamin receptor with transcobalamin in a candidate TCblR modulator; determining an amount of the transcobalamin taken up by the cell; and comparing the amount transcobalamin taken up by the cell to an amount taken up in the absence of the candidate TCblR modulator, wherein a decreased amount of transcobalamin taken up by the cell indicates that the candidate TCblR modulator is an inhibitor of cobalamin uptake into a cell.

In a further embodiment, the present invention includes a method of producing a monoclonal antibody that inhibits cobalamin uptake into a cell, comprising: isolating a recombinantly-produced TCblR polypeptide, or an immunogenic portion thereof, from a transgenic cell comprising an exogenous polynucleotide that encodes a TCblR polypeptide, or a fragment thereof, operatively linked to a promoter sequence; immunizing an animal with said recombinantly-produced transcobalamin receptor polypeptide; and purifying antibodies specific for said transcobalamin receptor polypeptide from cells obtained from said animal.

Method of the invention may further comprise demonstrating that the antibody or other TCblR modulator inhibits cobalamin uptake into a cell by contacting a transcobalamin receptor, or a fragment thereof, with transcobalamin, or a fragment thereof, in the presence of the antibody or TCblR modulator; determining an amount of the transcobalamin bound to the transcobalamin receptor; and comparing the amount of bound transcobalamin to an amount bound in the absence of the antibody or TCblR modulator, wherein a decreased amount of bound transcobalamin indicates that the antibody or TCblR modulator inhibits cobalamin uptake into a cell.

Methods of the invention may further comprise demonstrating that the antibody or other TCblR modulator inhibits cobalamin uptake into a cell by contacting a cell expressing a transcobalamin receptor with transcobalamin in the presence of the antibody or TCblR modulator; determining an amount of the transcobalamin taken up by the cell; and comparing the amount transcobalamin taken up by the cell to an amount taken up in the absence of the antibody or TCblR modulator, wherein a decreased amount of transcobalamin taken up by the cell indicates that the antibody or TCblR modulator is an inhibitor of cobalamin uptake into a cell.

Inhibitors and inducers of TCblR may be manufactured, e.g., by identifying such a molecule as described above and producing said identified molecule. In addition, identified molecules may be derivatized using standard procedures available in the art and further screened or tested to identify a molecule having improved function as an inhibitor or inducer of TCblR expression or activity, e.g., binding to TC. In particular embodiments, human antibodies that modulate TcblR are manufactured by immunizing a transgenic animal that expresses one or more human antibody chains with a TcblR polypeptide or fragment thereof, using cells from the immunized animal to produce hybridomas, screening hybridoma supernatant to identify a hybridima that specifically binds TcblR, and cloning said hybridoma. In particular embodiments, hybridoma supernatant is also screening to identify a hybridoma that modulates TcblR.

6. Modified Transcobalamin Modulators

In another embodiment of the invention, modulators of TCblR, e.g., monoclonal antibodies or small organic compounds that specifically bind TCblR, may be coupled to one or more detectable labels or therapeutic agents. Suitable labels and therapeutic agents include radionuclides, differentiation inducers, drugs, toxins, and derivatives thereof. In particular embodiments, radionuclides include $^{90}$Y, $^{123}$I, $^{125}$I, $^{131}$I, $^{186}$Re, $^{188}$Re, $^{211}$At, and $^{212}$Bi. In certain embodiments, the modulator is coupled to a non-metallic radionuclide, which may be, e.g., Carbon-11, Iodine-124, Fluorine-18, Bromine-76, or Iodine-123. Preferred drugs include chemotherapeutic agents.

A therapeutic agent may be coupled (e.g., covalently bonded) to a suitable modulator or monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Examples of linkers and methods of coupling therapeutic agents such as radionuclides to a modulator of the present invention are described, e.g., in U.S. Pat. Nos. 7,179,445, 7,141,233, 6,838,073, 6,806,363, 6,613,305, 6,211,355, 6,096,290, 6,004,533, and 5,739,313, all assigned to the Mayo Clinic. These patents also describe methods of utilizing cobalamin conjugates for a variety of therapeutic, antitumor, and imaging purposes, which may be readily adapted to utilize a modulator (or conjugate thereof) of the present invention instead of cobalamin.

In certain embodiments, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group that is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

C. Methods of Use and Pharmaceutical Compositions of TCblR Modulators

The present invention identifies the polypeptide and polynucleotide sequences of TCblR, thereby permitting the use of these polypeptides and polynucleotides, as well as those identified modulators thereof, to regulate cellular processes associated with TCblR activity. As will be readily understood by one of skill in the art, TCblR is associated with a variety of cellular processes, including those regulated by Cbl. Accordingly, modulators of TCblR may be used to alter these cellular processes, and treat and prevent associated diseases and disorders in patients. In particular embodiments, a patient is a human or another animal. In one embodiment, a patient is a mammal.

TCblR has been shown to be overexpressed in a variety of diseases, including tumors and other proliferative disorders. Specifically, up-regulation in the number of transcobalamin II receptors has been demonstrated in several malignant cell lines during their accelerated thymidine incorporation and DNA synthesis (see, U.S. Pat. No. 6,806,363, J. Lindemans et al., *Exp. Cell. Res.*, 184, 449 (1989); T. Amagasaki et al., *Blood*, 26, 138 (1990) and J. A. Begly et al., *J. Cell Physiol.*, 156, 43 (1993). Thus, modulators of TCblR and other compositions described herein may be used to treat or prevent diseases characterized by increased expression levels of TCblR polynucleotides or polypepetides.

Cbl depletion as a strategy to block cellular proliferation has been shown to be effective in vitro, using anti TC mAbs and hence, anti TCblR mAb should also be effective. Ultimately a combination of mAbs to both proteins may prove most effective, and falls within the scope of the present invention. In addition, this essential gateway may be used to deliver Cbl-drug conjugates to neoplastic cells because of the over expression of TCblR in these cells. The hypothesis that the arrest of neoplastic proliferation can be realized by selective nutrient depletion is supported by serendipitous findings in patients with undiagnosed leukemia presenting with Cbl or folate deficiency who upon treatment for their deficiency develop full blown leukemia. This approach differs from conventional chemotherapy and therefore, may reduce many of the side effects and toxicities associated with chemotherapy. Among the potential concerns of the deleterious effects of TCblR-based therapeutic strategies are the concerns of toxicity, especially to the hematopoeitic system and the nervous system. The neuropathological complications of Cbl deficiency usually take several years to develop and therefore may not be a major concern in short-term therapy. However, the bone marrow and other normal replicating tissues such as the mucosal surfaces are likely to be affected. The effect of Cbl deficiency or Cbl antimetabolites could be readily reversed by administering a large bolus of Cbl which can bypass the physiologic pathway, an approach similar to the folinic acid rescue after methotrexate therapy. The uptake and turnover of Cbl in proliferating cells is a dynamic process, limited only by the available TC-Cbl and the TCblR expressed. This property of the cells allows for the rapid exchange or replacement of intracellular Cbl.

The TCblR polypeptide sequence was previously identified as the 8D6 antigen, or CD320 antigen, although it was not known that these antigens corresponded to the TCblR. The 8D6 antigen was originally identified as a follicular dendritic cell molecule that stimulates geminal center B cell growth (Li, L. et al., *J. Exp. Med.* 191:1077-1083 (2000) and Zhang, X. et al., *J. Immunol.* 167:49-56 (2001)). 8D6 has since been shown to collaborate with CD44 in supporting lymphomagenesis by a Burkitt lymphoma cell line (Li, L. et al., Blood 104:815-821. Accordingly, the TCblR modulators described herein may also be used to diagnose, treat, or prevent a variety of immunological and inflammatory diseases, in addition to tumors, both solid and liquid, e.g., leukemias and lymphomas. For example, in one particular embodiment, an siRNA molecule of the present invention may be used to treat lymphoma, e.g., a B cell lymphoma, multiple myeloma, follicular lymphomas.

In certain embodiments, methods of the present invention directed to treating or preventing a disease or disorder associated with Cbl deficiency (including intracellular Cbl deficiency) involve providing a functional TCblR polypeptide or polynucleotide, or other enhancer of TCblR activity or expression, to a cell or patient. In contrast, methods of the present invention directed to treating or preventing a disease or disorder associated with hyperproliferation, inflammation, or deregulated cell growth typically involve providing an inhibitor of TCblR to a cell or patient.

1. Methods of Inhibiting Cobalamin Uptake

As demonstrated herein, TCblR is the primary receptor governing cellular uptake of TC or Cbl. Accordingly, Cbl uptake may be inhibited by blocking the binding of TC to TCblR using a modulator of the present invention. The present invention, therefore, provides methods of inhibiting TC binding to a cell and methods of inhibiting Cbl uptake by a cell, which include contacting a cell with a modulator of TCblR activity, wherein said modulator inhibits the binding of holo-TC to TCblR and the uptake of Cbl by the cell.

In particular embodiments, the modulator is an antibody, e.g., a monoclonal antibody that specifically binds to the extracellular domain of TCblR. In another embodiment, the modulator is a small organic compound that binds to the extracellular domain of TCblR. In another embodiment, the modulator is an siRNA directed to TCblR polynucleotide sequences. In particular embodiments, the modulator binds at or near the TC binding site on TCblR and either competitively or sterically inhibits or reduces binding of TC to TCblR.

In other embodiments, the modulator is a fragment of TCblR that includes at least a portion of the extracellular domain (AA 1-229 of SEQ ID NO:1). In specific embodiments, this fragment comprises, consists essentially of, or consists of AA 1-229 or 32-229 of SEQ ID NO:1.

Cells include both cultured cells, as well as cells present in a patient's body. In addition, cells include both normal and diseased cells. In one particular embodiment, the cell is a tumor cell or another cell exhibiting deregulated cell growth or hyperproliferation.

According to one embodiment, a modulator is provided to the media of a cultured cell, such that it can readily bind to the extracellular domain of TCblR. In another embodiment, the modulator is provided to the blood or serum of a patient, such that it can compete with serum TC for binding to TCblR.

2. Methods of Inhibiting Cell Growth or Replication, Inducing Apoptosis, and Treating Cancer, Inflammation, Myeloproliferative and Autoimmune Diseases As described herein, TCblR expression is elevated in tumor cells and cells exhibiting enhanced or deregulated growth or proliferation. Similarly, TCblR is overexpressed in certain myeloproliferative and autoimmune disorders. In addition, the TCblR has been identified as playing a role in B cell and dendritic cell growth and differentiation, as well as supporting lymphomagenesis. It is further understood in the art that tumor cells and other cells exhibiting deregulated proliferation undergo apoptosis when deprived of growth factors.

Accordingly, the present invention provides methods of inhibiting cell growth or replication and inducing apoptosis by contacting a cell or patient with an inhibitor of TCblR activity or expression. Such methods may also be applied to cells in culture or to cells in a patient. Accordingly, in the context of a patient, these methods are useful in treating or preventing diseases and disorders associated with hyperproliferation of deregulated cell growth, such as cancer, autoimmune and myeloproliferative disorders, and inhibiting angiogenesis. Without being bound to any particular theory, it is believed that such inhibitors reduce intracellular Cbl levels, leading to reduced cell growth and proliferation, and result in apoptosis under certain situations.

In one embodiment, the inhibitors and methods described herein can be used to treat any type of cancer or tumor. In particular, these methods can be applied to solid tumors or cancers of the blood and lymphatic systems, including lymphomas, leukemia, and myelomas. Examples of specific cancers that may be treated according to the invention include, but are not limited to, Hodgkin's and non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, multiple myeloma, transformed and other types of lymphomas. Examples of specific myeloproliferative disorders that may be treated according to methods of the present invention include, e.g., polycythemia vera, essential thrombocythemia, agnogenic myeloid metaplasia, myelofibrosis, myelodysplastic syndrome, and chronic myelocytic leukemia. The methods of the present invention can be used for adult or childhood forms of lymphoma, as well as lymphomas at any stage, e.g., stage I, II, III, or IV. The various types of lymphomas are well known to those of skill, and are described, e.g., by the American Cancer Society (see, e.g., www3.cancer.org).

As indicated above, the modulators and methods described herein may be applied to any form of leukemia, including adult and childhood forms of the disease. For example, any acute, chronic, myelogenous, and lymphocytic form of the disease can be treated using the methods of the present invention. Additional types of tumors can also be treated using the methods described herein, such as neuroblastomas, myelomas, prostate cancers, small cell lung cancer, colon cancer, ovarian cancer, non-small cell lung cancer, brain tumors, breast cancer, and others.

The modulators described herein may be used to treat neurological, immune related, and inflammatory diseases and disorders, including, but not limited to, multiple sclerosis and arthritis. In addition, the modulators described herein may be used to modulate an immune response.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

The modulators and methods of the present invention may also be used to treat or prevent autoimmune diseases such as rheumatoid arthritis, systemic lupus erythematous and multiple sclerosis.

In particular embodiments, the present methods are employed to treat patients suffering lymphoma, including both Hodgkin's and non-Hodgkin's lymphoma that are follicular lymphoma or diffuse large B cell lymphoma. These lymphomas are most common type of lymphomas in adults in the West.

The modulators of the invention may be administered as first line treatments or as secondary treatments. In addition, they may be administered as a primary chemotherapeutic treatment or as adjuvant or neoadjuvant chemotherapy.

In particular embodiments, the modulator is an antibody, e.g., a monoclonal antibody that specifically binds to the extracellular domain of TCblR. In another embodiment, the modulator is a small organic compound that binds to the extracellular domain of TCblR. In particular embodiments, the modulator binds at or near the TC binding site on TCblR and either competitively or sterically inhibits or reduces binding of TC to TCblR. In other embodiments, the modulator is an siRNA molecule, i.e., a single- or double-stranded oligonucletoide that binds to a TCblR polynucleotide, thereby reducing expression of TCblR.

In other embodiments, the modulator is a fragment of TCblR that includes at least a portion of the extracellular domain (e.g., AA 1-229 of SEQ ID NO:1). In specific embodiments, this fragment comprises, consists essentially of, or consists of AA 1-229 or 32-229 of SEQ ID NO:1. In particular embodiments, such fragments are administered to a patient, where they compete with endogenous cell surface TCblR for binding to holo-TC, thereby preventing uptake of Cbl by a cell, e.g., a tumor cell.

In specific embodiments, a modulator of TCblR activity is provided locally, while in other embodiments, it is provided systemically, e.g., intravenously or intra-arterially. Thus, in particular embodiments of the methods of the present invention, a modulator of TCblR expression or activity (e.g., an antibody or extracellular fragment of TCblR) is provided to a patient's bloodstream, where it inhibits binding of holo-TC to cell surface TCblR and corresponding uptake of cobalamin. Thus, such modulator may be used, e.g., to treat cancer by saturating circulating TC in a patient's blood with a polypeptide comprising, consisting essentially of, or consisting of, the extracellular domain of a TCblR (e.g., SEQ ID NO:1), thereby preventing holo-TC from binding to the receptor on the cell surface and thereby blocking cellular uptake of Cbl.

3. Methods of Detecting, Imaging, and Targeting Tumors

As noted above, TCblR is overexpressed in proliferating cells as compared resting or non-dividing cells. Given that tumor cells demonstrate increased proliferation as compared to normal cells, there is a correspondingly higher expression of TCblR in tumor cells as compared to normal cells. Indeed, it has been demonstrated that labeled coabalamin derivatives can be used for imaging and detection of a wide variety of tumors, including, e.g., primary and metastatic breast, lung, colon, thyroid, sarcomatous, prostate, and central nervous system malignancies (Collins, D. A. at al., *Mayo Clin. Proc.* 75:568-580 (2000)). Accordingly, in certain embodiments, the present invention includes methods of detecting and imaging tumor cells, as well as methods of preferentially delivering a therapeutic agent to a tumor cell, by contacting tumors with an agent that specifically binds to TCblR, e.g., an agent that binds to TCblR coupled to a detectable label and/or a therapeutic agent. These methods may generally be applied to a variety of tumors, including those specifically described herein.

In the context of tumor detection, an agent that specifically binds to TCblR is typically coupled to a detectable label and delivered to a patient. The patient is then examined and the presence and/or location of detectable label determined and correlated with the presence of a tumor. Typically, the presence of a tumor is associated with the detection of at least two-fold, at least three-fold, or at least five-fold as much label as detected in a normal control patient.

In a related embodiment, the presence of tumor cells in a tissue sample obtained from a patient is determined by comparing the amount of binding of an agent that specifically binds TCblR to the tissue sample to the amount of binding to a control normal tissue sample or a predetermined cut-off value. Typically, the presence of tumor cells is associated with at least two-fold, at least three-fold, or at least five-fold as much bound TCblR binding agent as detected in a normal control tissue sample.

These methods may be readily adapted for prognostic purposes. For example, the amount of TCblR detected using an agent that binds to TCblR may be determined before and after treatment. If the amount is reduced following treatment, it suggests that the treatment is efficacious. However, if the amount is increased following treatment, it suggests that the treatment is not efficacious.

In particular embodiments, the TCblR binding reagent is an antibody, e.g., a monoclonal antibody that specifically binds to the extracellular domain of TCblR. In another embodiment, the TCblR binding reagent is a small organic compound that binds to the extracellular domain of TCblR.

The invention contemplates the use of any type of detectable label, including, e.g., visually detectable labels, such as, e.g., dyes, fluorophores, and radioactive labels. In addition, the invention contemplates the use of magnetic beads and electron dense substances, such as metals, e.g., gold, as labels. A wide variety of radioactive isotopes may be used, including, e.g., $^{14}C$, $^{3}H$, $^{99m}Tc$, $^{123}I$, $^{131}I$, $^{32}P$, $^{192}Ir$ $^{103}Pd$, $^{198}Au$, $^{111}In$, $^{67}Ga$, $^{201}Tl$, $^{153}Sm$, $^{18}F$ and $^{90}Sr$. Other radioisotopes that may be used include, e.g., thallium-201 or technetium 99m.

In certain embodiments, the detectable label is a CT contrast agent, also referred to as "dyes." Examples of commonly used contrast agents include iodine, barium, barium sulfate, and gastrografin.

In other embodiments, the detectable agent is a fluorophore, such as, e.g., fluorescein or rhodamine. A variety of biologically compatible fluorophores are commercially available.

Suitable therapeutic agents include radionuclides, differentiation inducers, drugs, toxins, and derivatives thereof. Preferred radionuclides include, e.g., $^{90}Y$, $^{123}I$, $^{125}I$, $^{131}I$, $^{186}Re$, $^{188}Re$, $^{211}At$, and $^{212}Bi$. Preferred drugs include chemotherapeutic agents.

4. Methods of Treating Cobalamin Deficiency

Cbl deficiency is associated with a range of diseases and disorders, including, e.g., megaloblastic anemia and neurological complications affecting both the central and peripheral nervous system, such as degeneration of the spinal cord, peripheral neuropathym and CNS abnormalities. While certain types of Cbl deficiency are the result of insufficient plasma levels of Cbl, other Cbl deficiencies occur in the presence of adequate amounts of plasma levels of Cbl and are due to poor cellular uptake of Cbl. Accordingly, the present invention, in one embodiment, provides a method of treating diseases and disorders associated with Cbl deficiency by increasing the level or activity of TCblR, thereby increasing cellular uptake of Cbl.

The present invention includes various methods of increasing the amount of TCblR in a cell which involve introducing a TCblR polypeptide or polynucleotide, or functional variant or fragment thereof, into a cell. In one embodiment, a polynucleotide comprising a sequence encoding TCblR is introduced into a cell. In various embodiments, the polynucleotide is an expression vector and includes a promoter and/or other regulatory sequences that drive expression of the encoded TCblR in the cell, as described supra. In another embodiment, the polynucleotide is an insertion vector or targeting vector capable of introducing the sequence encoding TCblR into the genome of the cell. Accordingly, the polynucleotide may be either transiently present in the cell or stably integrated into the cellular genome. In particular embodiments, a polynucleotide introduced into a cell using a viral-based vector, according to methods described herein and known in the art.

The methods of the invention directed to increasing the amount of TCblR or the expression of TCblR in a cell may be used to treat or prevent various diseases or disorders associated with Cbl deficiency, including, but not limited to, megaloblastic anemia, pernicious anaemia, neurological dysfunction (including, e.g., ataxia (shaky movements and unsteady gait), muscle weakness, spasticity, incontinence, hypotension, vision problems, dementia, psychoses, dementia, memory loss, and mood disturbances), asthma, depression, AIDS, multiple sclerosis, tinnitus, diabetic neuropathy, gastritis, celiac disease, and low sperm counts.

While methods of the invention directed to increasing cellular levels of TCblR are particularly well-suited to the treatment of Cbl deficiency associated with reduced expression or activity of endogenous TCblR, these methods are also useful in treating Cbl deficiency associated with reduced levels of plasma Cbl, since they enhance TCblR binding and cellular uptake of what little holo-TC is present in the plasma.

5. Therapeutic Compositions

In additional embodiments, the present invention includes pharmaceutical compositions comprising one or more of the modulators disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the modulators described herein in combination with a physiologically acceptable carrier. It will be apparent that any of the compositions described herein can contain pharmaceutically acceptable salts of the modulators of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820, 883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts, and illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

D. Transcobalamin Receptor Knockout Mice

The invention also provides methods of disrupting expression of the TCblR gene in an animal and the resulting knock-out animals and cells. Methods for obtaining knockout animals are well known in the art. Methods of generating a mouse containing an introduced gene disruption are described, for example, in Hogan, B. et al., (1994), Manipulating the Mouse Embryo: A Laboratory Manual, 2nd ed., Cold Spring Harbor Laboratory Press, Cold Spring Harbor, N.Y. and Joyner. In one embodiment, gene targeting, which is a method of using homologous recombination to modify a cell's or animal's genome, can be used to introduce changes into cultured embryonic stem cells. By targeting a TCblR gene of interest in ES cells, these changes can be introduced into the germlines of animals to generate chimeras and TCblR knock-out animals.

Generally, the ES cells used to produce the knockout animals will be of the same species as the knockout animal to be generated. Thus, for example, mouse embryonic stem cells are used for generation of knockout mice. Embryonic stem cells are generated and maintained using methods well known in the art such as those described, for example, in Doetschman, T., et at., J. Embryol. Exp. Morphol. 87:27-45 (1985), and improvements thereof. Any line of ES cells may be used according to the invention. However, the line chosen is typically selected for the ability of the cells to integrate into and become part of the germ line of a developing mouse embryo so as to create germ line transmission of the knockout construct. One example of a mouse strain commonly used for production of ES cells is the 129J strain. Other examples include the murine cell line D3 (American Type Culture Collection, catalog no. CKL 1934) and the WW6 cell line (Ioffe, et al, *PNAS* 92:7357-7361). The cells are cultured and prepared for knockout construct insertion using methods well known to one of ordinary skill in the art, such as those set forth by Robertson in: Teratocarcinomas and Embryonic Stem Cells: A Practical Approach, E. J. Robertson, ed. IRL Press, Washington, D.C. (1987); by Bradley et al., Current Topics in Devel. Biol. 20:357-371 (1986); and by Hogan et al., Manipulating the Mouse Embryo: A Laboratory Manual, Cold Spring Harbor Laboratory Press, Cold Spring Harbor, N.Y. (1986).

Briefly, in certain embodiments, a TCblR gene is disrupted in an embryonic stem cell, and a cell containing the knockout construct in the proper location is identified using routineselection techniques. After suitable ES cells have been identified, the cells may be inserted into an embryo. Insertion may be accomplished in a variety of ways known to the skilled artisan, however, a preferred method is microinjection. The cell may be injected into preimplantation embryos (typically blastocysts). The suitable stage of development for the embryo used for insertion of ES cells is very species dependent, however, for mice, one appropriate age is 3.5 days:

Following introduction of the cells into an embryo, the embryo may be implanted into the uterus of a pseudopregnant foster mother for gestation. Alternatively, the ES cells may be aggregated with morula stage embryos to produce mice. Germline chimeras are selected according to methods well known in the art, and animals homozygous for the disruption are generated by mating. According to preferred methods of the invention, an ES cell is treated with a recombinase prior to injection into a preimplantation embryo, so as to allow normal expression of the disrupted gene and prevent embryonic lethality that might result from a lack of expression of the disrupted gene. Animals of the invention include all species. Preferred animals of the invention include mice, humans, primates, rats, chickens, pigs, sheep, and cows. Other preferred methods of the invention include those methods described in PCT application WO/0042174 and PCT application WO/0051424, including double nuclear transfer.

The present invention further contemplates the generation of conditional TCblR knockout cells and animals using vectors comprising recombinase sites. In certain methods of generating a conditional knockout animal, an embryonic stem cell containing a disrupted gene is treated with a recombinase prior to the production of chimeras or implantation into an animal.

This procedure is particularly advantageous when a disrupted gene is required for embryonic development, as it allows approximately normal gene expression following treatment with the appropriate recombinase. In another embodiment, the recombinase is delivered after the generation of an animal containing at least one disrupted gene allele, by mating the animal containing a disrupted gene with an animal expressing the recombinase. The animal expressing the recombinase may express it ubiquitously, or its expression may be tissue-restricted or temporal-restricted, for example. A recombinase may be introduced to an animal of the invention by mating, for example, by mating an animal containing a marker cassette of the invention with an animal expression a recombinase capable of binding the recombinase sites within the marker cassette. A description of such methods is provided, for example, in WO 9953017 A3, which is hereby incorporated by reference in its entirety.

In certain embodiments, conditional knockout vectors of the invention comprise two recombinase recognition sites. Preferably, these recombinase recognition sites flank a region of the TCblR sequence present in the vector and, in certain embodiments, a marker sequence also present in the vector. In preferred embodiments, the recombinase recognition sites are positioned to direct recombinase-mediated deletion of the marker sequence following identification or selection of desired integration events.

Examples of suitable recombinase sites include FRT sites and loxP sites, which are recognized by the flp and cre recombinases, respectively (See U.S. Pat. Nos. 6,080,576, 5,434,066, and 4,959,317). The Cre-loxP and Flp-FRT recombinase systems are comprised of two basic elements: the recombinase enzyme and a small sequence of DNA that is specifically recognized by the particular recombinase. Both systems are capable of mediating the deletion, insertion, inversion, or translocation of associated DNA, depending on the orientation and location of the target sites. Recombinase systems are disclosed in U.S. Pat. Nos. 6,080,576, 5,434,066, and 4,959,317, and methods of using recombinase systems for gene disruption or replacement are provided in Joyner, A. L., Stricklett, P. K. and Torres, R. M. and Kuhn, R. In Laboratory Protocols for Conditional Gene Targeting (1997), Oxford University Press, New York.

Representative minimal target sites for Cre and Flp are each 34 base pairs in length and are known in the art. The orientation of two target sites relative to each other on a segment of DNA directs the type of modification catalyzed by the recombinase: directly orientated sites lead to excision of intervening DNA, while inverted sites cause inversion of intervening DNA. In certain embodiments, mutated recombinase sites may be used to make recombination events irreversible. For example, each recombinase target site may contain a different mutation that does not significantly inhibit recombination efficiency when alone, but nearly inactivates a recombinase site when both mutations are present. After recombination, the regenerated recombinase site will contain both mutations, and subsequent recombination will be significantly inhibited.

Recombinases useful in the present invention include, but are not limited to, Cre and Flp, and functional variants thereof, including, for example, FlpL, which contains an F70L mutation, and Flpe, which contains P2S, L33S, Y108N, and S294P mutations. Cre or Flpe is preferably used in ES cells, since they have been shown to excise a chromosomal substrate in ES cells more efficiently than FlpL or Flp (Jung, S., Rajewsky, K, and Radbruch, A., (1993), Science, 259, 984).

TCblR knockout cells and animals of the invention may be used for a variety of purposes, including the analysis of TCblR function, and generating cell and animal models of Cbl deficiency, for example. In addition, the conditional knockouts may be used to identify the role of TCblR at different stages of development or in different tissues, for example. The invention also provides methods of using the knockout cells and animals to analyze the function of compounds, including, for example, small molecules, and methods of screening compounds to identify new drugs or new pharmaceutical indications for known drugs. In related methods, the invention provides a means to identify a compound that inhibits or enhances the activity of a TCblR.

The invention also provides a high throughput screening assay to identify and select for compounds that effect the activity of TCblR.

EXAMPLES

Example 1

Purification and Characterization of the Transcobalamin Receptor

This example describes the purification and characterization of the TCblR protein.
Purification of TCblR The initial protocol for the preparation of placental membranes, solubilization of TCblR and affinity purification was based on the original procedure of Seligman and Allen except for the use of aminopropyl-Cbl coupled to Sephacryl or Emphaze matrix on which rabbit TC was immobilized. This purification yielded a product that was only 25% pure based on functional activity and multiple protein bands were identified by LC-MS in the region corresponding to the expected size of TCblR when separated by SDS-PAGE and stained with Coomassie blue.

A facile functional assay to monitor the TC-Cbl binding activity of TCblR proved very useful to follow the progress during purification. This assay utilized either wheat germ agglutinin (WGA) or concanavalin A (Con A)-agarose to bind TCblR. This method takes advantage of the carbohydrate content of TCblR which binds to these lectins and TC, a non-glycosylated protein that does not.

[$^{57}$Co]Cbl-TC (10,000 cpm) was incubated with 1-2 ul of each fraction in 500 ul of buffer at 4° C. and after 1 h, 100 ul of a 50% suspension of Con A-agarose was added and the incubation continued for an additional hour with constant mixing. One ml of buffer was added to each tube, and the agarose pelleted at 1000 rpm for 5 min, washed once with 1 ml buffer and the radioactivity in the pellet determined. Less than 2% of the radioactivity was associated with the agarose in 10 mM EDTA or when the TCblR is excluded from the reaction. Assay for functional TCblR activity in fractions eluted from the affinity matrix shown in FIG. 6.

Conventional protein purification techniques such as chromatography on anion and cation exchange columns, ConA and wheat germ lectin-agarose matrix and 2D SDS-PAGE did not produce results to indicate that sufficiently pure TCblR suitable for sequence analysis was obtained. One major concern during these multiple purification steps was loss of functional activity, which made it difficult to confirm the identity of the final product. One option considered was to reapply the material eluted from the first affinity matrix to another TC-Cbl matrix. For this protocol it is essential to recover functional receptor during earlier steps of purification. At this stage the procedure for solubilization and affinity chromatography was reviewed, since the first major loss of functional activity was observed in the TCblR eluted from the affinity matrix with 10 mM EDTA. This loss could not be fully restored by extensive dialysis or using a 10 fold molar excess Of $Ca^{++}$.

Further evaluation of this phenomenon indicated that 1) addition of $Ca^{++}$ was not necessary to measure functional TCblR and addition of $Ca^{++}$ did not increase this activity indicating that the TCblR as present in the placental membrane was fully saturated with $Ca^{++}$, and 2) EDTA decreased the TC-Cbl binding with complete inhibition at a 10 mM concentration. This inhibition could not be reversed by incubating the sample with a 2 fold molar excess of $Ca^{++}$ for 1 hr. Higher $Ca^{++}$ at 50 and 100 mM by itself affects TCblR activity to some extent. It appears that EDTA displaced the $Ca^{++}$ and binds tightly to that site so that $Ca^{++}$ could no longer displace the EDTA. In an attempt to develop a different elution protocol, high and low pH, high salts and mild chaotropic conditions were tried. One protocol that provided efficient elution of TCblR from the affinity matrix and did not cause loss of activity was 0.5M $MgCl_2$ in 20 mM Tris, pH 7.5. Full functional activity was recovered by diluting the eluted material to <1 mM $MgCl_2$ or by dialyzing overnight. To improve the recovery of soluble receptor from placental membranes, a number of detergents were tested. One cost effective detergent that provided soluble. TCblR comparable to CHAPSO was Empigen BB, a zwitterionic detergent at 0.5% concentration. Using this modified protocol for solubilizing TCblR and eluting from the affinity matrix, a three-step purification protocol was developed, using different affinity matrixes to obtain TCblR in its final purified form.

a. First Affinity Purification

Figure 1C:
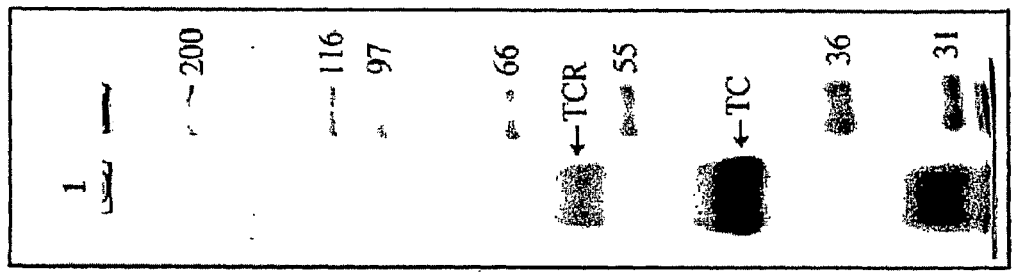
Figure 1B:
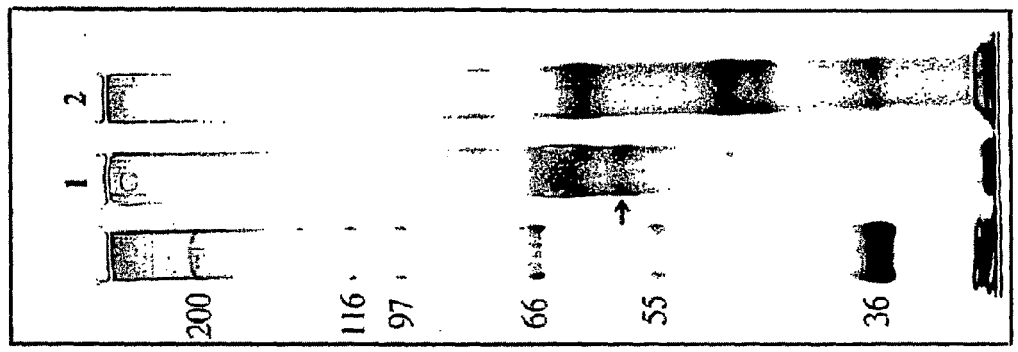
Figure 1A:
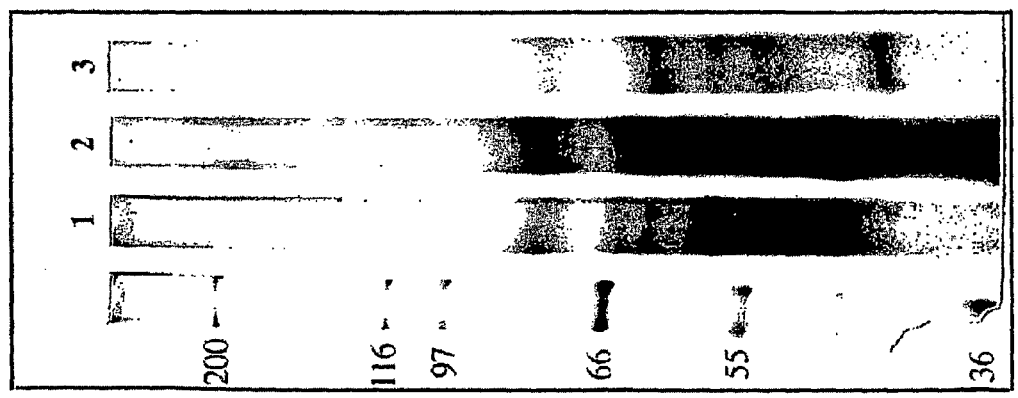

Placental membranes were prepared as described earlier, but without the EDTA washes, and solubilized in 3 volumes of 0.5% Empigen/20 mM Tris/150 mM NaCl, pH 7.5. The 100,000 g supernatant fraction (each 300 ml aliquot) was mixed with 10 ug rhTC (representing a 6 fold molar excess of TC) presaturated with 10 fold molar excess B12. After 4-6 hr at 4° C., the affinity matrix (monoclonal antibody to human TC covalently coupled to Sepharose) was added and mixed end over end overnight at 4° C. The mAb chosen for this matrix was a high affinity binding mAb that did not interfere with the receptor binding site or the Cbl binding site. This mAb efficiently captured the TC in solution and in doing so, captured the TCblR-TC-Cbl formed. The matrix was washed as described earlier except for two additional washes with 0.2 and 0.5 M NaCl and two washes with 0.1 and 0.2M $MgCl_2$ prior to elution with 0.5M $MgCl_2$. FIG. 1A shows three separate preparations in an 8% SDS-PAGE and the proteins visualized by silver staining. There were a number of protein bands in these preparations. Reapplying the eluted TCblR to the anti-TC affinity matrix or to the TC-Cbl-Emphase matrix and analyzing the samples as described for FIG. 7A improved the purity as shown in FIG. 1B, lane 1 (lane 2 shows proteins that did not adhere to the affinity matrix upon the second application). However, there were 4-5 bands in the proximity of the putative receptor band (arrow).

b. Second Affinity Purification

Figure 2:
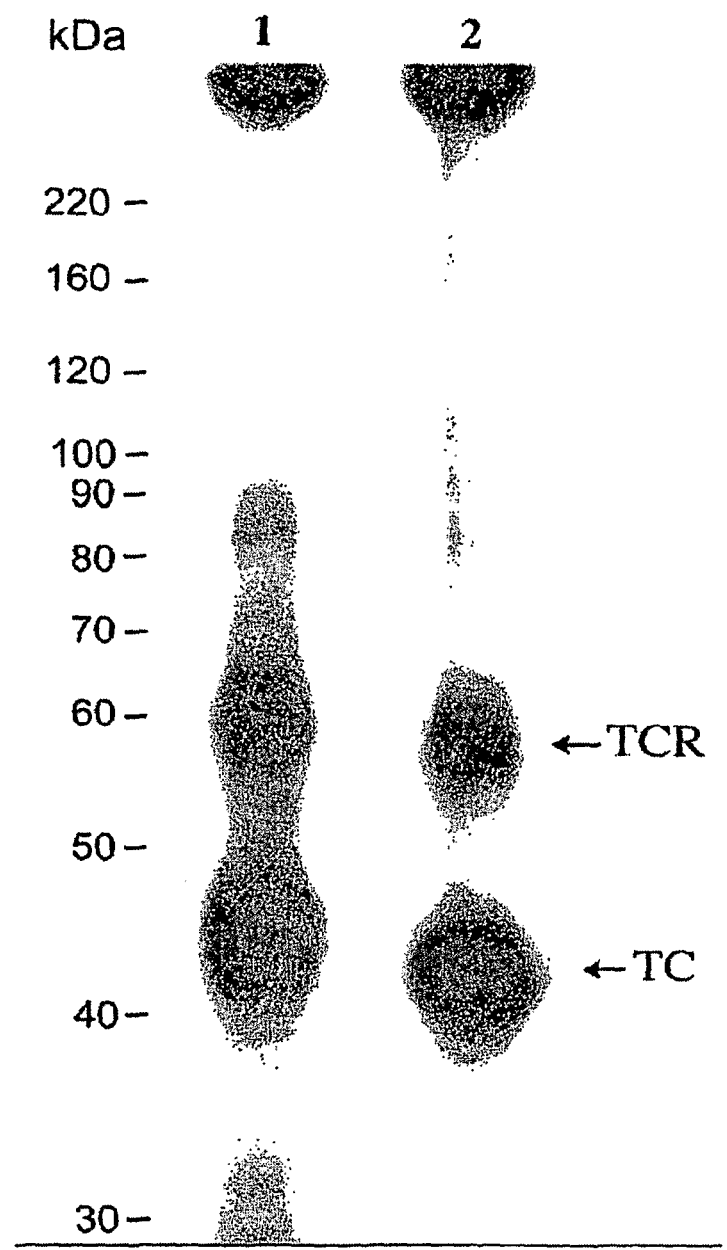

From the initial affinity purifications, it appeared that a large number of proteins were sticking to the matrix nonspecifically or by a $Ca^{++}$ dependent mechanism and were eluting with EDTA. In order to circumvent this problem, a different elution procedure was used. A small aliquot of the eluted TCblR from the first affinity purification was applied to 50 ul of aminopropyl Cbl-TC affinity matrix, washed and the TCblR released from the matrix by photo-dissociation of the TC-Cbl instead of the EDTA elution. This procedure released both TC and TCblR as a complex and the affinity matrix cannot be reused. The photo-dissociated protein was iodinated and analysed by SDS-PAGE (7.5% gel). As shown in FIG. 2, the protein released by photo-dissociation contained two major proteins, a 45 kDa protein corresponding to TC (labeled TC) and a 58-60 kDa protein, presumably the TCblR (labeled TCR). This protein has a similar molecular weight under both reducing (lane 1; 1 mM DTT) and non-reducing (lane 2; without DTT) conditions.

The procedure described above was scaled up for purification of additional TCblR. The affinity matrix was prepared by mixing overnight 1 ml of the aminopropyl-Emphaze with 0.5 mg of partially purified apo rhTC. This resulted in >90% of the TC on the matrix. The matrix was extensively washed with buffers including IM NaCl. The eluted fractions from the first affinity matrix were assayed for functional activity, pooled, dialyzed and mixed with the second affinity matrix overnight. The matrix was recovered, washed with buffers and the TCblR-TC-Cbl complex was released by photo-dissociation of the Cbl from the matrix.

c. Third Affinity Purification

The material from the above purification was applied to ConA agarose matrix. Two objectives of this third purification step were to remove most of the free TC in the photolysed sample, since a large excess TC-Cbl was expected in this sample, because all the TC on the matrix would be released by this procedure, and to then elute the TCblR from the matrix, thus adding an additional purification step. The protein recovered from the second affinity step was mixed overnight with 0.5 ml Con A agarose, washed with buffers and then incubated with 1 ml of eluting buffer containing 0.4 M each of a-methyl-D-mannoside and Maltose in 20 mM Tris pH 7.5/5 mM CHAPSO for 4 hours. The matrix was transferred to a small column, the buffer was collected and the matrix was washed with another ml of the same eluting buffer. This sample was dialyzed, concentrated and separated in an 8% SDS-PAGE gel (FIG. 1C). As can be seen, a single homogeneous band of ~58-60 kDa was observed by coomassie blue dye staining. The band was excised, digested with trypsin and analyzed by LC-MS. Peptide peaks were subjected to further MS-MS analysis to yield AA sequences.

Identification and Characterization of TCblR

A data base search for sequences using Mascot (Matrix Science) matched the 4 peptide sequences obtained (underlined in FIG. 3) with 100% identity and a probability based Mowse score of 200 indicating a definite match with a data bank protein now identified as TCblR. The amino acid sequence of human TCblR is provided in SEQ ID NO:1.

Figure 4:
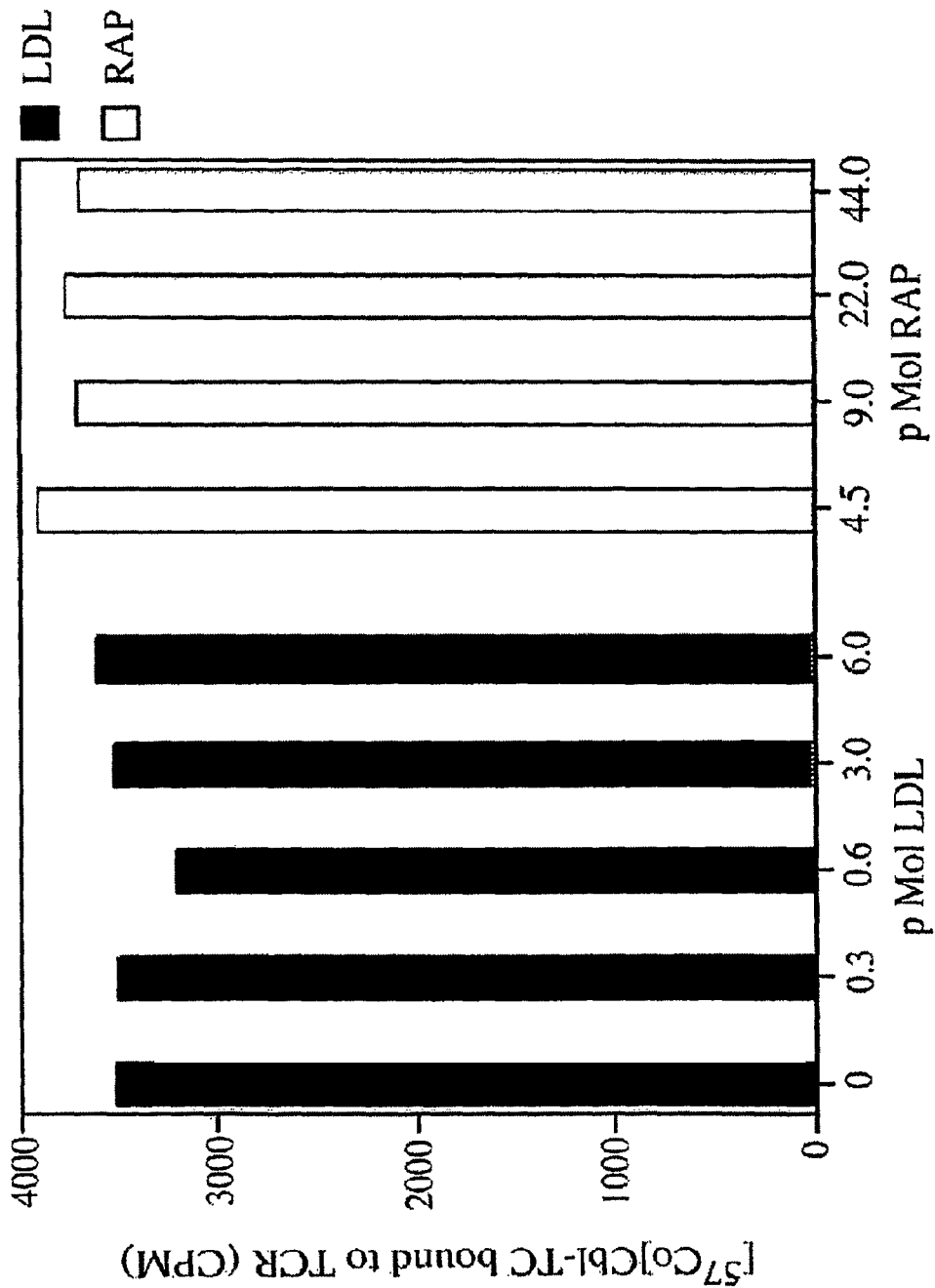
FIG. 4 is a graph depicting the binding of radiolabeled TC-Cbl to TCblR (TCR) preincubated with the indicated amounts of either LDL (black bars) or RAP (white bars).

Based on the predicted amino acid sequence, it is evident that TCblR belongs to the LDL receptor family with 2 LdL receptor type A domains, a calcium binding domain, a 31AA signal peptide a 198AA extracellular region, a transmembrane sequence of 24AA and a cytoplasmic domain of 29AA. Many of the LDL receptor like proteins are multiligand binding proteins. However, TCblR appeared to be specific for TC-Cbl, since it did not bind intrinsic factor or haptocorrin (data not shown). Unlike many of the LDL receptor like proteins, the binding of TC-Cbl to TCblR was not affected by 20-400 fold molar excess of LDL or a 300-3000 fold molar excess of receptor associated protein (RAP) (FIG. 4), a protein involved in the regulation of ligand binding. The TCblR protein was heavily glycosylated and, in addition, had potential sites for phosphorylation and myristylation.

Example 2

Figure 5:
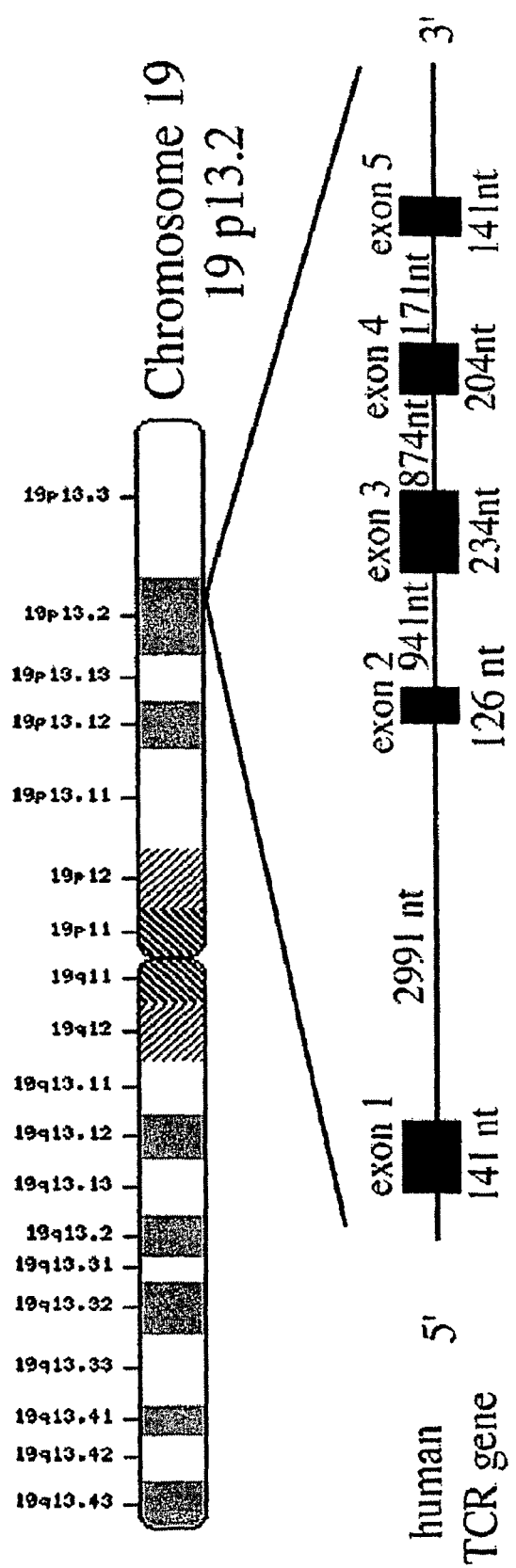
FIG. 5 is a schematic diagram of human chromosome 19, which indicates the chromosomal location and gene structure of human TCblR.

Identification and Characterization of the Transcobalamin Receptor cDNA and Gene A search of the human genome data bank revealed the complete gene sequence and chromosomal localization of the human TCblR gene (FIG. 5). The cDNA sequence of human TCblR is provided in SEQ ID NO:2.

Identification of Cis Genomic Elements that Regulate TcblR Expression

Since TCblR expression is regulated with maximum expression in actively dividing cells, this differential expression is used to characterize transcriptional regulation of this gene and to identify trans-active factors involved in this regulation. Studies on the level of TCblR transcript and protein expression in various primary cell lines such as peripheral skin fibroblasts, venous endothelial cells and in malignant cells such as K562, HL 60 and ECV 304 provide information on the precise time frame for high- or low-TCblR expression and TCblR expression throughout the cell cycle.

The regulation of TCblR expression is analyzed as described below by identifying the up stream regulatory elements in the 5' flanking region of the TCblR gene. Shown in FIG. 10 is the 1022 bp 5' sequence of the human TCblR gene. This region contains numerous identified motifs to which known trans-active factors bind. The minimum 5' sequence required for promoter activity is determined by testing the whole 3000 bp fragment and the 1000 bp fragment immediately upstream of the ATG start site separately in a reporter gene construct containing the chloramphenicol acetyl transferase gene (CAT) gene. If no change in promoter activity is observed, it is fair to assume that all the control elements are located in the 1000 bp immediate 5' region of the TCblR coding sequence and this region is subjected to additional analyses to identify both positive and negative cis elements involved in TCblR expression. If a decrease in promoter activity is observed by deleting the 2000 bp 5' region, this fragment is additionally tested for enhancer activity by cloning in a pCAT enhancer plasmid.

Analysis of Cis Acting Elements in the Promoter

In order to identify the minimum promoter required for activity, shorter fragments with 5' end deletions with restriction enzymes or nested deletions from the 5' end are constructed and tested for promoter activity. This strategy also provides information on regions involved in up or down-regulation of the gene. Once a sequence motif and the transcription factor specific for this sequence has been identified, confirmation of the role of this transcription factor in regulating the TCblR promoter is obtained by cotransfecting a plasmid containing the cDNA encoding the transcription factor along with the promoter-reporter construct.

Further proof of DNA/protein interaction is obtained by the following experiments.

i) DNase I foot-printing: The procedure of Brenowitz (*Short Protocols in Molecular Biology*, New York, N.Y., John Wiley & Sons, p12. 10-12.16, 1992) is used to identify DNA sequences protected from DNAse I digestion. For these studies, a plasmid containing the fragment from the promoter region is linearized with a restriction endonuclease that cuts at a single site. The linear plasmid is end labeled with $\alpha$-[$^{32}$P]-dNTP using the klenow fragment of DNA polymerase or end-labeled $\gamma$-[$^{32}$P]ATP and T4 polynucleotide kinase, digested with a second restriction and the TCblR sequence containing fragment is recovered by agarose gel electrophoresis. A titrated amount of DNAse I is used to digest the end labeled DNA fragment ($\sim$5-10$\times$10$^5$ cpm) in the presence and absence of nuclear proteins, separated by PAGE and identified by autoradiography. This identifies regions in the sequence protected from digestion by DNAse I by virtue of a nuclear protein binding to the specific sequence. The nuclear extracts prepared as described by Henninghausen and Lubon (*Methods in Enzymology*, 152:721-735, 1987) are obtained from cells in early log phase of growth and from confluent non-dividing cells to identify differences in protected sequences that may provide information on factors that up-regulate TCblR expression during the proliferative phase of cell growth.

ii) DNase I hypersensitivity: The assay of Tuan and London (*Proc. Natl. Acad. Sci. (U.S.A.)*, 81:2718-2722, 1984) is used to identify transcriptionally active regions 5' of the transcription start site. The transcriptionally active regions attain an open chromatin conformation prior to initiation of transcription which renders these regions susceptible to digestion with pancreatic DNase I. For these studies, nuclei are isolated from early log phase cells and non-dividing cells. The nuclei will be incubated with varying concentrations of DNase I, the DNA extracted and digested with appropriate restriction endonucleases to cut the DNA in specific regions to generate predicted size fragments. The digested DNA is separated by PAGE and analyzed by Southern blotting using oligonucleotide probes to the 5' and 3' end of the predicted size fragment. If indeed there is a region within this fragment that renders it hypersensitive to DNase, the Southern analysis will identify two smaller fragments that vary in size depending on the region that was sensitive to DNase 1.

iii) Transcription start site: In order to precisely locate the initiation of transcription, RNase protection assay and 5' RACE is used. The latter assay provides a product that can be subjected to sequencing to provide the exact nucleotide at which transcription is initiated. The RNase protection assay provides an approximate size of the protected fragment from which the transcription start could be deduced. This assay also identifies multiple transcription initiation sites if present.

iv) Electrophoretic mobility shift assay (EMSA): Once the protected regions within the promoter are identified, complementary pairs of oligonucleotides ($\sim$30-50 nt) are synthesized to encompass the putative DNA region. These oligonucleotides are end labeled with $\gamma$-[$^{32}$P]ATP and T4 polynucleotide kinase to serve as probes in the EMSA assay. Nuclear protein extracts from cells actively expressing the receptor are incubated with radiolabeled probes and analyzed by PAGE to identify probes that migrate slower due to DNA-protein complex formation. Non-specific binding is reduced by adding a pre titrated quantity of poly dI-dC and the specificity of interaction is determined by competing out the binding with unlabeled specific DNA fragment. The region within the probe is further identified either by constructing shorter probes (keeping in mind that protein binding may require 2-4 nucleotides on either side of the binding motif) or by making smaller fragments that overlap by 6-10 bases and using these in the competition assay or direct binding assay. Once a specific sequence is identified as a motif to which transcription factor(s) bind, and if this transcription factor is a known protein, the availability of antibodies to these proteins allow super-shift analysis of the DNA-protein complex to confirm the identity of the specific transcription factor.

Translational Regulation of TCblR Expression

The amount of a specific protein synthesized in a cell is a function of steady-state concentration of the mRNA and the rate of translation of the mRNA into protein. The initiation of transcription under control of upstream regulatory elements and trans-active factors is an essential first step in generating the primary transcript, which is then processed into mRNA and translated into protein. Thus, at any steady state, the rate of transcription of the RNA is equal to the rate of decay of the mRNA, and both kinetic parameters can be quantified respectively, by a nuclear runoff assay of transcript synthesis and the rate of mRNA decay. The turnover rate (T1/2) of the receptor protein is an important parameter that is quantified by metabolic radio-labeling of the nascent protein.

Rate of Transcription and Stability of TCblR mRNA

The rate of transcription during high TCblR expression and during down-regulation of TCblR is determined by nuclear runoff assay of nuclei isolated from cell lines in culture. This system allows the to evaluation of the effects of culture conditions and other factors such as B12 replete or B12 deficient or the TC-Cbl concentration in the culture medium that may affect TCblR synthesis. At steady state, only the rate of transcription or the rate of mRNA decay need be determined since they must be equal. However, analysis of both parameters during up or down regulation of receptors provides additional information regarding transcriptional and translational events that may precede receptor expression and indicate which of the two processes initiates any change in TCblR expression. A mathematical analysis using an integrated kinetic equation to calculate mRNA turnover has been provided by Harrold et al. (*Anal. Biochem.*, 198:281-292, 1991) and an integrated kinetic equation for analysis of steady state data has been provided by Greenberg (*Nature*, 240:102-104, 1972).

The standard protocol for measuring mRNA decay is to block transcription with actinomycin D or 5,6 dichloro1-β-ribofuronosyl benzimidazole and then measure the rate of disappearance of the mRNA by northern blotting of total cellular RNA. Real-time quantitative PCR is used to quantify mRNA in cells. This method is faster and provides better quantification of mRNA than northern blotting.

The information obtained is unique to the TCblR gene and is an essential component of structural and functional understanding of this gene.

Example 3

Characterization of Transcobalamin Receptor Expression in Human Tissues

The availability of gene probes and antiserum to TCblR facilitate direct identification of the TCblR mRNA transcript and protein in tissue sections, respectively, by in situ hybridization and immunohistochemistry.

The techniques for both procedures are well established. Polyclonal antiserum specific for TCblR was obtained from R&D Systems (goat anti-human 8D6 polyclonal antibody; Minneapolis, Minn.). The polyclonal antiserum to TCblR reacts well in immunohistochemical analysis as shown in FIG. 18. NIH IMAGE software and a phosphor-imager were used to quantify the autoradiographic signal, or the fluorescence signal intensity in tissue sections.

Tissues for these analyses are obtained from commercial sources for tissue arrays because these have been collected under controlled conditions and tested for integrity of proteins and mRNA using specific markers. The utility of tissue microarrays in normal and tumor tissues has been well demonstrated. The in situ hybridization and immunohistochemical studies determine the level of TCblR expression in various tumors as compared to the normal tissue counterpart. This analysis establishes baseline expression of TCblR mRNA and protein in various tissues and identifies tumors that overexpress TCblR as potential candidates for Cbl depletion strategy or drug targeting via the TCblR pathway. These studies further identify the structural elements involved, and the association of TCblR gene expression with cell replication in normal and cancer cells.

Example 4

Characterization of the Transcobalamin Receptor Protein

The following experiments provide information regarding the synthesis, translocation, function and fate of the receptor protein.

Studies reported thus far on the properties of the TC receptor are based on the binding and uptake of TC-Cbl. This indirect measure of the TCblR protein has defined an important function for this protein, but the synthesis, translocation and fate of the receptor, its expression during the proliferative phase of the cell cycle, and its down-regulation in non-dividing cells have remained speculative.

Rate of TCblR Synthesis

Preliminary experiments determined TC-Cbl binding at 4° C. for 1 hour in trypsin or EGTA treated K562 cells. Cells treated with trypsin had fewer receptors than EGTA-treated cells (this provides a measure of surface receptors) (data not shown). However, the rate of appearance of new receptors on the cell surface was similar in both samples. These preliminary studies provided a measure of TCblR expression and the rate of appearance of new receptors on the cell surface.

These studies are extended by pulse-chase labeling of nascent TCblR with [$^{35}$S]methionine to determine the rate of TCblR synthesis. Cells in culture are first depleted of endogenous methionine by incubation in methionine free medium. [$^{35}$S]methionine is then added to the culture and the, incubation at 37° C. continued for an additional 60 min followed by the addition of unlabeled methionine containing complete medium. At various time intervals, an aliquot of the cells is removed, washed and solubilized in CHAPSO detergent. The soluble fraction is incubated with antiserum to TCblR to immunoprecipitate the [$^{35}$S]methionine labeled protein which is then analyzed by SDS-PAGE and autoradiography. Another aliquot of the cells is treated with trypsin to remove surface bound protein and the cell pellet is then analysed as described above. The difference in the amount of TCblR in the two cell aliquots provides a measure of TCblR on the cell surface. Culturing the cells in the presence of cycloheximide to inhibit protein synthesis and then quantifying the decrease in the [$^{35}$S]methionine labeled protein over time indicates the rate of decay or the turnover rate for the receptor protein.

Cell Cycle Association of TCblR Expression

Figure 11:
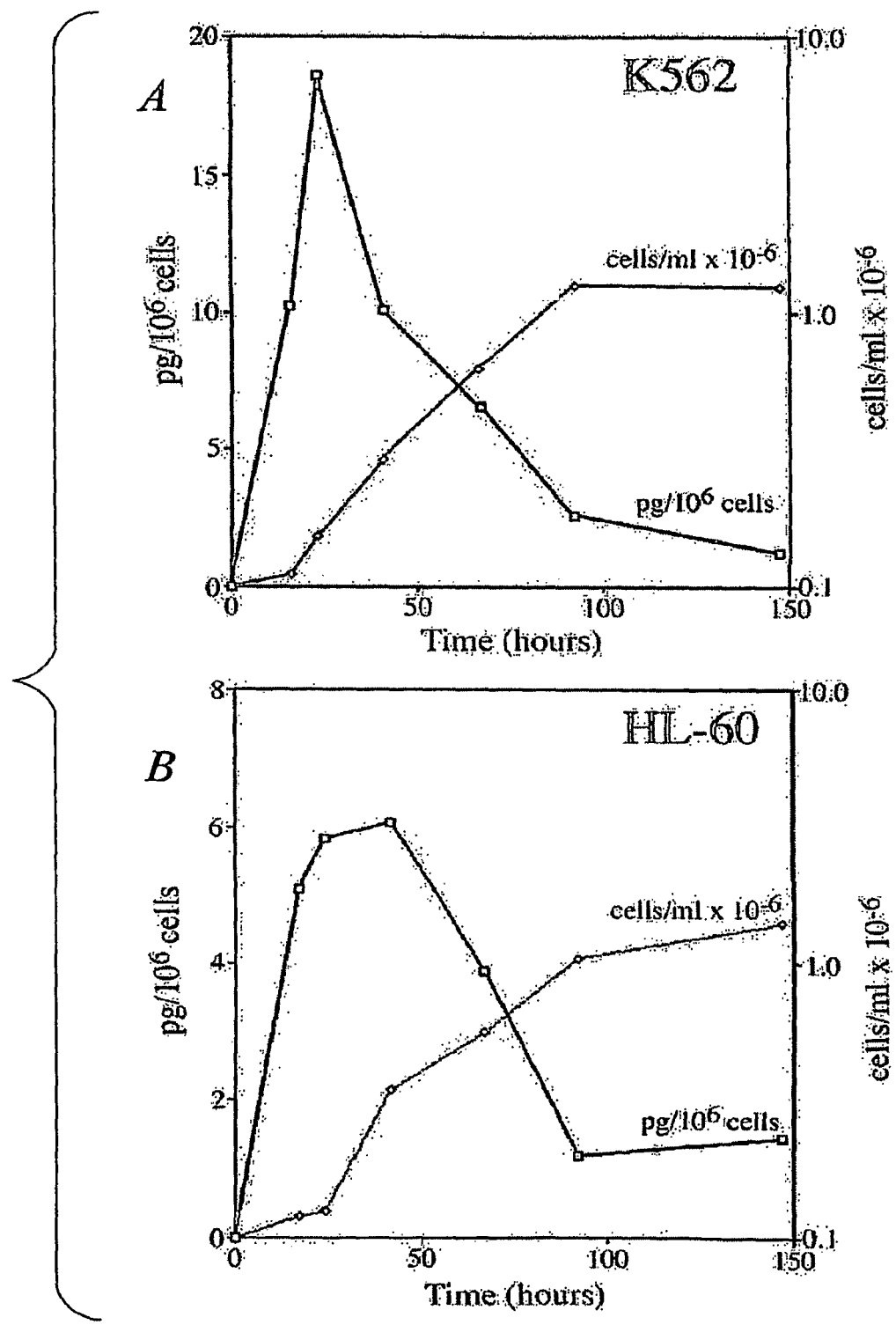

It is clear that the TCblR protein is heavily glycosylated with carbohydrate accounting for roughly 50% of the mass and, therefore, must be processed through the ER and Golgi before it is targeted to the plasma membrane. TCblR expression during the cell cycle was examined using radiolabeled TC The appearance of receptors on the cell surface increased and peaked during the first 12-30 hr in culture depending on the doubling time of the cell. The receptors decreased as the cell density increased, and the percent of dividing cells in culture decreased with fewer than 200 functional receptors per cell in confluent cultures. This was determined by incubating cells with [$^{57}$Co]Cbl-TC using K562 and HL-60 cells in culture (FIG. 11).

In order to associate receptor expression with the precise phase of the cell cycle, cells are analyzed by flow cytometry for cell surface TCblR expression using an antibody to the extracellular domain of TCblR followed by a second antibody conjugated to fluoroscine isothiocyanate (FITC). The cells are fixed in ethanol and incubated with propidium iodide to stain the DNA. Since propidium iodide can also stain RNA, the cells are treated with RNase to degrade endogenous RNA. Flow cytometric analysis of these cells sorts the cells in various phases of the cell cycle and the receptor density in these cells is quantified by the FITC fluorescence associated with these cells. For these studies, cells are collected at various time intervals after seeding in culture and subjected to the flow cytometry. This analysis identifies cells expressing TCblR within a mixed population of cells and also identifies the precise phase of the cell cycle that these cells are in, when TCblR expression is highest. Dual labeling with cyclin specific antibodies further identifies the association of TCblR with the cell cycle.

The cell cycle is synchronized by culturing cells in the presence of 5-bromo-2-deoxyuridine and in the presence of specific inhibitors of cell cycle to evaluate the effect of these manipulations on TCblR expression. This experimental strategy is extended to various neoplastic cell lines in culture to identify cancers suitable for targeted delivery of chemotherapeutic drugs and imaging agents coupled to Cbl or fluorescent Cbl compounds, as well as direct manipulation of TCblR to inhibit cellular uptake of Cbl and block cell proliferation.

Not much is known about what regulates TCblR expression. For example, it is not known if intracellular Cbl concentration or extracellular TC-Cbl provide feedback signaling to regulate TCblR expression, or if cell cycle signaling molecules provide the necessary signals to regulate TCblR expression. The studies described herein, with [$^{35}$S]methionine labeling of TCblR in cells or quantifying receptors on the cell surface with antibody labeling, allow the evaluation of the role of extracellular and intrinsic factors in TCblR expression.

There are potential phosphorylation sites in the extracellular as well as intracellular domains of TCblR. Extracellular membrane kinases or intracellular cyclin dependent kinases may be involved in regulating the uptake of TC-Cbl. Whether other signaling events regulate this process or if this process controls the expression of signaling molecules is evaluated by manipulating the culture conditions. Evidence in support of TCblR involvement in signaling comes from studies in which anti TCblR antibody was shown to block the proliferation of germinal center B-cells when co-cultured with dendritic cells. Signaling by dendritic cells is required for this process. Similar effects were observed when Burkitt lymphoma L3055 cells were cultured with follicular dendritic cells HK and an antibody to TCblR that appeared to block signaling by HK cells. It is not clear from these studies if inhibition of signaling molecules by blocking TCblR or if intracellular Cbl deficiency due to a blocked TCblR contributed to the lack of signaling by dendritic cells or directly contributed to inhibition of B-cell proliferation. If indeed a role in signaling events and release of cytokines is demonstrated for TCblR, the strategy to inhibit cancer cells by blocking TCblR may be more effective in combination with depleting intracellular Cbl.

Binding, Internalization and Disposition of TC-Cbl

The TC receptor belongs to the family of LDL receptor like proteins and is likely to have properties similar to many of these receptors for ligand uptake and disposition. Many of these receptors have been well characterized and provide the basic framework to model our studies of the TC receptor with well tested techniques.

The previous understanding of Cbl uptake into cells was derived from a few studies that measured uptake of radiolabeled TC into cells or by the binding of latex beads containing TC-Cbl. These studies provided evidence for the existence of a membrane receptor for the uptake of TC-Cbl. However, the structural and functional determinants of this receptor, factors regulating the uptake of TC-Cbl and the fate of the receptor in the process of ligand uptake and disposition are not known. The availability of the cDNA and gene encoding TCblR and a polyclonal antiserum to this protein, provide the tools to directly examine in detail the synthesis, processing and turnover of this protein and the process by which it mediates Cbl uptake by receptor mediated endocytosis.

Example 5

Characterization of Transcobalamin-Cobalamin Binding to the Transcobalamin Receptor Characterization of TC-Cbl binding to TCblR There is very little information on the binding affinity of TCblR for TC as a holo protein (as TC-Cbl) and as the apo protein. Previous studies suffer from methodological limitations and on the estimates of apo and holo TC used in the binding studies. Based on the earlier reports of a two fold lower affinity of apoTC for the receptor, under physiological conditions where the apo TC accounts for ~80% of the plasma TC, the system would be very inefficient in transporting Cbl into cells. One explanation for the earlier results could be that these studies used serum as the source of apo TC and the results could have been affected by endogenous holo TC. Even if a correction was applied, the estimate of holo TC in the sample may not have been accurate because a direct assay for holo TC was not available.

In order to better characterize TC binding to TCblR, these studies have been repeated using purified TCblR and recombinant TC. As shown in FIG. 12, there is a 28-fold difference in the affinity of holo and apo TC. This difference is sufficient to allow for the preferential binding and uptake of holo TC.

Studies using the recombinant extracellular domain of TCblR showed similar specificity for holo TC indicating that a complete protein or its native orientation in the plasma membrane is not required for ligand binding. However, glycosylation may be necessary because the functional extracellular domain produced in mouse myeloma NSO cells is fully glycosylated. Binding of purified TCblR, as well as the recombinant extracellular fragment, has been determined. The complete protein binds to both wheat germ as well as con A lectin, whereas the extracellular fragment only binds to wheat germ which has specificity for the N-linked oligosaccharides containing N-acetylglucosamine and to a lesser extent to sialic acid residues. These results indicate that ConA binding is restricted to the membrane and cytoplasmic domain of TCblR and therefore this region contains core oligosaccharides with linked mannose residues.

In order to further define the structural elements of TCblR required for TC-Cbl binding, the following experiments are carried out:

i) The extracellular fragment of TCblR is deglycosylated with neuraminidase and endoglycosidases as previously described and tested for TC-Cbl binding. Shorter fragments of this protein, as shown in FIG. 13, are also tested. These fragments are separated by HPLC and tested for TC-Cbl binding. It is likely that the fragments may not bind with high affinity but may contain a portion of the peptide required for binding. This is tested by competing a 10, 100, and 1000 fold molar excess of a fragment or mixture of these for inhibition of TC-Cbl binding to TCblR. Further identification of the shortest region of the peptide sequence involved in binding is deduced by competing shorter overlapping synthetic peptides in the binding assay.

ii) Another approach is to form the complex of holo TC and TCblR, crosslink the complex with one or more crosslinking compounds, digest with trypsin and analyze the tryptic fragments by LC-MS. The crosslinked peptides are identified from the sequence data generated. The advantage of this approach is that multiple sites of interaction due to conformation of the protein are identified.

These techniques were applied to identify the receptor-binding domain of TC. In this case, we used epitope specific monoclonal antibodies to TC that block the binding of TC to TCblR. A structural representation of human TC with the potential region involved in binding to TCblR is shown in FIG. 14. The deduced structure of the extracellular domain of human TCblR (SwissModel prediction) is also shown in FIG. 14. The studies described above provide the information to explain how TC-Cbl docks into the receptor and what regions are critical to this interaction. This information is used for designing neutralizing peptides and generating mAbs that block the binding of TC-Cbl.

Example 6

Characterization of Cellular Uptake of Transcobalamin and Transcobalamin Receptor Radiolabeled TC and TCblR are used to monitor the fate of these two proteins in the process of Cbl uptake into cells. The use of iodinated protein is not appropriate because the loss of iodine due to halogenases makes it difficult to monitor the protein. $^{35}$S-Met labeled TC is produced in the baculovirus system used for producing rhTC (Quadros, E. V. et al., *Blood*, 81:1239-45, 1993). Replacing the culture medium 48 hr after infecting insect cells with recombinant virus yields adequate quantity of $^{35}$S-met labeled TC in as little as 2-4 hr. Radiolabeled cellular proteins are used by culturing cells in $^{35}$S-met. The radiolabeling of cellular proteins, specifically TCblR, is optimized by extending the duration of cells in methionine free medium without compromising cell viability and then optimizing the amount of radio-labeled methionine and the duration of incorporation.

For following the pathway of TC-Cbl internalization, $^{35}$S-met-TC is saturated with Cbl, and incubated with K562 cells at 37° C. for 30, 60, 120 and 240 min. At each time point, cells are collected, washed and TC associated with the outside of the cell (EGTA releasable), membrane associated TC (plasma membrane and other cellular membranes solubilized with detergent), and the soluble component is determined by immunoprecipitation. The immunoprecipitated radioactivity is analyzed by SDS-PAGE to identify intact protein and degraded fragments that still bound to the antibody. This provides a time course for the binding, uptake, internalization, degradation of TC and release of Cbl in the cell. An identical aliquot kept on ice serves as the control.

For monitoring the fate of TCblR, the same time course and protocol is followed except for the use of unlabeled TC-Cbl as the ligand and anti TCblR ab to immunoprecipitate the receptor protein. Trypsin releasable TCblR from intact cells indicates TCblR associated with the outside of the cell and membrane bound radioactivity is due to ER, Golgi and lysosomes.

In a parallel experiment, in addition to $^{35}$S-Met labeling, intact cells are labeled with biotin to biotinylate cell surface proteins. The cells are analyzed as described above to determine $^{35}$S-TCblR (by binding to anti-TCblR Ab) and the biotinylated fraction of this (by binding to avidin). This analysis provides information on recycling of receptors if during the 4 hr (or longer if needed) time course, the biotin-TCblR decreases on the cell surface, appears in the intracellular compartments and the reappears on the cell surface.

Inhibitors of receptor recycling, glycosylation and lysosomal processing are used to identify the pathway of TCblR translocation to the plasma membrane as well as internalization and recycling. For example, incubating cells with lysomotropic compounds such as methylamine and chloroquine indicates if TCblR is processed in the lysosome to degrade TC and release the Cbl. The calcium ionophore monencin blocks protein release from the Golgi and affects receptor recycling. Sulfonamides with proton ionophore activity inhibit ATP hydrolysis, elevate endosomal and lysosomal pH and affect receptor recycling. Trifluopipezarine, an inhibitor of calmodulin dependent enzymes and phospholipid dependent C-kinase is an inhibitor of both endocytosis and recycling. The use of these compounds to define the pathways of protein trafficking both in and out of cells is well documented and will be utilized to define the TD TCblR pathway for Cbl uptake into cells.

Protein phosphorylation is also involved in receptor recycling. A preliminary analysis of the primary structure of TCblR suggests potential phosphorylation sites. Signaling via the cyclin dependent kinases is investigated with respect to ligand binding, internalization and downregulation. The application of immunohistochemical analysis complements the biochemical studies.

These studies delineate the pathway of TCblR synthesis, translocation, ligand binding and the fate of the receptor following ligand internalization, thereby providing information essential to utilizing this receptor to either block the uptake of TC-Cbl or to deliver drugs, radioisotopes or imaging compounds to tumors.

Example 7

Effects of Inhibiting Transcobalamin Receptor Expression Using siRNA

B12 deficiency leads to megaloblastic anemia and neurologic disorders in the form of subacute combined degeneration of the spinal cord, peripheral neuropathy and CNS abnormalities. The hematologic abnormalities are similar to those in folate deficiency and can be explained on the basis of folate requirement for DNA synthesis and the entrapment of methyl-folate in B12 deficiency. However, the biochemical basis for the neuro-pathologic changes in B12 deficiency has remained an enigma because of the difficulty in producing B12 deficiency either in culture or in an animal model. The knockout of the TCblR gene provides cell and animal models in which the effects of B12 deficiency could be produced rapidly by virtue of the only pathway for transporting B12 into cells being inactive. It also allows the study of the effects of this gene knockout on embryonic development, especially the nervous system.

Inactivation of TCblR Gene Using Small Interfering RNA (siRNA)

Gene silencing by siRNA interference (RNAi) has proven to be effective in targeting specific genes for inactivation, especially in cell culture systems. The advantage of this system is that it is carried out under a variety of culture conditions to study the effects of inactivating a single gene in different cell types. In addition, by designing a suitable expression vector, the siRNA is introduced into mice to silence specific genes. This is especially useful in the case of gene knockouts that are embryonically lethal and cannot be rescued. In this approach, double stranded RNAi is introduced into cells or is generated in situ by introducing a plasmid that can be induced to produce multiple copies of the sequence which is then processed by a dicer enzyme into smaller 21-23 nt dsRNA identified as siRNA. The siRNA acts as a guide sequence within a multi component nuclease complex to target complementary mRNA for degradation.

Shown in FIG. 15 are the deduced stem-loop structures of the human (A) and mouse (B) TCblR mRNA with the oligonucleotides to potential target regions. Based on GC content and absence of significant homology with other gene sequences within the respective genomes, 5 regions within the mRNA were selected for siRNA targeting. Synthetic double stranded siRNAs that have been modified to optimize their stability in vivo are introduced into cells by electroporation or by transfection and tested for their ability to block TCblR expression. These experiments will identify the best candidate siRNA for our studies. A scrambled sequence of this siRNA will serve as the control for these experiments.

The most potent siRNA is incorporated into an adeno-associated viral vector (AAV-siRNA). First, the siRNA is cloned into the silencer 1.0-U6 vector in which the U6 promoter controls siRNA expression. This construct is cloned into the AAV vector plasmid pXX-UF(136). To produce the recombinant adenovirus containing the TCblR siRNA (rAAV-siRNA), subconfluent 293 cells are cotransfected with pXX-U6-TCblRsiRNA and the AAV helper plasmid pACG2-1. The cells are then infected with adenovirus Ad5dl312 (anE1A-mutant) at a MOI of 2 and the infection allowed to proceed for 60-72 hours. The cells are harvested, lysed by freeze/thaw Cycles, the DNA in the lysate digested with Benzonase (250 U/ml) at 37° C. for 10 min: and cellular debris removed by centrifugation at 1500 g for 15 min. The cell lysate is subjected to ammonium sulfate fractionation followed by two sequential continuous CsCl gradient centrifugations. The fractions containing rAAV are pooled, dialyzed against sterile PBS, heat-treated for 45 min. at 56° C. and stored at −80° C.

siRNA Studies in Cell Cultures

The objectives of these studies are to evaluate the effects of TCblR gene silencing on various neoplastic cells and to evaluate the effect on cells in culture. One advantage of using rAAV infection is that cells can be maintained with the virus to produce siRNA for longer periods to induce metabolic and structural changes particularly when the gene knockout could be lethal. The strategy for these studies is to monitor TCblR expression and the mRNA in cells along with the level of MMA and HCY levels in the culture medium, the two metabolites expected to be elevated in intracellular Cbl deficiency and observe the effect on proliferation of malignant cells in culture. This approach allows the testing of a large number of cell lines to identify those most susceptible to TCblR gene silencing. In the case of neuronal, glial and Schwann cells, metabolic and morphologic changes indicative of Cbl deficiency will be determined. These include the ability of neuronal cells to make connections and Schwann cells to make myelin upon stimulation with Forskolin.

SiRNA Studies in Mice

Since TCblR is expressed in all tissues, the systemic effects of chronic TCblR inhibition in various organs and the vasculature is examined by intravenous administration of rAAV-TCblR. The effects of this siRNA on embryonic development is examined by administering the rAAV-TCblR to mice both pre and post pregnancy. Serum HCY, MMA, TCblR protein and mRNA are monitored as indicators of intracellular Cbl deficiency and TCblR inactivation. Tissues from these mice and fetuses are evaluated for structural changes. If indeed Cbl is essential to the developing embryo, the knockdown may produce neuropathological changes commensurate with B12 deficiency.

Example 8

Generation of Transcobalamin Receptor Knockout Mice

In recent years, gene inactivation has proven to be a powerful model to identify the function of a specific gene and its deleterious effects, both at the cellular level and in the whole organism. The TCblR gene knockout will, for the first time, provide a model to rapidly produce the neurologic as well as hematologic abnormalities of B12 deficiency in an animal model.

The mouse homolog of the TCblR gene has been cloned and the gene locus has been identified on chromosome 17. The structure of mouse TCblR gene has been defined and genomic clones as well as a BAC clone spanning the TCblR region are available. The organization of the mouse TCblR gene is shown in FIG. 16. The cDNA sequence of the mouse TCblR gene is provided in SEQ ID NO:3.

Construction of a Gene Targeting Vector for Insertion into Embryonic Stem

The mouse TCblR genomic clone is used to construct a replacement gene-targeting vector. A 0.9 kb fragment from the 5' end of gene is cut by digestion with DraIII and MU and isolated by electrophoresis in agarose gel. Another 1.6 kb fragment from the 3' end of the gene is generated by digesting the genomic clone with EcoRI and isolated. These fragments can also be generated by PCR from the genomic clone. This strategy allows the inclusion of specific restriction enzyme sites in the primers so that specific sites could be created to insert into the vector as necessary. These fragments are cloned into the target plasmid pKO followed by the insertion of the neomycin resistance gene (pKOselectNeo vector) and the negative selection marker dipthria toxin-A chain gene (pKOselectDT vector). A diagrammatic representation of the final construct is shown in FIG. 17.

The linearized target construct is introduced into 129/svev ES cells by electroporation and expanded in culture with G418 to select for neomycin resistance. Resistant colonies are selected for cryopreservation and for extraction of DNA for analysis. Genomic DNA isolated from these cells is digested with restriction enzymes and analyzed by Southern blotting using cDNA fragments corresponding to exons 1 and 2 of the mouse gene as probes to identify homologous recombinants.

These results are further confirmed by PCR using forward and reverse primers corresponding to the mouse sequence 5' of the neomycin gene and in the neomycin gene. This confirms insertion of the target vector into the TCblR gene locus of the mouse ES cells.

Generation of Chimeric Mice and Germ Line Transmission of TCblR Mutant Allele

ES cells containing one TCblR mutant allele (TCblR 4/−) are injected into 3.5 day old C57BL/6 blastocysts and surgically placed into the uterus of pseudo-pregnant CD1 mice to generate agouti mice. These animals are bred to generate mice heterozygous for the TCblR mutant allele. The presence of a mutant allele and a normal allele is confirmed by real time PCR of genomic DNA from these mice using forward and reverse primers in the TCblR gene and using a second set of primers in which the reverse primer is generated to the Ned gene. The F1 heterozygotes are mated to create F2 homozygous offsprings. Genomic DNA is be analyzed by PCR, Southern blotting following digestion with restriction enzymes and RNA from selected tissues is subjected to RT-PCR using primers to distinguish between the wild type, the heterozygous and the homozygous mouse.

Effects of TCblR Gene Deletion

Based on the biological function of B12 and its role in recycling folate, there is a high probability that the gene knockout may be lethal to the embryo. However, it is possible that embryonic lethality may not occur because megalin, a TC-Cbl binding protein may act as a surrogate receptor in the absence of TCblR. Megalin is expressed in the embryo during the early stages of development. Should the embryos fail to implant and grow, the mice are maintained on pharmacological doses of B12. This approach provides adequate B12 by diffusion and pinocytosis to maintain normal intracellular B12. Evidence in support of this strategy comes from patients with congenital TC deficiency who respond to pharmacological doses of B12.

These studies establish the effects of B12 depletion on embryonic development, especially the nervous system. Recent observation of autoantibodies to the folate receptor in women with a neural tube defect pregnancy, and in children with cerebral folate deficiency syndrome, suggest an important role for folate during early embryogenesis and during infancy. B12 deficiency indirectly affects folate status; however, the direct effects of B12 deficiency may have on embryonic development are not known. If indeed the TCblR gene knockout is lethal, homozygous mice maintained on pharmacological doses of 1) folinic acid; 2) folinic acid+B12; 3) B12 alone and 4) no vitamin supplements are included in the protocol to study the effect of TCblR knockout on embryogenesis and development of the nervous system. Mice given only folinic acid are expected to develop abnormalities due to B12 deficiency; those receiving folinic acid and B12 should be normal, those given B12 alone should be normal and those receiving neither of the vitamins should present with abnormalities due to combined deficiency of both vitamins. The embryos are examined morphologically as well histologically for structural abnormalities. Successfully rescued fetuses will be followed with the rescuing agent to gradually produce the Cbl deficiency.

These studies also evaluate the effect of B12 deficiency in the litters after birth. The pups derived from the four groups identified above are reared without any pharmacologic vitamin supplements and monitored for growth and behavioral changes. Pups are sacrificed at various time points to assay for B12, folate, MMA, HCY and TCblR mRNA levels and to study morphological and structural changes in various tissues. The time points and duration of the experiments are dictated by preliminary findings.

Should all rescue strategies fail, the tissue specific knock-out Cre/Lox recombinase system is used to study the role of this receptor in the bone marrow and in the CNS, the two tissues in which the effects of B12 deficiency are most pronounced.

These studies provide insights into the role of B12 in the pathogenesis of B12 deficiency disorders. These studies evaluate the effects of Cbl deficiency at the cellular level as well as in the whole animal. These studies provide an animal model in which the metabolic, functional and structural abnormalities of Cbl deficiency can be evaluated.

Example 9

Generation and Characterization of Transcobalamin Receptor Blocking Antibodies

Figure 6A:
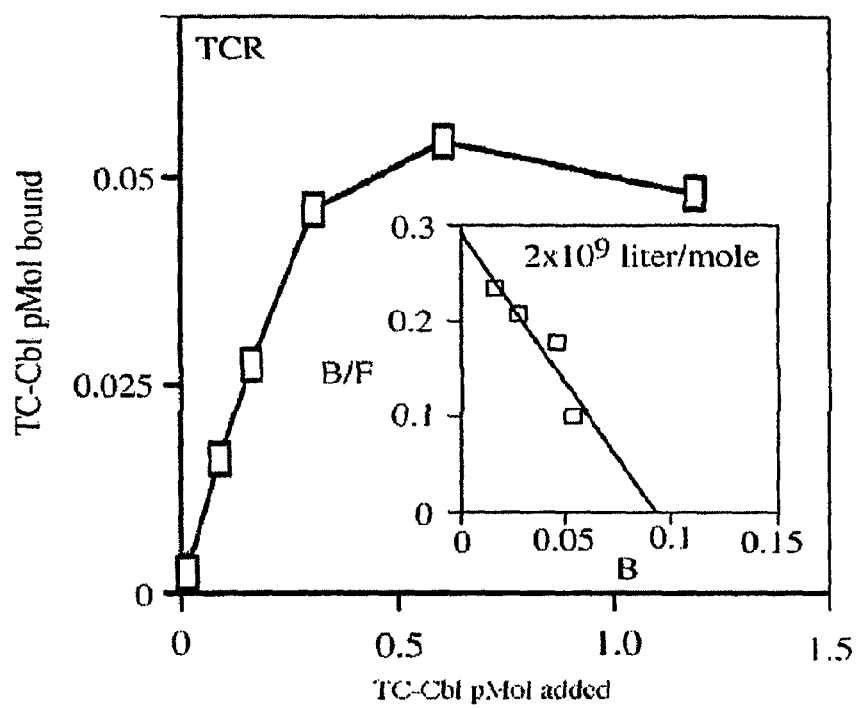
FIGS. 6A and 6B are graphs demonstrating the binding of TC-Cbl to purified TCblR (FIG. 6A) and recombinant extracellular domain of TCblR (FIG. 6B).
Figure 6B:
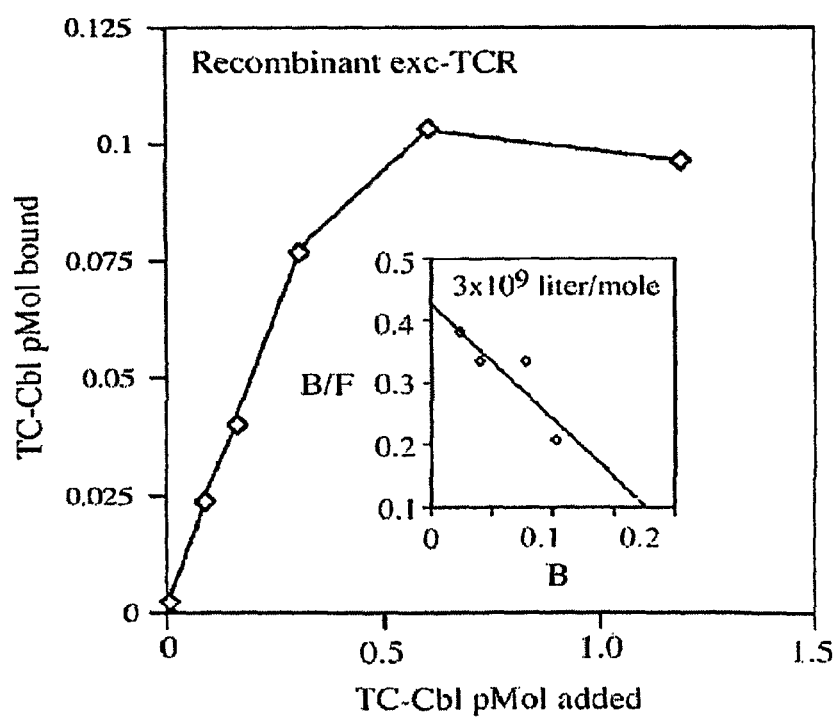

The extracellular (EXC) domain of TCblR was expressed in NSO myeloma cells. The amino acid sequence of the EXC is provided in SEQ ID NO:4. This recombinant protein was produced as a secreted fusion protein with the FC region of human IgG and subsequently cleaved and purified to generate the EXC fragment. A polyclonal antiserum specific for the EXC region (R&D Systems (goat anti-human 8D6 polyclonal antibody; Minneapolis, Minn.) was used to directly compare many of the properties of the protein purified from human placenta with the recombinant EXC fragment. As shown in FIGS. 6A and 6B, both proteins had similar binding properties for holo TC.

Western blot of the placental TCblR showed that the antiserum to the EXC fragment reacted with TCblR (FIG. 7) and did not react with any of the additional protein bands present in this preparation (see FIG. 7A). The size of the EXC-TCblR was larger than expected because some of the amino acids from the original fusion protein remained in the cleaved fragment. This antiserum has blocking properties in that it blocked the binding of TC-Cbl to the receptor when the apo-receptor was pre-incubated with the antibody (FIG. 8). Utilizing the blocking property of the antiserum, the uptake of TC-Cbl in K562 cells was tested. As shown in FIG. 9, the antiserum blocked 92% of the binding to cell surface receptors for TC-Cbl when the cells were pre-incubated with 1 ug of antibody for 1 hour at 4° C., thus confirming the existence of a single receptor on the plasma membrane for the cellular uptake of TC-Cbl. At 37° C., new receptors were expressed, as indicated by increased binding in control cells and a decrease in blocked receptors.

Immunization and Screening for anti TCblR HuMAbs

For the first round of immunization, three transgenic mice are injected with 10 ug of TCblR followed by two additional injections of 5 ug each. At this stage the mice are checked for anti TCblR antibodies and if the titer is low, additional immunizations are done. The mice are boosted with an additional 5 ug TCblR prior to fusion. Positive clones will be identified by ELISA by screening for human IgG and anti TCblR antibodies as described for TC. The primary objective of the first two screenings by ELISA is to eliminate non secretors. Positive clones from the above screening are subjected to additional screening to identify clones that are TCblR specific by the following assays.

a) Direct Binding of TCblR-TC[$^{57}$Co] Cbl:

Aliquots of hybridoma supernatants are incubated with 50 ul of a 10% suspension of Protein A membranes for 15 min. at 4° C. to capture the antibodies on the membranes and then washed with buffer to remove contaminating proteins. In a separate tube, purified TCblR is incubated with TC[$^{57}$Co] Cbl in Ca$^{++}$ containing buffer to form the TCblR-TC[$^{57}$Co] Cbl. Approximately 5000 cpm of the TCblR-TC[$^{57}$Co] Cbl are added to tubes containing the MAb-Protein A membranes and incubated at 4° C. for 1 h with gentle mixing. The Protein A membranes are pelleted at 15000 rpm for 10 min. and the radioactivity in the pellet represents the amount of TCblR bound to the MAb as TCblR-TC[$^{57}$Co] Cbl complex.

b) Blocking of TC[$^{57}$Co] Cbl from Binding TCblR:

An aliquot of purified TCblR, sufficient to bind ~5000 cpm of [$^{57}$Co]Cbl-TC is incubated with an aliquot of hybridoma supernatant sufficient to bind all the TCblR in the reaction in 2 h to form the MAb-TCblR complex. Preformed TC[$^{57}$Co] Cbl (10,000 cpm) is added to the reaction containing the MAb-TCblR complex and the incubation continued for an additional hour. The MAb-TCblR-TC[$^{57}$Co] Cbl is separated from TC[$^{57}$Co] Cbl using Protein A membranes. A parallel control reaction is setup without MAb incubated for 1 h (the same time period used for formation of TCblR-TC complex in the MAb containing reaction) and stopped using Con A agarose. Any decrease in the amount of TCblR-TC complex formed in samples containing MAb (protein A pellet) compared to the control sample (Con A agarose pellet) would be due to the blocking of TC-Cbl from binding to TCblR by the MAb.

These two screening tests are designed to identify all wells containing TCblR specific hybridomas for isolating single clones. Once the clones are isolated by limited dilution and identified as positive for blocking MAb, additional testing is done using cells in culture to confirm the blocking properties of each clone and to determine the amount of MAb needed for optimum effect.

c) Testing HuMAbs for Blocking of TC-Cbl from Binding to the Cell Surface Receptor.

Purified MAb or culture supernatants are incubated with 10$^6$ K562 cells for 1 h at 4° C. for the MAb to bind to the TCblR expressed on the cell surface. TC[$^{57}$Co] Cbl (5000 cpm) is added and the incubation continued for an additional hour. The cells are pelleted by centrifugation at 1000 rpm for 5 min.

The decrease in radioactivity in cells incubated with MAb compared with control cells is due to the blocking of TC-Cbl from binding to the receptor and provides a measure of blocking activity.

d) Testing of Anti-TCblR HuMAbs for their Ability to Deplete Intracellular Cbl and Induce Apoptosis in Cell Cultures.

To determine the amount of MAb needed to prevent the uptake of TC-Cbl in actively replicating cultures, 10$^5$ K562 cells are setup in 12 well plates containing 10% US saturated with [$^{57}$Co] Cbl and varying concentrations of purified MAb in a final volume of 1 ml at 37° C. Cells are collected at 24, 48, 72 and 96 h, and the cell number and radioactivity associated with the cell pellet is recorded.

Once an effective MAb concentration is determined, additional cultures are setup with the optimum MAb concentration, to study the effect of these MAbs on cell replication. Based on experience with anti TC MAbs, it is anticipated that cells may have to be maintained in MAb containing medium for more that 72-96 h in order to deplete intracellular stores of Cbl to a level below the critical concentration required to sustain growth and consequently, induce apoptosis.

The huMAbs generated according to these procedures are used to therapeutically to treat a variety of diseases and disorders associated with TCblR. i.e., by blocking TC binding to TCblR, or to identify tumor cells or target therapeutic agents to tumor cells.

Example 10

TCblR siRNA Inhibits Transcobalamin Uptake

The ability of siRNA directed against TCblR to inhibit cobalamin uptake was demonstrated using three synthetic siRNA constructs to the receptor gene. Each of these three constructs comprised a region of double-stranded RNA that included a TCblR mRNA sequence shown in FIG. 19. These siRNA molecules or a control siRNA were transiently transfected into HEK293 human kidney embryonic stem cells, and the ability of the cells to bind transcobalamin was determined using radiolabeled transcobalamin.

As shown in FIG. 20, all three of the siRNAs targeting TCblR mRNA effectively blocked the expression of the receptor as indicated by a decrease in the functional receptor expressed on the cell surface, whereas the control siRNA had no effect. As little as 2 nmoles of these siRNAs were effective in blocking TCblR expression by greater than 70%. Although these data were generated by transient transfection of siRNA, the results establish that other approaches, e.g., using viral vectors for delivery in vitro or in vivo, such as the lentivirus and adenovirus constructs, of the siRNA could be substituted to produce the knockdown of the TcblR receptor protein and reduced transcobalamin binding and uptake by cells.

Example 11

Recombinant TCblR Extracellular Domain Inhibits Transcobalamin Uptake

The full-length membrane TCblR consists of an extracellular domain (EXC), a transmembrane region, and a cytoplasmic fragment. Since binding of TC-Cbl occurs to the extracellular domain on the outside of the cell, it was hypothesized that this domain, independent of the membrane anchoring peptide sequence and the cytoplasmic domain, may bind TC-Cbl. This property of the receptor EXC fragment would allow it to be used as a "decoy target" to tie up the circulating TC-Cbl. This strategy is akin to using monoclonal antibodies to TC or the receptor to block B12 uptake into cells and, in effect, would produce a similar result.

To test this hypothesis, the recombinant extracellular fragment of TCblR was produced in human kidney embryonic stem cells HEK 293. For this production, the cDNA encoding the receptor was cut with restriction enzymes Kpn1 and PvuII, isolated in an agarose gel, and purified. The fragment generated consisted of the first 741 nucleotides of the cDNA and coded for the first 247 amino acids of the receptor protein. It also included the signal peptide to direct the protein to the plasma membrane for secretion into the medium. This fragment was cloned into a plasmid pcDNA3.1(+) that was linearized with Kpn1 and EcoRV. The plasmid with the cDNA encoding the receptor fragment was propagated in $E\ coli$ bacteria and purified.

This recombinant plasmid was transfected into HEK 293 cells, and the culture medium was assayed for TC-Cbl binding. Binding of TC-Cbl to a protein in the culture medium indicated the synthesis and secretion of the extracellular fragment of the receptor into the culture medium. This assay also confirmed that the receptor fragment produced and secreted by these cells was functional in that it bound holo TC, i.e., TC containing B12 bound to the EXC with the affinity and specificity of the intact full length receptor Protein.

Stable transfectants were generated by growing cells in the presence of the antibiotic geneticin; taking advantage of the antibiotic resistance gene in the pcDNA plasmid. HEK 293 cells selected for antibiotic resistance, thus, stably express and secrete the extracellular fragment of the receptor. Stable HEK 293 cell clones expressing the receptor fragment were propagated in DMEM medium containing geneticin and 72-96 hr culture medium was collected. The receptor protein in the culture medium was purified by a two step affinity chromatography procedure. First, recombinant human TC saturated with B12 was mixed with 1-2 liters of the culture medium. This resulted in the binding of the TC-Cbl with the receptor fragment.

Affinity matrix in the form of agarose to which a purified monoclonal antibody to human TC was covalently attached, was then added. The receptor-TC-Cbl complex was captured on the affinity matrix by virtue of the antibody binding to the TC. The matrix was washed, and the receptor fragment was eluted with buffer containing 0.5M $MgCl_2$. This elution selectively dissociated the receptor from TC-Cbl, leaving the TC-Cbl still bound to the monoclonal antibody. The eluted receptor was further purified by binding and elution from a wheat germ agglutinin-agarose affinity matrix. The carbohydrate moiety of this highly glycosylated protein binds specifically to wheat germ. The final product was homogeneously pure as judged by SDS-PAGE analysis and staining of the protein band (FIG. 21). The identity of the purified protein was further confirmed by western blot, whereby the protein reacted with an antiserum generated to the extra cellular fragment of the receptor (FIG. 21). This extracellular fragment of the receptor bound holo TC (TC saturated with B12) with the same specificity and affinity as the membrane bound native receptor.

The ability of the EXC fragment of TCblR to block cobalamin uptake was determined in vitro. K562 human erythroleukemia cells were incubated at 37° C. in medium containing recombinant human TC saturated with $^{57}Co$—B12. As shown in FIG. 22, at a 150-fold excess concentration of the extracellular fragment of the receptor, uptake of $^{57}Co$—B12 was completely blocked over the 3 hr incubation. At a 15-fold molar excess, greater than 70% of the uptake was blocked during the entire 3 hr incubation. These data demonstrate that recombinant TCblR EXC fragment can be used to inhibit cobalamin uptake. Based on the normal TC concentration in the blood and a total blood volume of 3 liters, it is predicted that a concentration of 150-fold excess soluble receptor can be easily maintained for therapeutic efficacy.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of identifying a modulator of cobalamin uptake into a cell, comprising:
   (a) contacting an isolated recombinantly-produced transcobalamin receptor polypeptide, or a fragment thereof comprising the extracellular region of the transcobalamin receptor, with transcobalamin: in the presence of a candidate modulator;
   (b) determining an amount of the transcobalamin bound to the transcobalamin receptor or fragment thereof; and
   (c) comparing the amount of bound transcobalamin to an amount bound in the absence of the candidate modulator,
   wherein a decreased or increased amount of bound transcobalamin in the presence of the candidate modulator as compared to in the absence of the candidate modulator indicates that the candidate modulator is a modulator of cobalamin uptake into a cell.

2. The method of claim 1, wherein the transcobalamin receptor polypeptide or fragment thereof comprises amino acids 32-229 of the polypeptide set forth in SEQ ID NO:1.

3. The method of claim 2, wherein the the transcobalamin receptor polypeptide or fragment thereof comprises amino acids 1-229 of the polypeptide sequence set forth in SEQ ID NO:1.

4. The method of claim 3, wherein the transcobalamin receptor polypeptide or fragment thereof comprises the polypeptide sequence set forth in SEQ ID NO:1.

5. A method of identifying a modulator of cobalamin uptake into a cell, comprising:
   (a) contacting a cell comprising an exogenous polynucleotide that encodes a transcobalamin receptor polypeptide or a fragment thereof comprising the extracellular region of the transcobalamin receptor with transcobalamin in the presence of a candidate modulator;
   (b) determining an amount of the transcobalamin taken up by the cell; and
   (c) comparing the amount of transcobalamin taken up by the cell to an amount taken up in the absence of the candidate modulator,
   wherein a decreased or increased amount of transcobalamin taken up by the cell in the presence of the candidate modulator as compared to in the absence of the candidate modulator indicates that the candidate modulator is a modulator of cobalamin uptake into a cell.

6. The method of claim 5, wherein said exogenous polynucleotide comprises a sequence set forth in SEQ ID NO:2 or 3, or a fragment thereof.

7. The method of claim 1 or 5, wherein said candidate modulator is an antibody.

8. The method of claim 5, wherein the transcobalamin receptor polypeptide or fragment thereof comprises amino acids 32-229 of the polypeptide set forth in SEQ ID NO:1.

9. The method of claim 8, wherein the the transcobalamin receptor polypeptide or fragment thereof comprises amino acids 1-229 of the polypeptide sequence set forth in SEQ ID NO:1.

10. The method of claim 9, wherein the transcobalamin receptor polypeptide or fragment thereof comprises the polypeptide sequence set forth in SEQ ID NO:1.

11. A method of identifying a human antibody that inhibits cobalamin uptake into a cell, comprising:
    (a) contacting an isolated recombinantly-produced transcobalamin receptor polypeptide, or a fragment thereof comprising the extracellular region of the transcobalamin receptor, with transcobalamin in the presence of a human antibody specific for a transcobalamin receptor;
    (b) determining an amount of the transcobalamin bound to the transcobalamin receptor or fragment thereof; and
    (c) comparing the amount of bound transcobalamin to an amount bound in the absence of the antibody,
    wherein a decreased amount of bound transcobalamin in the presence of the antibody indicates that the antibody inhibits cobalamin uptake into a cell.

12. The method of claim 11, wherein the transcobalamin receptor polypeptide or fragment thereof comprises amino acids 32-229 of the polypeptide set forth in SEQ ID NO:1.

13. The method of claim 12, wherein the the transcobalamin receptor polypeptide or fragment thereof comprises amino acids 1-229 of the polypeptide sequence set forth in SEQ ID NO:1.

14. The method of claim 13, wherein the transcobalamin receptor polypeptide or fragment thereof comprises the polypeptide sequence set forth in SEQ ID NO:1.

15. The method of claim 11, wherein the human antibody is coupled to a therapeutic agent.

16. The method of claim 11, wherein the human antibody is an internalizing antibody.

17. A method of identifying a human antibody that inhibits cobalamin uptake into a cell, comprising:
    (a) contacting a cell expressing an exogenous transcobalamin receptor polypeptide, or a fragment thereof comprising the extracellular region of the transcobalam receptor, with transcobalamin in the presence of a human antibody that specifically binds the transcobalamin receptor polypeptide;
    (b) determining an amount of the transcobalamin taken up by the cell; and (c) comparing the amount of transcobalamin taken up by the cell to an amount taken up in the absence of the antibody, wherein a decreased amount of transcobalamin taken up by the cell indicates that the antibody is an inhibitor of cobalamin uptake into a cell.

18. The method of claim 17, wherein the transcobalamin receptor polypeptide or fragment thereof comprises amino acids 32-229 of the polypeptide set forth in SEQ ID NO:1.

19. The method of claim 18, wherein the the transcobalamin receptor polypeptide or fragment thereof comprises amino acids 1-229 of the polypeptide sequence set forth in SEQ ID NO:1.

20. The method of claim 19, wherein the transcobalamin receptor polypeptide or fragment thereof comprises the polypeptide sequence set forth in SEQ ID NO:1.

21. The method of claim 17, wherein the human antibody is coupled to a therapeutic agent.

22. The method of claim 17, wherein the human antibody is an internalizing antibody.

23. The method of any one of claims 1, 5, 11 or 17, wherein said transcobalamin receptor polypeptide comprises an amino acid sequence encoded by SEQ ID NO:3.

\* \* \* \* \*

UNITED STATES PATENT AND TRADEMARK OFFICE
CERTIFICATE OF CORRECTION

PATENT NO.         : 8,524,454 B2                                                                Page 1 of 1
APPLICATION NO.    : 12/296254
DATED              : September 3, 2013
INVENTOR(S)        : Quadros et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 21

<210> SEQ ID NO 1
<211> LENGTH: 282
<212> TYPE: PRT
<213> ORGANISM: Homo sapiens

<400> SEQUENCE: 1

Met Ser Gly Gly Trp Met Ala Gln Val Gly Ala Trp Arg Thr Gly Ala
 1               5                   10                  15

Leu Gly Leu Ala Leu Leu Leu Leu Gly Leu Gly Leu Glu
            20                  25                  30

Ala Ala Ala Ser Pro Leu Ser Thr Pro Thr Ser Ala Gln Ala Ala Gly
            35                  40                  45

Pro Ser Ser Gly Ser Cys Pro Pro Thr Lys Phe Gln Cys Arg Thr Ser
        50                  55                  60

Gly Leu Cys Val Pro Leu Thr Trp Arg Cys Asp Arg Asp Leu Asp Cys
 65                  70                  75                  80

Ser Asp Gly Ser Asp Glu Glu Glu Cys Arg Ile Glu Pro Cys Thr Gln
                85                  90                  95

Lys Gly Gln Cys Pro Pro Pro Gly Leu Pro Cys Pro Cys Thr Gly
            100                 105                 110

Val Ser Asp Cys Ser Gly Gly Thr Asp Lys Lys Leu Arg Asn Cys Ser
            115                 120                 125

Arg Leu Ala Cys Leu Ala Gly Glu Leu Arg Cys Thr Leu Ser Asp Asp
        130                 135                 140

Cys Ile Pro Leu Thr Trp Arg Cys Asp Gly His Pro Asp Cys Pro Asp
145                 150                 155                 160

Ser Ser Asp Glu Leu Gly Cys Gly Thr Asn Glu Ile Leu Pro Glu Gly
                165                 170                 175

Asp Ala Thr Thr Met Gly Pro Pro Val Thr Leu Glu Ser Val Thr Ser
            180                 185                 190

Leu Arg Asn Ala Thr Thr Met Gly Pro Pro Val Thr Leu Glu Ser Val
            195                 200                 205

Pro Ser Val Gly Asn Ala Thr Ser Ser Ala Gly Asp Gln Ser Gly
        210                 215                 220

Ser Pro Thr Ala Tyr Gly Val Ile Ala Ala Ala Val Leu Ser Ala
225                 230                 235                 240

Ser Leu Val Thr Ala Thr Leu Leu Leu Ser Trp Leu Arg Ala Gln
            245                 250                 255

Glu Arg Leu Arg Pro Leu Gly Leu Leu Val Ala Met Lys Glu Ser Leu
            260                 265                 270

Leu Leu Ser Glu Gln Lys Thr Ser Leu Pro
            275                 280

<210> SEQ ID NO 2
<211> LENGTH: 1260
<212> TYPE: DNA
<213> ORGANISM: Homo sapiens

<400> SEQUENCE: 2
tgcgcgtgcg cagggataag agagcggtct ggacagcgcg tggccggcgc cgctgtgggg      60
acagcatgag cggcggttgg atggcgcagg ttggagcgtg gcgaacaggg gctctgggcc     120
tggcgctgct gctgctgctc ggcctcggac taggcctgga ggccgccgcg agcccgcttt     180

```
ccaccccgac ctctgcccag gccgcaggcc ccagctcagg ctcgtgccca cccaccaagt    240
tccagtgccg caccagtggc ttatgcgtgc ccctcacctg gcgctgcgac agggacttgg    300
actgcagcga tggcagcgat gaggaggagt gcaggattga gccatgtacc cagaaagggc    360
aatgcccacc gccccctggc ctcccctgcc cctgcaccgg cgtcagtgac tgctctgggg    420
gaactgacaa gaaactgcgc aactgcagcc gcctggcctg cctagcaggc gagctccgtt    480
gcacgctgag cgatgactgc attccactca cgtggcgctg cgacgccac ccagactgtc     540 ccgactccag cgacgagctc ggctgtggaa ccaatgagat cctcccggaa ggggatgcca    600
caaccatggg gccccctgtg acccctggaga gtgtcacctc tctcaggaat gccacaacca    660 tggggcccccc tgtgaccctg gagagtgtcc cctctgtcgg gaatgccaca tcctcctctg    720
ccggagacca gtctggaagc ccaactgcct atggggttat gcagctgct gcggtgctca     780 gtgcaagcct ggtcaccgcc accctcctcc ttttgtcctg gctccgagcc caggagcgcc    840
tccgcccact ggggttactg gtggccatga aggagtccct gctgctgtca gaacagaaga    900
cctcgctgcc ctgaggacaa gcacttgcca ccaccgtcac tcagccctgg gcgtagccgg    960
acaggaggag agcagtgatg cggatgggta cccgggcaca ccagccctca gagacctgag   1020
ctcttctggc cacgtggaac ctcgaacccg agctcctgca gaagtggccc tggagattga   1080
gggtccctgg acactcccta tggagatccg gggagctagg atggggaacc tgccacagcc   1140
agaactgagg ggctggcccc aggcagctcc caggggtag aacggccctg tgcttaagac    1200
actcctgctg ccccgtctga gggtggcgat taaagttgct tcacatcctc aaaaaaaaaa   1260
```

<210> SEQ ID NO 3
<211> LENGTH: 849
<212> TYPE: DNA
<213> ORGANISM: Homo sapiens

<400> SEQUENCE: 3

```
atgagcggcg gttggatggc gcaggttgga gcgtggcgaa caggggctct gggcctggcg     60
ctgctgctgc tgctcggcct cggactaggc ctggaggccg ccgcgagccc gctttccacc    120
ccgacctctg cccaggccgc aggccccagc tcaggctcgt gccccaccca caagttccag    180
tgccgcacca gtggcttatg cgtgcccctc acctggcgct gcgacaggga cttggactgc    240
agcgatggca gcgatgagga ggagtgcagg attgagccat gtacccagaa agggcaatgc    300
ccaccgcccc ctggcctccc ctgcccctgc accggcgtca gtgactgctc tggggggaact    360 gacaagaaac tgcgcaactg cagccgcctg gcctgcctag caggcgagct ccgttgcacg    420
ctgagcgatg actgcattcc actcacgtgg cgctgcgacg ccacccaga ctgtcccgac     480 tccagcgacg agctcggctg tggaaccaat gagatcctcc cggaagggga tgccacaacc    540
atggggcccc ctgtgaccct ggagagtgtc acctctctca ggaatgccac aaccatgggg    600
ccccctgtga ccctggagag tgtcccctct gtcgggaatg ccacatcctc ctctgccgga    660
gaccagtctg gaagcccaac tgcctatggg gttattgcag ctgctgcggt gctcagtgca    720
agcctggtca ccgccaccct cctccttttg tcctggctcc gagcccagga gcgcctccgc    780
ccactggggt tactggtggc catgaaggag tccctgctgc tgtcagaaca gaagacctcg    840
ctgccttaa                                                           849
```

<210> SEQ ID NO 4
<211> LENGTH: 980
<212> TYPE: DNA
<213> ORGANISM: Homo sapiens -continued

<400> SEQUENCE: 4

```
taatttttgt attttttggta gagacgggag ttttactatg ttggccaggc tggtttagaa      60
ctcctgacct cgtgatccgc ctgcctcggc ctcccaaagt gctggggtta acaggcgtga     120
gccagcgcgc cggccaactt ttctaacaaa tggggtctca ctgtcaccca cgctggagtg     180
cagccccaag tgattctccc acctcagcct cctgagtagc tgggactaca aattagagcc     240
accatgccca gctaattttc ttttttcttg aggcgggcgg ggacttgctg tgttgcccag     300
gctgatctcg aactcctggg ctcaagcgat ctgcccgcct ctgcttccca aaatgctggg     360
atcacacacg tgacccaccg cgcccggcct ttattattaa atttaattaa ttaattgatt     420
aatgtttact aagagcctac tatgagtcaa gcactatgtg tcagatcctg agaataaagc     480
agtgagcaac agaagatccc tgccctccag tagctagcat tctatgggga ctcggacaac     540
aaaccagaat aagtaaataa aataaattac ctgtcggcgc acaaaagca gtgggatgag      600
ggaggaaatg cggagtgcct gaggggcgtg gctgccatat taaagaagat cacgaggcag     660
taacatttgc agcagtcctc atttggaacg ggaaataatg caaatgaaca ccaacaaatt     720
ccttcccatc cccagaagtt tctaacttca agcgggctcc ataccttcca actgatctgg     780
tcactgggga aagtggggac gggcctctaa ttctctttc cctgctattc tgacatttac     840
ggtacgcgta gccgcgggcg ccgcagaact caggggcttg gccccgccc caaccccgcg     900
cgtgcgcgtg cgcagggata agagagcggt ctggacagcg cgtggccggc gccgctgtgg     960
ggacagcatg agcggcggtt                                                 980
```

<210> SEQ ID NO 5
<211> LENGTH: 198
<212> TYPE: PRT
<213> ORGANISM: Artificial Sequence
<220> FEATURE:
<223> OTHER INFORMATION: Amino acid sequence for recombinant
      extracellular fragment of TCR and peptide fragments generated
      using endopeptidases and CNBr.

<400> SEQUENCE: 5

```
Glu Ala Ala Ala Ser Pro Leu Ser Thr Pro Thr Ser Ala Gln Ala Ala
  1               5                  10                  15

Gly Pro Ser Ser Gly Ser Cys Pro Pro Thr Lys Phe Gln Cys Arg Thr
                 20                  25                  30

Ser Gly Leu Cys Val Pro Leu Thr Trp Arg Cys Asp Arg Asp Leu Asp
             35                  40                  45

Cys Ser Asp Gly Ser Asp Glu Glu Glu Cys Arg Ile Glu Pro Cys Thr
         50                  55                  60

Gln Lys Gly Gln Cys Pro Pro Pro Gly Leu Pro Cys Pro Cys Thr
 65                  70                  75                  80

Gly Val Ser Asp Cys Ser Gly Gly Thr Asp Lys Lys Leu Arg Asn Cys
                 85                  90                  95

Ser Arg Leu Ala Cys Leu Ala Gly Glu Leu Arg Cys Thr Leu Ser Asp
                100                 105                 110

Asp Cys Ile Pro Leu Thr Trp Arg Cys Asp Gly His Pro Asp Cys Pro
            115                 120                 125

Asp Ser Ser Asp Glu Leu Gly Cys Gly Thr Asn Glu Ile Leu Pro Glu
        130                 135                 140

Gly Asp Ala Thr Thr Met Gly Pro Pro Val Thr Leu Glu Ser Val Thr
145                 150                 155                 160

Ser Leu Arg Asn Ala Thr Thr Met Gly Pro Pro Val Thr Leu Glu Ser
                165                 170                 175
```

Val Pro Ser Val Gly Asn Ala Thr Ser Ser Ser Ala Gly Asp Gln Ser
            180                 185                 190

Gly Ser Pro Thr Ala Tyr
        195

<210> SEQ ID NO 6
<211> LENGTH: 19
<212> TYPE: RNA
<213> ORGANISM: Homo sapiens

<400> SEQUENCE: 6
gcaggauuga gccauguac                                               19

<210> SEQ ID NO 7
<211> LENGTH: 19
<212> TYPE: RNA
<213> ORGANISM: Homo sapiens

<400> SEQUENCE: 7
gcugagcgau gacugcauu                                               19

<210> SEQ ID NO 8
<211> LENGTH: 19
<212> TYPE: RNA
<213> ORGANISM: Homo sapiens

<400> SEQUENCE: 8
gcuguggaac caaugagau                                               19

<210> SEQ ID NO 9
<211> LENGTH: 19
<212> TYPE: RNA
<213> ORGANISM: Homo sapiens

<400> SEQUENCE: 9
uggaagccca acugccuau                                               19

<210> SEQ ID NO 10
<211> LENGTH: 19
<212> TYPE: RNA
<213> ORGANISM: Homo sapiens

<400> SEQUENCE: 10
gccugcguua aagccuacu                                               19

<210> SEQ ID NO 11
<211> LENGTH: 19
<212> TYPE: RNA
<213> ORGANISM: Mus musculus

<400> SEQUENCE: 11
gccacaacua caaggauuu                                               19

<210> SEQ ID NO 12
<211> LENGTH: 19
<212> TYPE: RNA
<213> ORGANISM: Mus musculus

<400> SEQUENCE: 12
ccgaaaccca agugccuau                                               19

<210> SEQ ID NO 13
<211> LENGTH: 19

```
<212> TYPE: RNA
<213> ORGANISM: Mus musculus

<400> SEQUENCE: 13
gcagucagac ugggacaaa                                               19

<210> SEQ ID NO 14
<211> LENGTH: 19
<212> TYPE: RNA
<213> ORGANISM: Mus musculus

<400> SEQUENCE: 14
ucaggagagu gagcugcau                                               19

<210> SEQ ID NO 15
<211> LENGTH: 19
<212> TYPE: RNA
<213> ORGANISM: Mus musculus

<400> SEQUENCE: 15
gcuucuggcu ucucagcuu                                               19

<210> SEQ ID NO 16
<211> LENGTH: 50
<212> TYPE: RNA
<213> ORGANISM: Artificial Sequence
<220> FEATURE:
<223> OTHER INFORMATION: synthetic siRNA construct

<400> SEQUENCE: 16
gcgaugagga ggagugcagg auugaucaau ccugcacucc uccucaucgc             50

<210> SEQ ID NO 17
<211> LENGTH: 50
<212> TYPE: RNA
<213> ORGANISM: Artificial Sequence
<220> FEATURE:
<223> OTHER INFORMATION: synthetic siRNA construct

<400> SEQUENCE: 17
gaacugacaa gaaacugcgc aacugcaguu gcgcaguuuc uugucaguuc             50

<210> SEQ ID NO 18
<211> LENGTH: 50
<212> TYPE: RNA
<213> ORGANISM: Artificial Sequence
<220> FEATURE:
<223> OTHER INFORMATION: synthetic siRNA construct

<400> SEQUENCE: 18
cgagcucggc uguggaacca augagcucau ugguuccaca gccgagcucg             50

<210> SEQ ID NO 19
<211> LENGTH: 1254
<212> TYPE: DNA
<213> ORGANISM: Homo sapiens

<400> SEQUENCE: 19
ctggacagcg cgtggccggc gccgctgtgg ggacagcatg agcggcggtt ggatggcgca   60
ggttggagcg tggcgaacag gggctctggg cctggcgctg ctgctgctgc tcggcctcgg  120
actaggcctg gaggccgccg cgagcccgct tccaccccg acctctgccc aggccgcagg   180
ccccagctca ggctcgtgcc cacccaccaa gttccagtgc cgcaccagtg gcttatgcgt  240 gccctcacc tggcgctgcg acagggactt ggactgcagc gatggcagcg atgaggagga  300
```

```
gtgcaggatt gagccatgta cccagaaagg gcaatgccca ccgcccctg gcctcccctg        360 cccctgcacc ggcgtcagtg actgctctgg gggaactgac aagaaactgc gcaactgcag        420
ccgcctggcc tgcctagcag gcgagctccg ttgcacgctg agcgatgact gcattccact        480
cacgtggcgc tgcgacggcc acccagactg tcccgactcc agcgacgagc tcggctgtgg        540
aaccaatgag atcctcccgg aaggggatgc acaaccatg gggcccctg tgaccctgga         600 gagtgtcacc tctctcagga atgccacaac catggggccc cctgtgaccc tggagagtgt        660
cccctctgtc gggaatgcca catcctcctc tgccggagac cagtctggaa gcccaactgc        720
ctatggggtt attgcagctg ctgcggtgct cagtgcaagc ctggtcaccg ccaccctcct        780
ccttttgtcc tggctccgag cccaggagcg cctccgccca ctggggttac tggtggccat        840
gaaggagtcc ctgctgctgt cagaacagaa gacctcgctg ccctgaggac aagcacttgc        900
caccaccgtc actcagccct gggcgtagcg ggacaggagg agagcagtga tgcggatggg        960
tacccgggca caccagccct cagagacctg agctcttctg gccacgtgga acctcgaacc       1020
cgagctcctg cagaagtggc cctggagatt gagggtccct ggacactccc tatggagatc       1080
cggggagcta ggatggggaa cctgccacag ccagaactga ggggctggcc ccaggcagct       1140 cccaggggt agaacggccc tgtgcttaag acactcctgc tgccccgtct gagggtggcg        1200
attaaagttg cttcacatcc tcaaaaaaa aaaaaaaaa aaaaaaaaaa aaaa              1254

<210> SEQ ID NO 20
<211> LENGTH: 1235
<212> TYPE: DNA
<213> ORGANISM: Homo sapiens

<400> SEQUENCE: 20
ggcgccgctg tggggacagc atgagcggcg gttggatggc gcaggttgga gcgtggcgaa         60 cagggctct gggcctggcg ctgctgctgc tgctcggcct cggactaggc ctggaggccg        120
ccgcgagccc gctttccacc ccgacctctg cccaggccgc aggccccagc tcaggctcgt        180
gcccacccac caagttccag tgccgcacca gtggcttatg cgtgcccctc acctggcgct        240
gcgacaggga cttggactgc agcgatggca gcgatgagga ggagtgcagg attgagccat        300
gtacccagaa agggcaatgc ccaccgcccc ctggcctccc ctgccctgc accggcgtca        360 gtgactgctc tgggggaact gacaagaaac tgcgcaactg cagccgcctg gcctgcctag       420
caggcgagct ccgttgcacg ctgagcgatg actgcattcc actcacgtgg cgctgcgacg       480
gccacccaga ctgtcccgac tccagcgacg agctcggctg tggaaccaat gagatcctcc       540
cggaagggga tgccacaacc atggggcccc ctgtgaccct ggagagtgtc acctctctca       600
ggaatgccac aaccatgggg cccctgtga cctggagag tgtcccctct gtcgggaatg         660
ccacatcctc ctctgccgga gaccagtctg gaagcccaac tgcctatggg gttattgcag       720
ctgctgcggt gctcagtgca agcctggtca ccgccaccct cctccttttg tcctggctcc       780
gagcccagga gcgcctccgc ccactggggt tactggtggc catgaaggag tccctgctgc       840
tgtcagaaca agacctcg ctgccctgag gacaagcact tgccaccacc gtcactcagc         900
cctgggcgta gccggacagg aggagagcag tgatgcggat gggtacccgg gcacaccagc       960
cctcagagac ctgagctctt ctggccacgt ggaacctcga acccgagctc tgcagaagt       1020 ggccctggag attgagggtc cctggacact ccctatggag atccggggag ctaggatggg       1080
gaacctgcca cagccagaac tgaggggctg gccccaggca gctcccaggg ggtagaacgg       1140
ccctgtgctt aagacactcc tgctgccccg tctgagggtg gcgattaaag ttgcttcaca       1200
```

```
tccttaaaaa aaaaaaaaaa aaaaaaaaaa aaaaa                                    1235

<210> SEQ ID NO 21
<211> LENGTH: 4
<212> TYPE: PRT
<213> ORGANISM: unknown
<220> FEATURE:
<223> OTHER INFORMATION: bacterial Thioredoxin-A variable loop sequence

<400> SEQUENCE: 21

Cys Gly Pro Cys
 1
```